US011978535B2

(12) United States Patent
Halperin et al.

(10) Patent No.: US 11,978,535 B2
(45) Date of Patent: May 7, 2024

(54) METHODS OF DETECTING SOMATIC AND GERMLINE VARIANTS IN IMPURE TUMORS

(71) Applicant: THE TRANSLATIONAL GENOMICS RESEARCH INSTITUTE, Phoenix, AZ (US)

(72) Inventors: Rebecca Halperin, Phoenix, AZ (US); David Craig, La Canada, CA (US)

(73) Assignee: The Translational Genomics Research Institute, Phoenix, AZ (US)

(*) Notice: Subject to any disclaimer, the term of this patent is extended or adjusted under 35 U.S.C. 154(b) by 1093 days.

(21) Appl. No.: 16/479,200

(22) PCT Filed: Feb. 1, 2018

(86) PCT No.: PCT/US2018/016522
§ 371 (c)(1),
(2) Date: Jul. 18, 2019

(87) PCT Pub. No.: WO2018/144782
PCT Pub. Date: Aug. 9, 2018

(65) Prior Publication Data
US 2019/0362808 A1    Nov. 28, 2019

Related U.S. Application Data

(60) Provisional application No. 62/453,492, filed on Feb. 1, 2017.

(51) Int. Cl.
*G16B 40/00* (2019.01)
*G16B 20/20* (2019.01)
(Continued)

(52) U.S. Cl.
CPC ............ *G16B 40/00* (2019.02); *G16B 20/20* (2019.02); *G16B 20/40* (2019.02); *G16B 30/10* (2019.02); *G16B 50/00* (2019.02)

(58) Field of Classification Search
CPC ............ C12Q 2600/156; C12Q 1/6886; C12Q 1/6869; C12Q 2537/16; C12Q 1/6858;
(Continued)

(56) References Cited

U.S. PATENT DOCUMENTS

2003/0092021 A1* 5/2003 Thilly ................. C12Q 1/6827
702/20
2003/0186250 A1* 10/2003 Shah .................... C12Q 1/6809
702/20
(Continued)

FOREIGN PATENT DOCUMENTS

CA        2354322 A1 *  6/2000
CA        2912059 A1 * 11/2014 ............. G16B 20/00
(Continued)

OTHER PUBLICATIONS

Search machine translation: A Method And Composition For Treatment And Diagnosis Of Colorectal Cancer of CN-103907022-A to Chapman, retrieved Feb. 23, 2023, 51 pages. (Year: 2023).*
(Continued)

*Primary Examiner* — Matthew C Bella
*Assistant Examiner* — Dennis Rosario
(74) *Attorney, Agent, or Firm* — Rodney J. Fuller; BOOTH UDALL FULLER, PLC

(57) ABSTRACT

A system is provided that considers allele fraction shifts as a function of copy number and clonal heterogeneity. The system leverages differences between allele frequencies to differentiate between somatic and normal variants in impure tumor samples. In solid tumors, stromal cells and infiltrating lymphocytes are typically interspersed among the tumor cells. The normal cell contamination in tumors can be leveraged to differentiate somatic from germline variants. We explicitly model allelic copy number and clonal sample fractions so that we can examine how these factors impact
(Continued)

the power to detect somatic variants. The system models the copy number alterations, which can also affect the allele frequencies of both somatic and germline variants. The expected allele frequencies can be calculated. The expected allele frequencies for somatic and germline differ with tumor content for different copy number alterations.

5 Claims, 35 Drawing Sheets

(51) Int. Cl.
    *G16B 20/40*     (2019.01)
    *G16B 30/10*     (2019.01)
    *G16B 50/00*     (2019.01)

(58) Field of Classification Search
    CPC ............ C12Q 2537/165; C12Q 1/6827; C12Q 1/6883; G16B 20/10; G16B 20/20; G16B 20/00; G16B 40/00; G16B 30/00; G16B 30/10; G16H 10/40; G06N 20/00; G06N 7/01; G06N 5/04; G06N 3/00; G06N 5/00; G06N 7/00; G06N 3/08
    See application file for complete search history.

(56) References Cited

U.S. PATENT DOCUMENTS

| | | | | |
|---|---|---|---|---|
| 2011/0172113 | A1* | 7/2011 | Parr | C07K 14/4748 536/23.4 |
| 2013/0337444 | A1* | 12/2013 | Ferree | C12Q 1/6886 536/24.31 |
| 2015/0178445 | A1 | 6/2015 | Cibulskis et al. | |
| 2015/0324519 | A1* | 11/2015 | Liu | G16H 20/00 702/20 |
| 2016/0032396 | A1* | 2/2016 | Diehn | G16B 30/00 506/26 |
| 2016/0306923 | A1* | 10/2016 | van Rooyen | G16B 30/20 |
| 2017/0202939 | A1* | 7/2017 | Carreno | A61K 35/17 |
| 2018/0016314 | A1* | 1/2018 | Harley | C07K 16/2896 |
| 2018/0163261 | A1* | 6/2018 | Zeigler | C12Q 1/68 |

FOREIGN PATENT DOCUMENTS

| | | | | |
|---|---|---|---|---|
| CN | 103907022 | A * | 7/2014 | ........... C12Q 1/6886 |
| WO | WO-2012167112 | A2 * | 12/2012 | ........... C12Q 1/6886 |

OTHER PUBLICATIONS

Tan, A., et al. Unified representation of genetic variants. Bioinformatics 2015; 31:2202-2204.
Lee, H., et al. Genomic dark matter: the reliability of short read mapping illustrated by the genome mappability score. Bioinformatics 2012; 28:2097-2105.
Pietras, K., et al. Hallmarks of cancer: interactions with the tumor stroma. Exp Cell Res 2010; 316:1324-1331.
Aran, D., et al. Systematic pan-cancer analysis of tumour purity. Nat Commun 2015; 6:8971.
Ewing, A. D., et al. Combining tumor genome simulation with crowdsourcing to benchmark somatic single-nucleotide-variant detection. Nat Methods 2015; 12:623-630.
Kwei, K. A., et al. Genomic instability in breast cancer: pathogenesis and clinical implications. Mol Oncol 2010; 4:255-266.
Van Allen, E. M., et al. Genomic correlates of response to CTLA-4 blockade in metastatic melanoma. Science 2015; 350:207-211.
Sathirapongsasuti, J. F., et al. Exome sequencing-based copy-number variation and loss of heterozygosity detection: ExomeCNV. Bioinformatics 2011; 27:2648-2654.
Favero, F., et al. Sequenza: allele-specific copy number and mutation profiles from tumor sequencing data. Ann Oncol 2015; 26:64-70.
Roth, A., et al. PyClone: statistical inference of clonal population structure in cancer. Nat Methods 2014; 11:396-398.
Desper, L., et al. THetA: inferring intra-tumor heterogeneity from high-throughput DNA sequencing data. Genome Biol 2013; 14:R80.
Cancer Hotspots. Single residue mutation hotspots identified in 11,119 tumor samples by the algorithm described in Chang et al. 2016. Accessed Dec. 15, 2017 at http://cancerhotspots.org/#/home.
Hanahan, D., et al. The Hallmarks of Cancer. Cell 2000; 100:57-70.
Van Allen, E. M., et al. Whole-exome sequencing and clinical interpretation of FFPE tumor samples to guide precision cancer medicine. Nat Med 2014; 20:682-688.
Bailey, M. H., et al. Comprehensive characterization of cancer driven genes and mutations. Cell 2018; 173:371-385.
Cheng, D. T., et al. Memorial Sloan Kettering-Integrated Mutation Profiling of Actionable Cancer Targets (MSK-Impact): a hybridization capture-based next-generation sequencing clinical assay for solid tumor molecular oncology. J Mol Diagn 2015; 17:251-26.
Frampton, G. M., et al. Development and validation of a clinical cancer genomic profiling test based on massively parallel DNA sequencing. Nat Biotechnol 2013; 31:1023-1031.
Khurana, E., et al. Role of non-coding sequence variants in cancer. Nat Rev Genet 2016; 17:93-108.
Marrone, M., et al. Opportunities for translational epidemiology: the important role of observational studies to advance precision oncology. Cancer Epidemiol Prev Biomark 2015; 24:484-489.
Waldron, L., et al. Expression profiling of archival tumors for long-term health studies. Clin Cancer Res 2012; 18:6136-6146.
Cheng, F., et al. Advances in computational approaches for prioritizing driver mutations and significantly mutated genes in cancer genomes. Brief Bioinform 2016; 17:642-656.
Wei, L., et al. Pitfalls of improperly procured adjacent non-neoplastic tissue for somatic mutation analysis using next-generation sequencing. BMC Med Genomics 2016; 9:64.
Dotto, G. P. Multifocal epithelial tumors and field cancerization: stroma as a primary determinant. J Clin Invest 2014; 124:1446-1453.
Heaphy, C. M., et al. Mammary field cancerization: molecular evidence and clinical importance. Breast Cancer Res Treat 2009; 118:229-239.
Nonn, L., et al. Evidence for field cancerization of the prostate. Prostate 2009; 69:1470-1479.
Hoang, M. L., Genome-wide quantification of rare somatic mutations in normal human tissues using massively parallel sequencing. Proc Natl Acad Sci USA 2016; 113:9846-9851.
Martincorena, I., et al. High burden and pervasive positive selection of somatic mutations in normal human skin. Science 2015; 348:880-886.
Jones, S., et al. Personalized genomic analyses for cancer mutation discovery and interpretation. Sci Transl med 2015; 7:283ra53.
Halperin, R. F., et al. A method to reduce ancestry related germline false positives in tumor only somatic variant calling. BMC Med Genomics 2017; 10:61.
Kalatskaya, I., et al. ISOWN: accurate somatic mutation identification in the absence of normal tissue controls. Genome Med 2017; 9:59.
Smith, K. S., SomVarIUS: somatic variant identification from unpaired tissue samples. Bioinformatics 2015: 32:808-813.
Riester, M., et al. PureCN: copy number calling and SNV classification using targeted short read sequencing. Source Code Biol Med 2016; 11:13.
Byron, S. A., et al. Prospective feasibility trial for genomics-informed treatment in recurrent and progressive glioblastoma. Clin Cancer Res 2017; 24:295-305.
Christoforides, A., et al. Identification of somatic mutations in cancer through Bayesian-based analysis of sequenced genome pairs. BMC Genomics 2013; 14:302.
Saunders, C. T., et al. Strelka: accurate somatic small-variant calling from sequenced tumor-normal samples pairs. Bioinformatics 2012; 28:1811-1817.
Cibulskis, K., et al. Sensitive detection of somatic point mutations in impure and heterogeneous cancer samples. Nat Biotechnol 2013; 31:213-219.

(56) References Cited

OTHER PUBLICATIONS

Sherry, S. T., et al. dbSNP: the NCBI database of genetic variation. Nucleic Acids Res 2001; 29:308-311.
Depristo, M. A., et al. A framework for variation discovery and genotyping using next generation DNA sequencing data. Nat Genet 2011; 43:491-498.
Teer, J. K., et al. Evaluating somatic tumor mutation detection without matched normal samples. Hum Genomics 2017; 11:22.
Andor, N., et al. Pan-cancer analysis of the extent and consequences of intratumor heterogeneity. Nat Med 2016; 22:105-113.
Andor, N., et al. Genomic instability in cancer: teetering on the limit of tolerance. Cancer Res 2017; 77:2179-2185.
Saunders, N. A., et al. Role of intratumoural heterogeneity in cancer drug resistance: molecular and clinical perspectives. EMBO Mol Med 2012; 4:675-684.
Troester, M. A., et al. DNA defects, epigenetics, and gene expression in cancer-adjacent breast: a study from The Cancer Genome Atlas. NPJ Breast Cancer 2016; 2:16007.
Halperin, R. F., et al. Joint analysis of matched tumor samples with varying tumor contents improves somatic variant calling in the absence of a germline sample. bioRxiv 2018; 364943.
Raymond, V. M., et al. Germline findings in tumor-only sequencing: points to consider for clinicians and laboratories. J Natl Cancer Inst 2016; 108:djv351.
Garofalo, A., et al. The impact of tumor profiling approaches and genomic data strategies for cancer precision medicine. Genome Med 2016; 8:79.
THE 1000 Genomes Project Consortium. An integrated map of genetic variation from 1,092 human genomes. Nature 2012; 491:56-65.
Kurian, A. W., et al. Clinical evaluation of a multiple-gene sequencing panel for hereditary cancer risk assessment. J Clin Oncol 2014; 32:2001-2009.
Richards, C. S., et al. ACMG recommendations for standards for interpretation and reporting of sequence variations: revisions 2007. Genet Med 2008; 10:294-300.
Vogelstein, B., et al. Cancer genome landscapes. Science. 2013;339:1546-1558.
Meric-Bernstam, F., et al. Incidental germline variants in 1000 advanced cancers on a prospective somatic genomic profiling protocol. Ann Oncol 2016; 27:795-800.
Leiserson, M. D. M., et al. Pan-Cancer network analysis identifies combinations of rare somatic mutations across pathways and protein complexes. Nat Genet 2015; 47:106-114.
Piraino, S. W., et al. Beyond the exome: the role of non-coding somatic mutations in cancer. Ann Oncol 2016: 27:240-248.
Vinagre, J., et al. Frequency of TERT promoter mutations in human cancers. Nat Commun 2013; 4:2185.
Lawrence, M. S., et al. Mutational heterogeneity in cancer and the search for new cancer genes. Nature 2013; 499:214-218.
Fu, Y., et al. FunSeq2: a framework for prioritizing noncoding regulatory variants in cancer. Genome Biol 2014; 15(10):480.
Kilpivaara, O., et al. Diagnostic cancer genome sequencing and the contribution of Germline variants. Science 2013; 339:1559-1562.
Li, J., et al. A dual model for prioritizing cancer mutations in the non-coding genome based on Germline and somatic events. PLoS Comput Biol 2015; 11:e1004583.
Li, H., et al. Fast and accurate short read alignment with burrows-wheeler transform. Bioinformatics 2009; 25:1754-1760.
Flicek, P., et al. Ensembl 2013. Nucleic Acids Res 2013; 41:D48-55.
Mose, L. E., et al. ABRA: improved coding indel detection via assembly-based realignment. Bioinformatics 2014; 30:2813-2815.
Li, H. A statistical framework for SNP calling, mutation discovery, association mapping and population genetical parameter estimation from sequencing data. Bioinformatics 2011; 27(21):2987-2993.
Garrison, E., et al. Haplotype-based variant detection from short-read sequencing. arXiv 2012; arXiv:1207.3907 [q-bio.CN]; Available from: http://arxiv.org/abs/1207.3907.
Oh, Ensel, "Comparison of Accuracy of Whole-Exome Sequencing with Formalin-Fixed Paraffin-Embedded and Fresh Frozen Tissue Samples", PLoS One, 10(12):1-13 (Dec. 7, 2015).
Fang, Li Tai et al., "An Ensemble Approach to Accurately Detect Somatic Mutations Using SomaticSeq", Genome Biology, 16(197):1-13 (Sep. 17, 2015).
Lonigro, Robert J. et al., "Detection of Somatic Copy Number Alterations in Cancer Using Targeted Exome Capture Sequencing", Neoplasia, 13(11):1019-1025 (Nov. 2011).

* cited by examiner

C.

| | Filt_TP | Filt_FN | Filt_FP | Pool_TP | Pool_FN | Pool_FP | Joint_TP | Joint_FN | Joint_FP |
|---|---|---|---|---|---|---|---|---|---|
| GBM-003 | 240 | 13 | 403 | 161 | 92 | 70 | 144 | 111 | 42 |
| GBM-005 | 184 | 0 | 573 | 98 | 86 | 111 | 133 | 48 | 54 |
| GBM-006 | 137 | 25 | 601 | 80 | 82 | 32 | 92 | 68 | 24 |
| GBM-008 | 219 | 4 | 413 | 152 | 71 | 29 | 119 | 103 | 14 |
| GBM-009 | 199 | 3 | 503 | 116 | 86 | 113 | 117 | 81 | 10 |
| GBM-014 | 294 | 29 | 438 | 150 | 173 | 145 | 136 | 186 | 80 |
| GBM-016 | 283 | 47 | 538 | 217 | 113 | 51 | 235 | 93 | 24 |

Figure 1C

| Sample name | Cancer type | Self reported ancestry | Reads (Millions) | Mean target coverage | % Covered at 100X |
|---|---|---|---|---|---|
| GBM6-HA | Glioblastoma | Hispanic | 897 | 553X | 95.7 |
| GBM1-EA | Glioblastoma | Caucasian | 2768 | 2101X | 98.3 |
| TNBC3-AA | Breast | African American | 905 | 599X | 96.1 |
| TNBC4-AA | Breast | African American | 906 | 546X | 95.4 |
| TNBC6-AA | Breast | African American | 1040 | 658X | 95.4 |
| TNBC7-AA | Breast | African American | 899 | 588X | 95.6 |
| TNBC11-EA | Breast | Caucasian | 1066 | 645X | 95.8 |
| TNBC14-EA | Breast | Caucasian | 875 | 454X | 94.5 |
| TNBC15-GH | Breast | Ghanaian | 598 | 1012X | 97.4 |

Figure 2

| | Variant Type | Germline Callers | Somatic vs Matched Normals | Somatic vs. Reference | Has RS |
|---|---|---|---|---|---|
| High Confidence | Germline Homozygous Alt | 1/1 with QUAL>30 in 3 of 3 | - | - | - |
| | Germline Het DB | 0/1 with QUAL>30 in 3 of 3 | - | - | Yes |
| | Germline Het Private | 0/1 with QUAL >30 in 3 of 3 | - | - | No |
| | Somatic | 0/0 with QUAL>30 or no call in 3 of 3 | SNVs: 3 of 3 callers indels: 2 of 2 callers | SNVs: 3 of 3 callers indels: 2 of 2 callers | - |
| | Non Variant | 0/0 with QUAL>30 or no call in 3 of 3 | 0 | 0 | - |
| Low Confidence | Germline Homozygous Alt | 1/1 with QUAL>30 in 1 or 2 | - | - | - |
| | Germline Het DB | 0/1 with QUAL>30 in 1 or 2 | - | - | Yes |
| | Germline Het Private | 0/1 with QUAL >30 in 1 or 2 | - | - | No |
| | Somatic | 0/0 with QUAL>30 or no call in at least 1 | At least 1 caller | At least 1 caller | - |
| | Non Variant | 0/0 with QUAL>30 or no call in 1 or 2 | 0 | 0 | - |
| Unknown | | Different genotypes with QUAL>30 | - | - | - |
| | | QUAL <30 in 3 of 3 | - | - | - |
| | | 0/1 with QUAL>30 in at least 1 caller | At least 1 caller | At least 1 caller | - |

Figure 3

| Parameter | Default value or source | Description |
|---|---|---|
| K | 3 | Number of Clones |
| $f_\pi$ | 0.5 | Mode of prior distribution of f |
| $\alpha_\pi$ | 1.5 | Determines shape of prior distribution of f |
| $\pi(N=0)...\pi(N=3)$, $\pi(N\geq 4)$ | 0.1, 0.15, 0.5, 0.15, 0.1 | Copy Number Priors |
| $\pi(M=0), \pi(M=1), \pi(M\geq 2)$ | [0.25; 0.5; 0.25] | Minor Allele Copy Number Priors |
| $\alpha_{seg}$ | 1E-05 | Segmentation significance cutoff |
| $\omega$ | COSMIC | Number of cancer variants observed at the position |
| $F_A, F_B$ | 1000 Genomes | Population Allele Frequencies |
| $\rho_{SNV}, \rho_{indel}$ | 1E-5, 1E-6 | Constant for calculating prior somatic |
| $F_{p-SNV}, F_{p-indel}$ | 7.14E-5, 1.43E-5 | Population allele frequencies assigned to alleles not seen in input population |
| $F_{max\text{-}somatic}$ | 1E-03 | Maximum population allele frequency to be considered a possible somatic variant |
| $Q_{min}^m$ | 10 | Minimum mapping quality to count read |
| $Q_{min}^b$ | 5 | Minimum base quality to count base |
| $T_{PASS}$ | 0.99 | Minimum posterior probability of belonging to the PASS group to be called pass |
| $T_{Somatic}$ | 0.8 | Minimum posterior probability of variant is somatic to be called somatic |
| $T_{Germline}$ | 0.8 | Minimum posterior probability of variant is germline to be called somatic |

Figure 6

| Metric | Criteria PASS | Criteria Reject |
|---|---|---|
| Percentage of Bases with MQ>$MQ_{min}$ and BQ>$BQ_{min}$ | >80% | <70% |
| Percentage of Bases that support the A or B allele | >95% | <90% |
| Minimum percentage of reads from forward or reverse strand | >1% | <0.1% |
| Minimum average mapping quality of reads supporting A or B allele | >35 | <30 |
| Minimum average base quality of bases supporting A or B allele | >25 | <20 |
| Maximum average percentage of mismatches in reads supporting A or B alleles | <2.5% | >5% |
| Minimum average distance from either end of sequence of A or B allele | >30 | <10 |
| Difference in average percentage of forward strand between A and B allele | <10% | >20% |
| Difference in average base quality between A and B alleles | <5 | >10 |
| Difference in average mapping quality between A and B alleles | <10 | >15 |
| Difference in average percentage of mismatches between A and B alleles | <1% | >2% |
| Difference in average read position between A and B alleles | <10 | >20 |
| Quality score of position from unmatched controls | >30 | <10 |
| Mean quality score in region | >20 | <10 |

Figure 7

| Variable | Descriptions |
|---|---|
| *Inputs to model* | |
| $R_T, R_B$ | Total read depth, B allele read depth |
| $\pi_S, \pi_{AB}, \pi_{AA}$ | prior probability of somatic, germline heterozygous, germline homozygous variant |
| $Q_A^m, Q_B^m$ | Mean mapping quality of reads supporting the A or B allele |
| $Q_B^b$ | Mean base quality of bases supporting B allele |
| X | Total number of exons |
| Y | Number of heterozygous germline variants |
| Z | Number of somatic variants |
| G | Number of segments |
| *Parameters fit in maximization* | |
| $f_i$ | fraction of cells in the sample with the variants in clone i |
| C | centering parameter |
| W | controls the spread of the allelic fraction distributions |
| *Intermediate variables* | |
| N | total copy number |
| M | minor allele copy number |
| $\phi^S, \phi^G$ | expected allele fraction of somatic or germline variant |
| $I_S, I_i$ | Index of clonal subset containing somatic variant or copy number variant |
| $Q^*$ | Number of copy number altered exons |
| *Other notation* | |
| $G_{AA}, G_{AB}$ | Germline homozygous or heterozygous genotype |
| O | Other genotype beside somatic, germline homozygous AA, or germline heterozygous AB |
| U | Unknown genotype due to poor mapping |
| i | Index of clonal subset {1, 2, ..., K} |
| j | Index of segment {1, 2, ..., G} |
| s | Index of somatic variant {1, 2, ..., Z} |
| h | Index of heterozygous variant {1, 2, ..., Y} |
| n | Index of exon {1, 2, ..., X} |

| Population Code | Population Description | Super Population Code |
|---|---|---|
| CHB | Han Chinese in Bejing, China | EAS |
| JPT | Japanese in Tokyo, Japan | EAS |
| CHS | Southern Han Chinese | EAS |
| CDX | Chinese Dai in Xishuangbanna, China | EAS |
| KHV | Kinh in Ho Chi Minh City, Vietnam | EAS |
| CEU | Utah Residents (CEPH) with Northern and Western European Ancestry | EUR |
| TSI | Toscani in Italia | EUR |
| FIN | Finnish in Finland | EUR |
| GBR | British in England and Scotland | EUR |
| IBS | Iberian Population in Spain | EUR |
| YRI | Yoruba in Ibadan, Nigeria | AFR |
| LWK | Luhya in Webuye, Kenya | AFR |
| GWD | Gambian in Western Divisions in the Gambia | AFR |
| MSL | Mende in Sierra Leone | AFR |
| ESN | Esan in Nigeria | AFR |
| ASW | Americans of African Ancestry in SW USA | AFR |
| ACB | African Caribbeans in Barbados | AFR |
| MXL | Mexican Ancestry from Los Angeles USA | AMR |
| PUR | Puerto Ricans from Puerto Rico | AMR |
| CLM | Colombians from Medellin, Colombia | AMR |
| PEL | Peruvians from Lima, Peru | AMR |
| GIH | Gujarati Indian from Houston, Texas | SAS |
| PJL | Punjabi from Lahore, Pakistan | SAS |
| BEB | Bengali from Bangladesh | SAS |
| STU | Sri Lankan Tamil from the UK | SAS |
| ITU | Indian Telugu from the UK | SAS |

| Code | Super Population |
|------|------------------|
| AFR  | African          |
| AMR  | Ad Mixed American |
| EAS  | East Asian       |
| EUR  | European         |
| SAS  | South Asian      |

Figure 9B

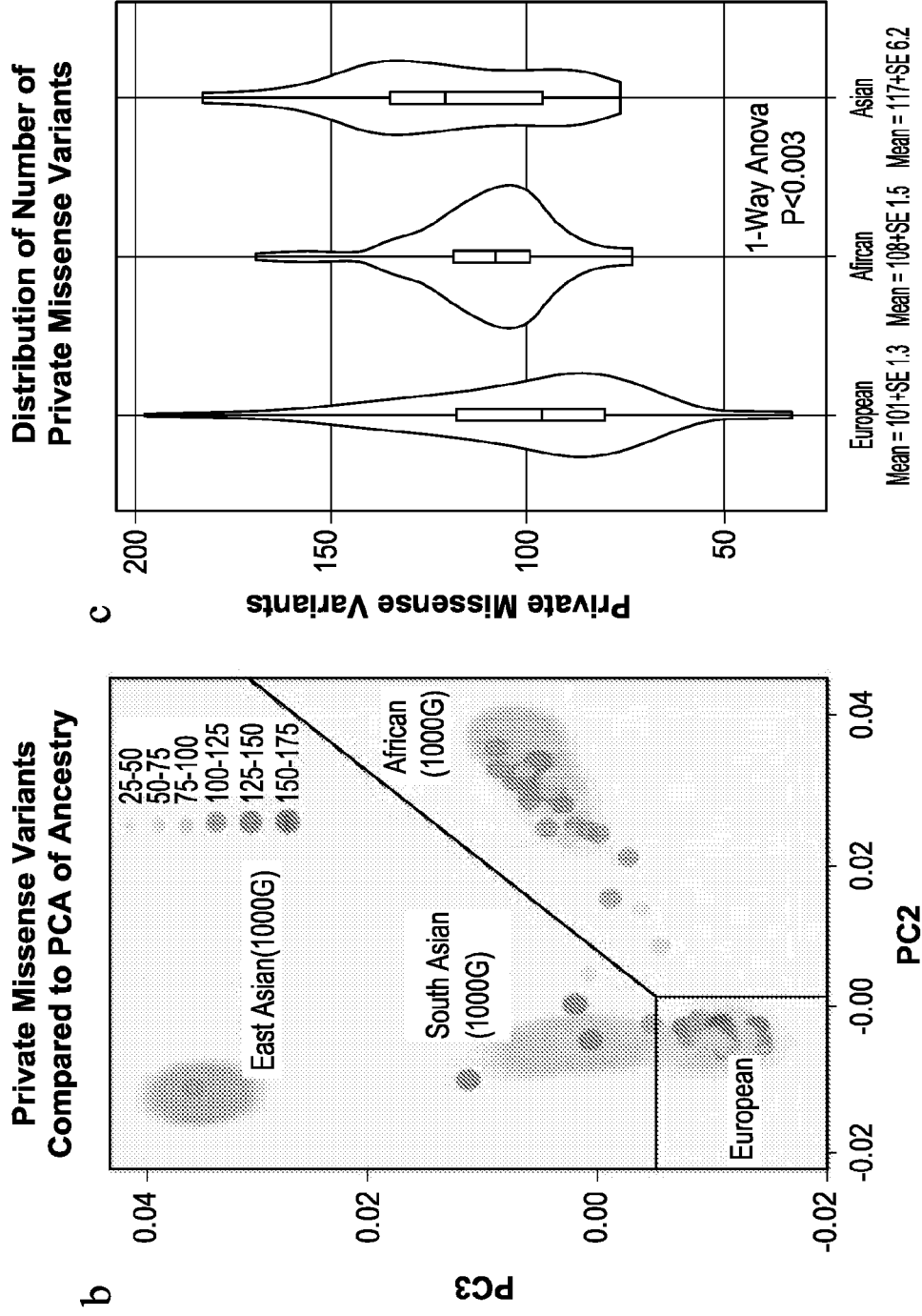
Figure 10b-c

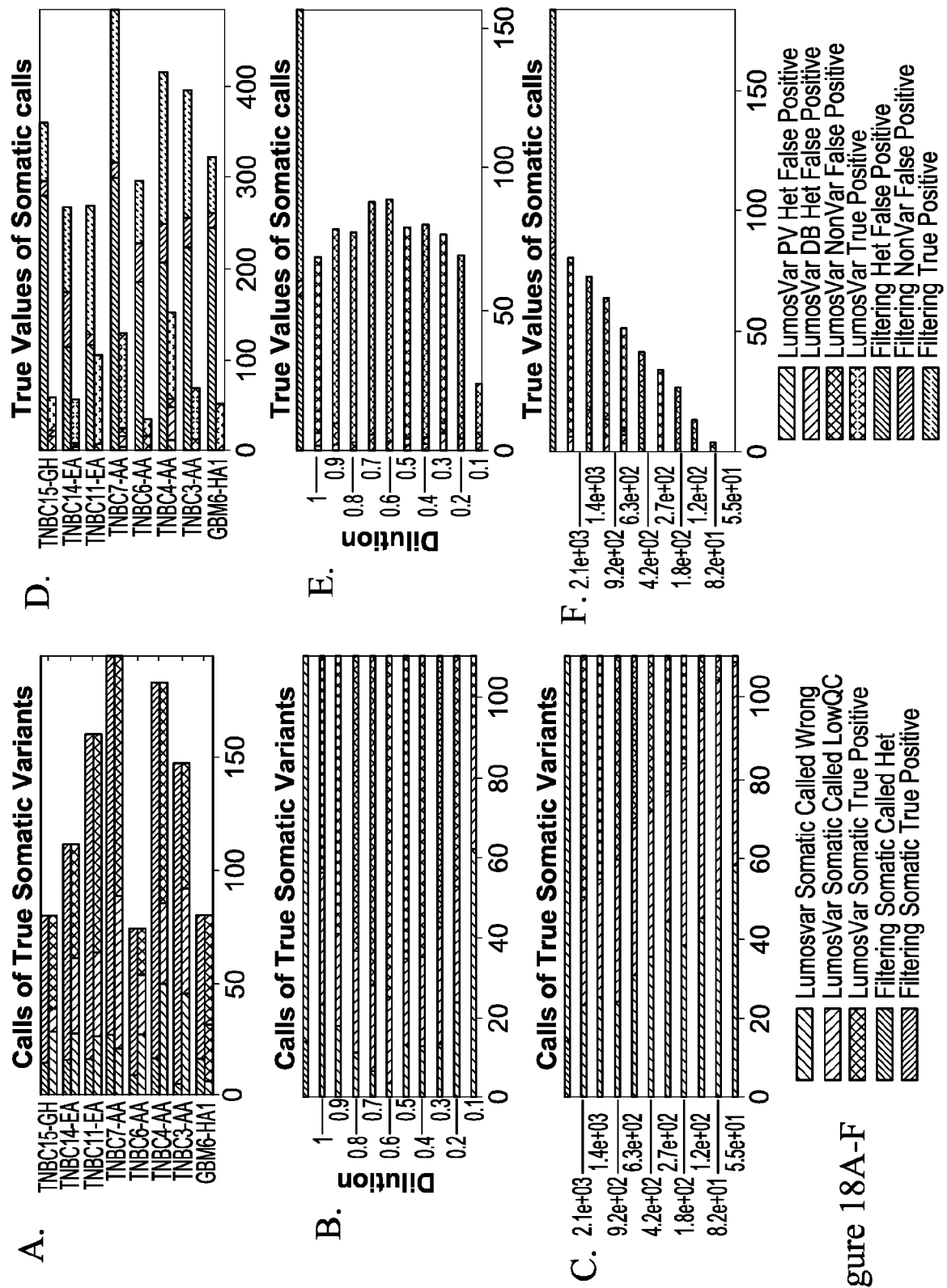
Figure 18A-F

G.

| | TumorOnly_Somatic Called Wrong | TumorOnly_Somatic Called LowQC | TumorOnly_Somatic True Positive | TumorOnly_PV Het False Positive | TumorOnly_DB Het False Positive | TumorOnly_NonVar False Positive |
|---|---|---|---|---|---|---|
| coverage_2102 | 23 | 27 | 61 | 2 | 4 | 14 |
| coverage_55 | 58 | 51 | 0 | 0 | 0 | 0 |
| coverage_82 | 50 | 55 | 4 | 0 | 0 | 0 |
| coverage_122 | 45 | 52 | 13 | 0 | 1 | 0 |
| coverage_185 | 38 | 46 | 26 | 0 | 0 | 1 |
| coverage_273 | 44 | 33 | 34 | 0 | 0 | 1 |
| coverage_420 | 35 | 37 | 39 | 0 | 1 | 2 |
| coverage_630 | 31 | 38 | 42 | 3 | 4 | 3 |
| coverage_925 | 24 | 36 | 51 | 2 | 5 | 7 |
| coverage_1408 | 25 | 30 | 56 | 3 | 4 | 10 |
| dilution_10 | 62 | 31 | 18 | 1 | 2 | 4 |
| dilution_20 | 24 | 29 | 58 | 0 | 5 | 7 |
| dilution_30 | 13 | 30 | 68 | 1 | 7 | 1 |
| dilution_40 | 13 | 22 | 76 | 0 | 3 | 2 |
| dilution_50 | 13 | 22 | 76 | 1 | 2 | 1 |
| dilution_60 | 4 | 21 | 86 | 1 | 0 | 3 |
| dilution_70 | 7 | 21 | 83 | 0 | 0 | 6 |
| dilution_80 | 11 | 26 | 74 | 0 | 0 | 4 |
| dilution_90 | 18 | 23 | 70 | 1 | 1 | 8 |
| dilution_100 | 23 | 33 | 55 | 2 | 5 | 7 |
| GBM6-HA | 7 | 26 | 48 | 3 | 0 | 2 |
| TNBC3-AA | 46 | 46 | 56 | 1 | 11 | 2 |
| TNBC4-AA | 50 | 36 | 98 | 13 | 39 | 4 |
| TNBC6-AA | 27 | 27 | 21 | 3 | 12 | 2 |
| TNBC7-AA | 22 | 67 | 107 | 6 | 12 | 7 |
| TNBC11-EA | 26 | 38 | 97 | 2 | 6 | 1 |
| TNBC14-EA | 29 | 33 | 50 | 1 | 4 | 4 |
| TNBC15-GH | 29 | 11 | 41 | 3 | 15 | 2 |

| | Filtering_Somatic_Called_Het | Filtering_Somatic_True_Positive | Filtering_Het_False_Positive | Filtering_NonVar_False_Positive |
|---|---|---|---|---|
| GBM6-HA | 18 | 63 | 244 | 15 |
| TNBC3-AA | 6 | 142 | 223 | 31 |
| TNBC4-AA | 18 | 166 | 209 | 41 |
| TNBC6-AA | 10 | 65 | 186 | 45 |
| TNBC7-AA | 28 | 168 | 298 | 18 |
| TNBC11-EA | 17 | 144 | 118 | 9 |
| TNBC14-EA | 16 | 96 | 116 | 58 |
| TNBC15-GH | 15 | 66 | 280 | 14 |

Figure 18H

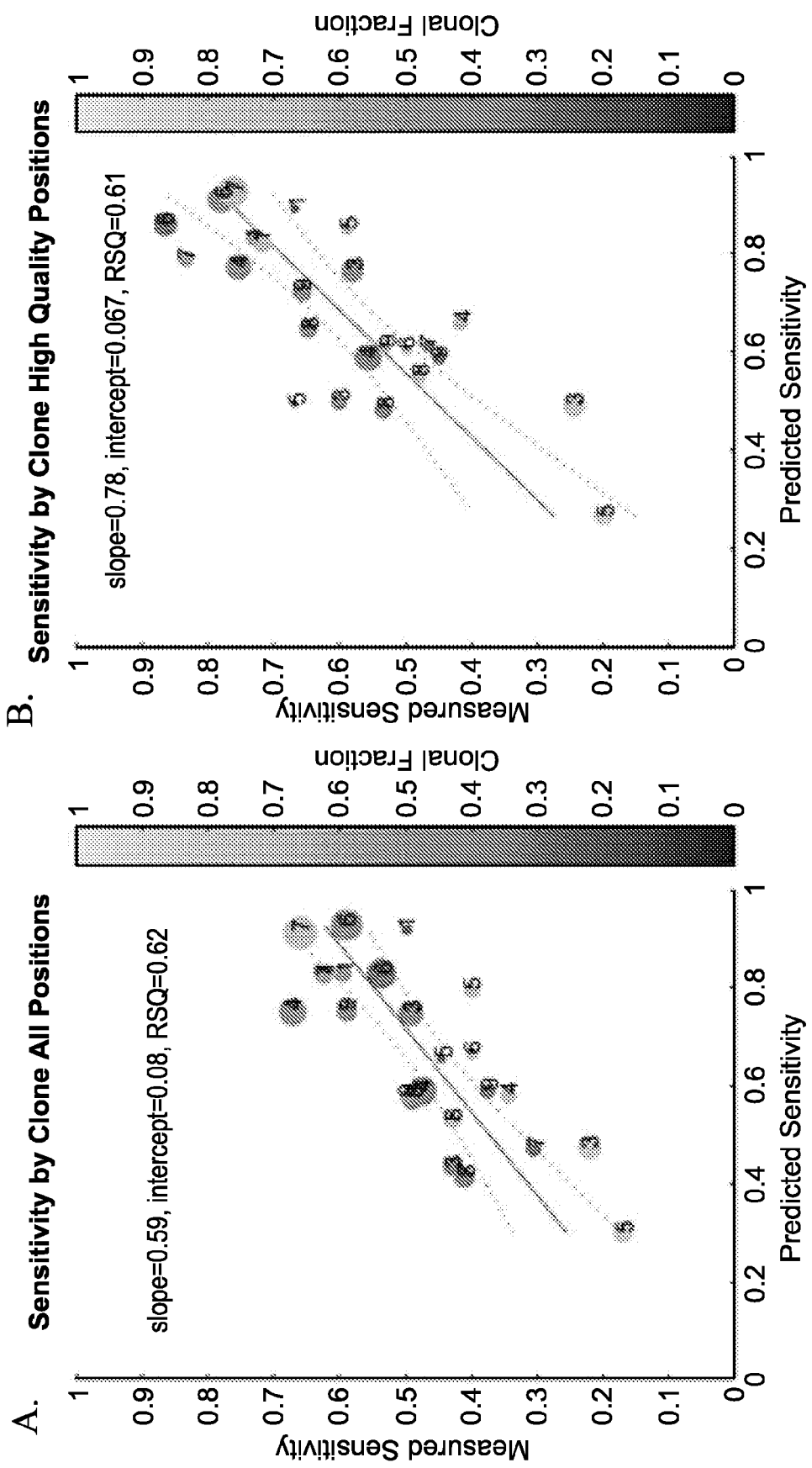
Figure 19A-B

C.

| perCN | meanPower all positions | FCcount | meanPower high quality only | TPcount | FPcount | FNcount | measured sensitivity all positions | measured sensitivity high quality only |
|---|---|---|---|---|---|---|---|---|
| 0.60 | 0.92 | 3 | 0.89 | 6 | 1 | 6 | 0.50 | 0.67 |
| 0.34 | 0.83 | 7 | 0.83 | 19 | 2 | 13 | 0.59 | 0.73 |
| 0.06 | 0.83 | 9 | 0.82 | 23 | 2 | 14 | 0.62 | 0.72 |
| 0.61 | 0.43 | 10 | 0.50 | 15 | 5 | 20 | 0.43 | 0.60 |
| 0.39 | 0.75 | 21 | 0.77 | 29 | 2 | 30 | 0.49 | 0.58 |
| 0.00 | 0.47 | 37 | 0.49 | 12 | 7 | 42 | 0.22 | 0.24 |
| 0.43 | 0.59 | 31 | 0.59 | 39 | 8 | 43 | 0.48 | 0.56 |
| 0.52 | 0.75 | 16 | 0.77 | 49 | 5 | 24 | 0.67 | 0.75 |
| 0.05 | 0.58 | 14 | 0.66 | 10 | 43 | 19 | 0.34 | 0.42 |
| 0.35 | 0.66 | 2 | 0.50 | 4 | 3 | 5 | 0.44 | 0.67 |
| 0.10 | 0.79 | 7 | 0.85 | 10 | 10 | 15 | 0.40 | 0.59 |
| 0.55 | 0.30 | 28 | 0.27 | 7 | 4 | 34 | 0.17 | 0.20 |
| 0.61 | 0.83 | 7 | 0.86 | 45 | 10 | 39 | 0.54 | 0.87 |
| 0.35 | 0.93 | 16 | 0.91 | 56 | 9 | 39 | 0.59 | 0.78 |
| 0.04 | 0.66 | 6 | 0.61 | 6 | 6 | 9 | 0.40 | 0.50 |
| 0.26 | 0.47 | 8 | 0.61 | 7 | 2 | 16 | 0.30 | 0.47 |
| 0.46 | 0.82 | 4 | 0.79 | 20 | 4 | 12 | 0.63 | 0.83 |
| 0.27 | 0.91 | 22 | 0.93 | 70 | 3 | 36 | 0.66 | 0.76 |
| 0.50 | 0.41 | 14 | 0.49 | 16 | 3 | 23 | 0.41 | 0.53 |
| 0.44 | 0.57 | 12 | 0.65 | 22 | 3 | 23 | 0.49 | 0.65 |
| 0.06 | 0.53 | 13 | 0.55 | 12 | 3 | 16 | 0.43 | 0.48 |
| 0.24 | 0.59 | 11 | 0.59 | 9 | 3 | 15 | 0.38 | 0.45 |
| 0.53 | 0.75 | 12 | 0.72 | 23 | 8 | 16 | 0.59 | 0.66 |
| 0.22 | 0.58 | 8 | 0.61 | 9 | 9 | 9 | 0.50 | 0.53 |

| TumorPurity 1 | TumorPurity 2 | TumorPurity merged | N1M0 joint | N1M0 merged | N2M0 joint | N2M0 merged | N2M1 joint | N2M1 merged | N3M0 joint | N3M0 merged | N3M1 joint | N3M1 merged | N4M2 joint | N4M2 merged |
|---|---|---|---|---|---|---|---|---|---|---|---|---|---|---|
| 0.05 | 0.2 | 0.125 | 400 | 800 | 200 | 400 | 800 | 800 | 200 | 200 | 200 | 400 | 200 | 400 |
| 0.05 | 0.35 | 0.2 | 200 | 400 | 200 | 200 | 400 | 400 | 100 | 800 | 200 | 200 | 200 | 200 |
| 0.05 | 0.5 | 0.275 | 200 | 200 | 100 | 800 | 200 | 200 | 100 | 3200 | 100 | 200 | 100 | 200 |
| 0.05 | 0.65 | 0.35 | 100 | 800 | 50 | 3200 | 200 | 200 | 50 | 800 | 100 | 400 | 100 | 200 |
| 0.05 | 0.8 | 0.425 | 50 | 3200 | 50 | 400 | 100 | 200 | 50 | 200 | 100 | 800 | 100 | 200 |
| 0.05 | 0.95 | 0.5 | 50 | 3200 | 50 | 100 | 100 | 200 | 50 | 100 | 50 | 3200 | 200 | 200 |
| 0.2 | 0.35 | 0.275 | 200 | 200 | 400 | 800 | 200 | 400 | 400 | 3200 | 200 | 200 | 200 | 200 |
| 0.2 | 0.5 | 0.35 | 200 | 400 | 200 | 3200 | 200 | 200 | 100 | 400 | 200 | 400 | 200 | 200 |
| 0.2 | 0.65 | 0.425 | 100 | 3200 | 100 | 400 | 200 | 200 | 100 | 200 | 200 | 1600 | 200 | 200 |
| 0.2 | 0.8 | 0.5 | 50 | 3200 | 100 | 200 | 200 | 200 | 100 | 100 | 200 | 3200 | 200 | 400 |
| 0.2 | 0.95 | 0.575 | 100 | 400 | 100 | 200 | 100 | 200 | 100 | 100 | 100 | 3200 | 200 | 400 |
| 0.35 | 0.5 | 0.425 | 400 | 800 | 200 | 400 | 200 | 200 | 200 | 200 | 800 | 1600 | 200 | 200 |
| 0.35 | 0.65 | 0.5 | 200 | 3200 | 100 | 200 | 200 | 200 | 200 | 200 | 800 | 3200 | 400 | 400 |
| 0.35 | 0.8 | 0.575 | 100 | 400 | 100 | 200 | 200 | 400 | 200 | 200 | 200 | 3200 | 400 | 400 |
| 0.35 | 0.95 | 0.65 | 100 | 200 | 200 | 200 | 200 | 200 | 200 | 200 | 200 | 1600 | 400 | 800 |
| 0.5 | 0.65 | 0.575 | 400 | 800 | 200 | 200 | 400 | 400 | 200 | 200 | 1600 | 3200 | 800 | 800 |
| 0.5 | 0.8 | 0.65 | 100 | 200 | 200 | 200 | 400 | 400 | 400 | 400 | 400 | 800 | 800 | 800 |
| 0.5 | 0.95 | 0.725 | 100 | 400 | 200 | 200 | 800 | 800 | 400 | 400 | 400 | 800 | 800 | 1600 |
| 0.65 | 0.8 | 0.725 | 200 | 200 | 400 | 400 | 800 | 800 | 400 | 400 | 800 | 800 | 800 | 1600 |
| 0.65 | 0.95 | 0.8 | 200 | 400 | 400 | 400 | 800 | 1600 | 800 | 800 | 800 | 1600 | 1600 | 1600 |
| 0.8 | 0.95 | 0.875 | 400 | 400 | 800 | 800 | 3200 | 3200 | 800 | 800 | 3200 | 3200 | 3200 | 3200 |

Figure 21B

| Patient ID | Mean Target Coverage | | % Tumor | |
|---|---|---|---|---|
| | NE | CE | NE | CE |
| GBM-003 | 183 | 387 | 25 | 81 |
| GBM-005 | 482 | 404 | 0 | 41 |
| GBM-006 | 441 | 248 | 0 | 62 |
| GBM-008 | 203 | 424 | 2 | 71 |
| GBM-009 | 199 | 387 | 20 | 73 |
| GBM-014 | 223 | 366 | 40 | 88 |
| GBM-016 | 416 | 376 | 17 | 83 |

| typeCat | LumosVar Somatic True Positive | LumosVar PV Het False Positive | LumosVar DB Het False Positive | LumosVar NonVar False Positive | LumosVar Somatic Called Wrong | LumosVar Somatic Called LowQC | Filtering True Positive | Filtering Het False Positive | Filtering NonVar False Positive | Filtering Somatic Called Het |
|---|---|---|---|---|---|---|---|---|---|---|
| SNV UTR | 4 | 2 | 0 | 0 | 3 | 3 | 14 | 32 | 9 | 0 |
| SNV nonsynonymous | 201 | 6 | 35 | 10 | 83 | 42 | 308 | 343 | 44 | 52 |
| SNV other noncoding | 186 | 17 | 38 | 6 | 97 | 61 | 371 | 979 | 127 | 32 |
| SNV splice related | 23 | 1 | 0 | 2 | 8 | 5 | 38 | 35 | 4 | 4 |
| SNV start/stop altered | 13 | 0 | 0 | 2 | 10 | 1 | 24 | 14 | 7 | 3 |
| SNV synonymous | 69 | 4 | 22 | 4 | 22 | 19 | 103 | 153 | 21 | 35 |
| indel UTR | 0 | 1 | 0 | 0 | 1 | 0 | 1 | 4 | 0 | 0 |
| indel codon(s) altered | 4 | 0 | 0 | 4 | 1 | 1 | 9 | 6 | 5 | 0 |
| indel frameshift | 10 | 0 | 0 | 6 | 2 | 3 | 17 | 11 | 4 | 1 |
| indel other noncoding | 7 | 1 | 4 | 24 | 8 | 5 | 23 | 94 | 10 | 1 |
| indel splice related | 1 | 0 | 0 | 2 | 2 | 0 | 3 | 3 | 1 | 0 |
| indel start/stop altered | 0 | 0 | 0 | 0 | 0 | 0 | 0 | 0 | 0 | 0 |

Figure 23B

| Patient | Gene | AA Change | AD AN (AF) | AD TM (AF) | LV | ANR | Level | Cosmic |
|---|---|---|---|---|---|---|---|---|
| BHH06 | AKT1 | E17K | 121,23 (0.16) | 151,62 (0.29) | Yes | No | 3 | 287 |
| BHH24 | AKT1 | E17K | 123,1 (0.01) | 118,60 (0.34) | Yes | Yes | 3 | 287 |
| BHH01 | PIK3CA | H1047R | 473,9 (0.02) | 378,201 (0.35) | Yes | No | 3 | 1717 |
| BHH28 | PIK3CA | H1047L | 417,0 (0) | 348,81 (0.19) | Yes | Yes | 3 | 1717 |
| BHH18 | PIK3CA | G106R | 127,8 (0.06) | 96,19 (0.17) | Yes | No | 3 | 3 |
| BHH18 | PIK3CA | Q546E | 201,16 (0.07) | 164,38 (0.19) | Yes | No | 3 | 2 |
| HHP13 | PIK3CA | E545K | 332,0 (0) | 195,11 (0.05) | No | Yes | 3 | 261 |
| HHP19 | TP53 | G245S | 186,1 (0.01) | 61,76 (0.55) | Yes | Yes | 3 | 43 |
| BHH25 | PIK3CA | E726K | 269,0 (0) | 268,17 (0.06) | No | Yes | 2 | 25 |
| BHH25 | SF3B1 | K666E | 210,0 (0) | 122,46 (0.27) | Yes | Yes | 2 | 18 |

Figure 26

METHODS OF DETECTING SOMATIC AND GERMLINE VARIANTS IN IMPURE TUMORS

CROSS-REFERENCE TO RELATED APPLICATIONS

This application is the U.S. National Stage of International Application No. PCT/US2018/016522, filed on Feb. 1, 2018, which claims the benefit of U.S. Provisional Patent Application No. 62/453,492, filed on Feb. 1, 2017, the contents of each of which are incorporated herein by reference in their entireties.

TECHNICAL FIELD

This disclosure relates generally to sequencing data processing and benchmarking, and in particular, to detecting somatic and germline variants in tumor samples.

BACKGROUND

Somatic mutations often drive cancer initiation and progression[1]. Some known cancer driver events may be targetable with specific drugs. Some known cancer driver events may have prognostic value for the patient. Some somatic variants may indicate an unfavorable response or resistance to drugs or therapies. Discovery of novel cancer drivers could enable scientists to develop models of the cancer driver (cell lines, animal) to better understand its mechanism and discover existing or new drugs that are able to target tumors with that driver. Detection of somatic variants could be used to develop personalized assays to monitor the patient for response to therapy and recurrence.

The identification of somatic mutations through next generation sequencing has enabled the identification of cancer driver events in individual patient tumor samples[2-4]. There is also ongoing effort to discover new cancer driver mutations, particularly in non-coding regions[5]. Although sequencing of tumor-associated cancer gene panels and exomes is starting to be adopted in clinical practice to personalize therapy, there is much to learn about how mutation status correlates with response to therapy. Archival tissue collections represent a rich resource for identifying new driver mutations and clarifying how genomic features relate to clinical outcomes[6,7]. However, most archival collections do not contain blood samples or other normal tissue from sites distant to the tumor. Without a normal tissue sample for comparison, it is difficult to determine which variants are somatic and which are germline[8]. Innovative approaches are needed to identify somatic variants when normal tissue is not available.

Often, histologically normal tissue is available from the tumor sample. For instance, surgeons typically remove a margin of adjacent normal tissue when resecting a tumor, and this normal tissue can undergo DNA sequencing to identify germline variants. However, it is difficult to know if the adjacent normal tissue is truly free of infiltrating tumor cells. Contamination of the adjacent normal tissue with the tumor tissue during processing could also confound interpretation of the results[9]. Also, even without infiltrating tumor cells, the adjacent tissue may contain somatic mutations. Field cancerization, where molecular alterations are observed in tissue adjacent to the overt cancer, is thought to be an important risk factor for multifocal and recurrent disease[10]. This phenomenon has been observed in many cancer types including breast[11] and prostate[12]. Even healthy individuals have somatic mutations in normal tissues, and the mutation patterns tend to be similar to those of the cancers arising from that tissue type[13]. There even appears to be positive selection for cancer driver mutations in normal skin[14]. Therefore, it is important to consider potential sources of somatic variant contamination when normal tumor-adjacent tissue is used to identify tumor specific somatic variants.

When tumor-only sequencing data is available, researchers have developed various analytic strategies to distinguish germline and somatic variants. One first step to identifying somatic variants in tumor-only sequencing data is to filter out the germline variants found in population databases. Jones et al., however, showed that filtering alone is not sufficient, as each individual typically has an average of 249 private germline variants not found in the population databases that would be incorrectly classified as somatic in tumor-only sequencing[8]. The number of private germline variants will vary based on the individuals' ancestry. The private variant rate in a population depends both on how well represented the population is in large scale sequencing projects, as well has the extent to which the population has undergone a recent expansion adding to the diversity of variants[15]. More recently, Kalatskaya et al. published a machine-learning approach (ISOWN) to classify somatic and germline variants from tumor-only sequencing data[50]. The ISOWN requires a large training set, and performs best when the training and test datasets are from the same cancer type and patient cohort. In the case of rare cancer types and N of one study, obtaining such training sets may not be practical. The variant allele fraction, which is the fraction of reads supporting a the mutated allele at a given locus, can also help to distinguish somatic from germline variants in impure tumors; the somatic variants should only be present in the tumor cells, leading to a low variant allele fraction, while the germline variants would be present in both the tumor and normal cells in the sample, leading to a variant allele fraction close to 0.5 for heterozygous variants. However, copy number alterations in the tumor can shift both the somatic and germline variant allele fractions, which can lead to considerable overlap in the expected somatic and germline variant allele fractions and greatly reduce the power to detect somatic variants. Thus, there is a need for new bioinformatics methods to call germline and somatic variants from tumor samples with high and predictable specificity.

BRIEF SUMMARY OF THE INVENTION

The present invention is directed to a method of detecting one or more somatic tumor variants and/or germline variants from one or more tumor samples from a subject, comprising: a) receiving an aligned sequence data from the one or more tumor samples; b) identifying a candidate variant within the aligned sequence data; c) observing an allelic fraction of the candidate variant in each of the one or more tumor samples; d) modeling to find a copy number state estimate of the candidate variant and a tumor-cell fraction of each of the one or more tumor samples; e) predicting an expected allelic fraction of the candidate variant by assuming a somatic or a germline status; and f) determining whether each candidate variant is a somatic variant or a germline variant by comparing the observed allelic fraction to the expected allelic fraction.

In certain aspects, the one or more tumor samples are archival samples. The archival samples may be formalin fixed paraffin embedded (FFPE) samples. In one embodiment, the one or more tumor samples have no matched normal, non-tumor sample. In another embodiment, the one or more tumor samples have a matched normal sample. The matched normal sample may be derived from tissue adjacent to the tumor.

In yet other aspects, the disclosed method further comprises: identifying two or more sample regions having different tumor contents; and macro-dissecting to separate the two or more sample regions. In one aspect, the one or more tumor samples contain normal, non-tumor cells. In some aspects, at least 5% of the cells in the one or more tumor samples are normal, non-tumor cells.

In some embodiments, the sequencing data comprises DNA sequencing data. In one aspect, the candidate variant is a single-nucleotide variant (SNV). In another aspect, the candidate variant is an insertion or a deletion (INDEL). The variant may be a noncoding mutation. In some embodiments, the variant is rare within a population of the subject.

In yet other embodiments, the number of the tumor samples is two or more, and the copy number state estimates of the variants and the tumor-cell fractions of the variants in the tumor samples are modeled jointly. In one aspect, the disclosed methods further comprise verifying the somatic or germline status. The germline status may be verified using one or more germline variant callers. Germline variant callers include HAPLOTYPE CALLER, samtools, and/or freebayes. In other aspects, the somatic status is verified using one or more somatic variant callers. Somatic variant callers include SEURAT, STRELKA, and/or MUTECT.

The present invention also relates to a method of detecting a somatic tumor variant and/or a germline variant from a tumor sample of a subject, comprising: a) receiving an aligned sequence data from the tumor sample; b) identifying a candidate variant within the aligned sequence data; c) partitioning the genome into segments, wherein each segment contains at most one copy number alteration; d) observing an allelic fraction of the candidate variant of each segment; e) modeling to find a copy number state estimate of the segments and a tumor-cell fraction of main and subclonal variant groups; f) determining an expected allelic fraction of the candidate germline variant or the candidate somatic variant; g) determining a posterior probability that a candidate variant is somatic, germline heterozygous, or homozygous using a Bayesian model; and h) repeating steps e) through g) until the result converges.

In certain aspects, the step of partitioning the genome into segments is performed on the ratio of the tumor to the normal mean exon read depth using the circular binary segmentation. In one aspect, the disclosed methods further comprise an initial classification step, wherein the candidate variant is classified as somatic or germline based on database frequencies. In one embodiment, the step of determining the expected allelic fractions of germline and somatic variants further comprises: estimating allele-specific copy number of clonal and sub-clonal copy number events; and estimating the sample fraction of the main clonal and sub-clonal populations.

In yet other aspects, the modeling step uses an expectation maximization approach that maximizes the sum of likelihoods of two or more data measurements. In one aspect, the two or more data measurements are selected from the group consisting of: the exon read depth; the heterozygous variant minor allele read depth; the somatic variant minor allele read depth; the number of heterozygous positions detected in each segment; and the number of somatic calls in known germline variant positions. In another aspect, the data measurements consist of: the exon read depth; the heterozygous variant minor allele read depth; the somatic variant minor allele read depth; the number of heterozygous positions detected in each segment; and the number of somatic calls in known germline variant positions. In yet another aspect, the data measurements comprise: the exon read depth; the heterozygous variant minor allele read depth; the somatic variant minor allele read depth; the number of heterozygous positions detected in each segment; and the number of somatic calls in known germline variant positions.

In some embodiments, the likelihood of the exon read depth is modeled as a Poisson distribution with a mean calculated based on the observed exon read depths in the unmatched control samples. In other embodiments, the likelihood of the heterozygous position minor allele read counts are modeled as a beta-binomial distribution with an expected allelic fraction of a germline variant. In yet other embodiments, the likelihood of the somatic position minor allele read counts are modeled as a beta-binomial distribution with an expected allelic fraction of a somatic variant. In a particular embodiment, the posterior probability is calculated based on a prior probability of a somatic mutation and the prior probability of the germline genotypes.

In certain aspects, the disclosed methods further comprise: applying a classifier to determine if the candidate variant is a true variant or an artifact. In other aspects, the disclosed methods further comprise: building a classifier to determine if the candidate variant is a true variant or an artifact. In one aspect, building the classifier comprises: a) selecting one or more quality metrics; b) assigning a Pass threshold and a Reject threshold to each selected quality metric; c) identifying candidate variants from the tumor sample; d) calculating the selected quality metrics for each candidate variant; e) assigning a candidate variant to a Pass training group if the candidate variant passes one or more Pass thresholds; and f) assigning a candidate variant to a Reject training group if the candidate variant passes one or more Reject thresholds.

In some embodiments, a candidate variant passing at least half of the Pass thresholds is assigned to the Pass training group. In one embodiment, a candidate variant passing all of the Pass thresholds is assigned to the Pass training group. In another embodiment, a candidate variant passing no more than half of the Reject thresholds is assigned to the Reject training group. In yet another embodiment, a candidate variant passing one Reject threshold is assigned to the Reject training group.

In some aspects, the classifier is a machine learning algorithm. In one aspect, the classifier is built specifically for SNVs. In another aspect, the classifier is built specifically for INDELs. In one aspect, applying the classifier comprises fitting a quadratic discriminant model to the variant.

In some embodiments, the classifier is built after determining the somatic or germline status of the candidate variant. In one embodiment, the classifier is applied after determining a somatic or germline status of the candidate variant.

The present invention also relates to a method of building a classifier for distinguishing between a true variant from an artifact in a tumor sample from a subject, comprising: a) selecting one or more quality metrics; b) assigning a Pass threshold and a Reject threshold to each selected quality metric; c) identifying candidate variants from the tumor sample; d) calculating the selected quality metrics for each candidate variant; e) assigning a candidate variant to a Pass training group if the candidate variant passes one or more Pass thresholds; and f) assigning a candidate variant to a Reject training group if the candidate variant passes one or more Reject thresholds.

In certain aspects, at least one of the one or more quality metrics is selected from the group consisting of: percentage of bases having minimum base quality, percentage of bases supporting the major or minor allele, the minimum percentage of reads from forward or reverse strand, minimum average mapping quality of reads supporting the major or minor allele, minimum average base quality of bases supporting the major or minor allele, maximum average percentage of mismatches in reads supporting the major and minor alleles, minimum average distance from either end of sequence of the major or minor allele, difference in average percentage of forward strand between the major and minor alleles, difference in average base quality between the major and minor alleles, difference in average mapping quality between the major and minor alleles, difference in average percentage of mismatches between the major and minor alleles, difference in average read position between the major and minor alleles, quality score of position from unmatched controls, and mean quality score in region.

In other aspects, the one or more quality metrics comprise: percentage of bases having minimum base quality, percentage of bases supporting the major or minor allele, the minimum percentage of reads from forward or reverse strand, minimum average mapping quality of reads supporting the major or minor allele, minimum average base quality of bases supporting the major or minor allele, maximum average percentage of mismatches in reads supporting the major and minor alleles, minimum average distance from either end of sequence of the major or minor allele, difference in average percentage of forward strand between the major and minor alleles, difference in average base quality between the major and minor alleles, difference in average mapping quality between the major and minor alleles, difference in average percentage of mismatches between the major and minor alleles, difference in average read position between the major and minor alleles, quality score of position from unmatched controls, and mean quality score in region.

In yet other aspects, the one or more quality metrics consist of: percentage of bases having minimum base quality, percentage of bases supporting the major or minor allele, the minimum percentage of reads from forward or reverse strand, minimum average mapping quality of reads supporting the major or minor allele, minimum average base quality of bases supporting the major or minor allele, maximum average percentage of mismatches in reads supporting the major and minor alleles, minimum average distance from either end of sequence of the major or minor allele, difference in average percentage of forward strand between the major and minor alleles, difference in average base quality between the major and minor alleles, difference in average mapping quality between the major and minor alleles, difference in average percentage of mismatches between the major and minor alleles, difference in average read position between the major and minor alleles, quality score of position from unmatched controls, and mean quality score in region.

In one embodiment, a candidate variant passing at least half of the Pass thresholds is assigned to the Pass training group. In another embodiment, a candidate variant passing all of the Pass thresholds is assigned to the Pass training group. In yet another embodiment, a candidate variant passing no more than half of the Reject thresholds is assigned to the Reject training group. In some aspects, a candidate variant passing one Reject threshold is assigned to the Reject training group.

In some aspects, the classifier is a machine learning algorithm. In other aspects, the classifier is built specifically for SNVs. In yet other aspects, the classifier is built specifically for INDELs.

In some embodiments, the subject is a mammal. In one embodiment, the mammal is selected from a group comprising: human, mouse, rat, guinea pig, dog, cat, horse, cow, pig, and non-human primate. In a particular embodiment, the mammal is a human.

BRIEF DESCRIPTION OF THE DRAWINGS

FIGS. 1A-1C Performance by Variant Type. (FIG. 1A) The calls of LumosVar (bottom bar in pair) compared to filtering approach (top bar in pair) in calling true somatic variants. The size of the yellow portions of the bars indicate the number of true somatic variants falsely called germline heterozygotes or homozygous, the grey represents true somatic variants that were filtered on quality or not detected as variants, and the blue represents true positive somatic calls. (FIG. 1B) The number of somatic calls by the LumosVar (bottom bar in pair) compared to the filtering approach (top bar in pair) that are truly germline private heterozygous (red), germline heterozygous database variants (pink), homozygous (grey) or truly somatic (blue). FIGS. 1A and 1B show that proportion of false positives in the filtering approach is much higher in non-coding variants than other variant types. (FIG. 1C) The data in (FIGS. 1A and 1B) presented in a table format.

FIG. 2 Description of the patient samples and sequencing metrics of the patients used in the evaluation dataset. Note that GBM1-EA was sequenced to higher mean target coverage for in-silico dilution and down-sampling experiments. Blood samples from each patient were also sequenced to establish true variant classification.

FIG. 3 The criteria for counting a variant as a true variant. Germline variants were called by multiple germline callers (e.g., Haplotype Caller, Samtools, and Freebayes). Somatic variants were called by multiple somatic callers (e.g., Mutect, Seurat, and Strelka).

FIG. 6 Model input parameters for the single-sample approach (LumosVar).

FIG. 7 Filtering Metrics. The criteria used to initially classify a variant in the training set for the quadratic discriminant model.

FIG. 8 Key notations (parameters and variables) used in the model.

FIGS. 9A and 9B One thousand Genomes Population Codes. Abbreviations used to describe the populations from the 1000 Genomes Project. (FIG. 9A) 1000 Genomes Population Codes. (FIG. 9B) 1000 Genomes Super Population Codes.

FIGS. 10A-10C Correlation between ancestry and the effectiveness of using database filters to identify somatic variants. (FIG. 10A) The distribution and number of variants unique to an individual across 2,503 individuals from Phase 3 of 1000 Genomes plotted as violin plot for each of 26 different populations (indicated by their three-letter code) and colored based on their ancestral super population. (FIG.

10B) The number of private variants for 150 individuals after filtering through 1000 Genomes, The Exome Aggregation Consortium (ExAC), not previously sequenced shown by their principle components of common variation (>1%) is shown as a color-metric bubble chart. (FIG. 10C) The distribution of variants within the groups within FIG. 10C, correlating to FIG. 10B, where individuals clustering near those of European, Asian, and African Ancestry.

(FIGS. 11A-11L) Example copy number plots for three conditions: with high tumor content and moderate coverage (FIGS. 11A-11D), with high tumor content and high coverage (FIGS. 11E-11H), and with moderate tumor content and moderate coverage (FIGS. 11I-11L). A one-copy loss (the line on the right half of each panel) is detected in the segment (indicated by arrow head). (FIGS. 11B-11C, 11F-11G, 11J-11K) The expected somatic and germline allelic fractions: germline variants (grey and "g"), somatic main clone (blue and "sm"), and somatic sub-clones (green, red, and "ss") for diploid regions (FIGS. 11B, 11, 11J) and one-copy loss regions (FIGS. 11C, 11G, 11K). In high tumor content and moderate coverage, the main clone distribution overlaps with the germline and is difficult to detect in the diploid region, while the red sub-clone is more difficult to detect in the one copy loss region. Increasing the coverage increases the sharpness of the distributions making the somatic variants easier to detect. In the moderate tumor content sample, all clones are easy to differentiate from germline in the diploid region, but the main clone is hard to detect in the one copy loss region. Using these distributions to calculate conditional probabilities, as well as using 1000 genomes population frequencies and COSMIC mutation counts to calculate prior probabilities, somatic and germline variants can be called. (FIGS. 11D, 11H, 11L) The allelic fractions of germline and somatic variants colored by a clone. A plus sign indicates a variant and an open circle indicates a false positive. With high tumor content, variants in the main clone are detected better in the deleted region under moderate coverage condition. The number of variants detected increases in the high coverage condition.

FIGS. 18G-18H Compares calls of true somatic variants and true values of variants called somatic. (FIGS. 18A-18C) the number of calls made by the LumosVar (bottom bars) versus the filtering approach (top bars) in calling true somatic variants. The yellow portions represent true somatic variants falsely called germline heterozygotes or homozygous. The grey portions represent true somatic variants that were filtered on quality or not detected as variants. The blue portions represent true positive somatic calls. The filtering approach has better sensitivity (mean TPR 87%, range 78-96%) compared to the tumor only caller (mean TPR 52%, range 27-62%). (FIGS. 18D-18F) The number of somatic calls by the LumosVar (bottom bars) versus the filtering approach (top bars) that are truly somatic (blue) or germline private heterozygous variants (red), germline heterozygous database variants (pink), or germline homozygous variants (grey). The tumor-only caller has better precision (mean PPV 75%, range 56-89%) relative to the filtering approach (mean PPV 35%, range 19-55%). (FIGS. 18G-18H) The data in (FIGS. 18A-18F) presented in a table format.

FIGS. 19A-19C Simulations were used to predict the power to detect each true somatic variant assuming the sample fraction and copy number were correctly called. For each clone and each sample, the true positive rate is plotted against the power predicted from the simulations. The size of the bubble is proportional to the number of true positive variants in each clone, the color the points represents the sample fraction of the clone, and the number indicates the sample number. The highest sample fraction clone has the worse predicted and observed sensitivity. (FIG. 19A) All of the true somatic variants. (FIG. 19B) Only includes those that pass the quality filters. FIGS. 19A-19B show that the predicted power correlates well with the measured sensitivity, particularly when the low quality variants are excluded. (FIG. 19C) The data in (FIGS. 19A-19B) presented in a table format.

FIGS. 21A and 21B Allele Frequencies of Somatic and Germline Variants and Required Coverage for (FIG. 21A) Somatic Variant Detection by Simulation: Comparing the Single-Sample and Joint Approach. The top set of graphs shows the expected allele frequency of somatic (blue) and germline variants (red) by tumor content (x-axis) for different copy number states. The bottom set of graphs shows the coverage required to detect at least 80% of the simulated somatic variants using two samples of different tumor content (shown on the x and y-axis) using a joint approach (lower right triangle of each heatmap) or using a single-sample approach on a merged sample with a tumor content that is the average of the two samples and coverage that is the sum of the two samples (upper left triangle of heatmap). The color indicates the minimum coverage corresponding to the mean target coverage in the single sample approach, or the sum of the mean target coverage in the two-sample joint approach. White squares indicate that less than 80% of the somatic variants were detected at the highest coverage simulated (3200×). (FIG. 21B) The heatmap in a table form.

FIG. 22 Characteristics of the evaluation dataset.

FIGS. 23 and 23B Comparison of Filtering, Pooled, and Joint Approach. (FIG. 23B) The data in (FIG. 23A) presented in a table format.

FIG. 26 Hotspot mutation detection.

DETAILED DESCRIPTION

Figure 1A:
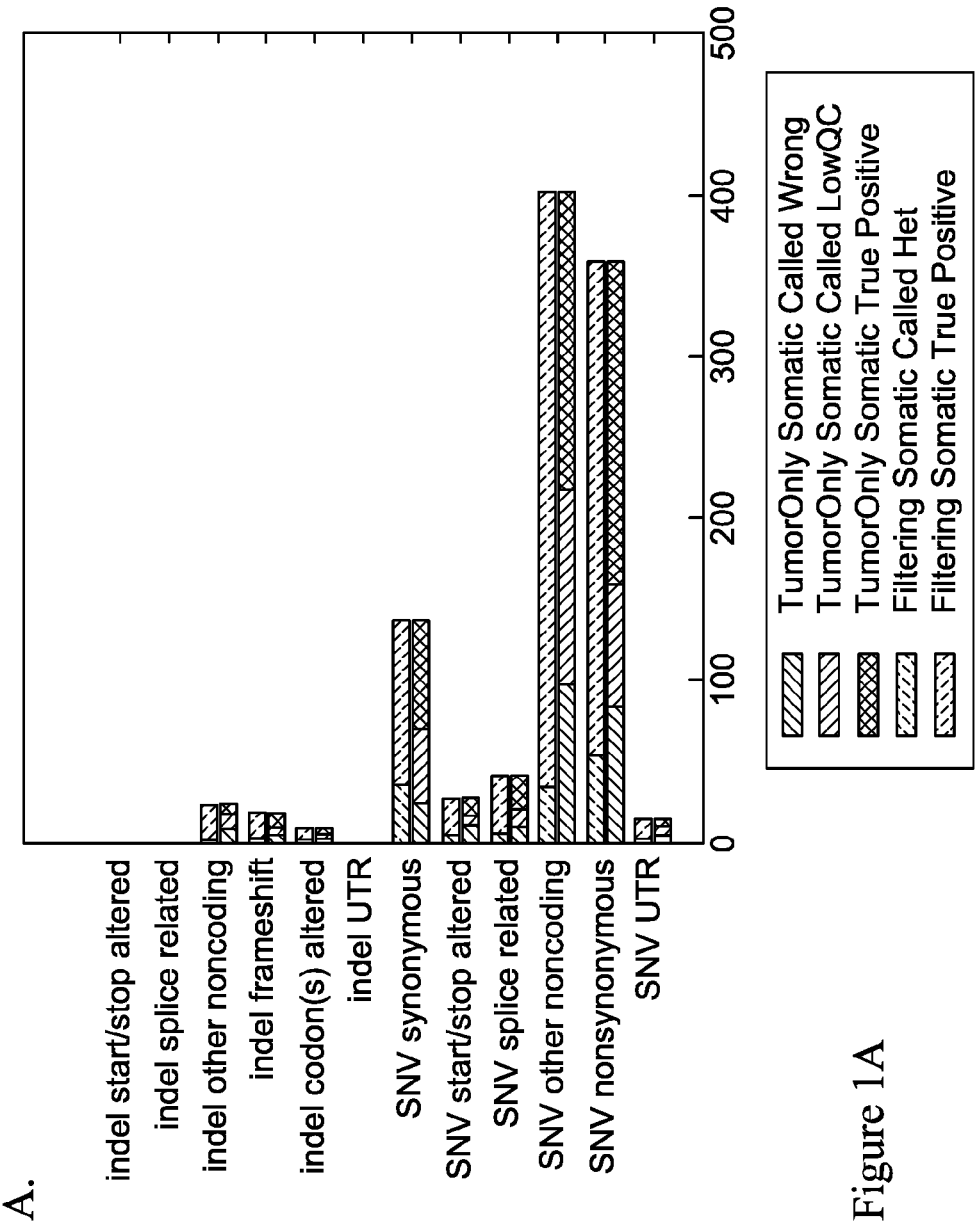

The present subject matter is directed to the detection of variants, which include, for example, mutations, polymorphisms, alterations, and allelic variants. Although systems, methods, and computer program products for detection of somatic mutations in DNA sequencing data will be discussed in detail below, these are being provided as exemplary embodiments. One skilled in the art would also recognize that the present subject matter can also be used for detection of other variants from other sequencing data.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

While the invention has been described in connection with specific embodiments thereof, it will be understood that it is capable of further modifications. This application is intended to cover any variations, uses, or adaptations of the invention following, in general, the principles of the invention. This application includes such departures from the present disclosure as come within known or customary practice within the art to which the invention pertains and as may be applied to the essential features hereinbefore set forth and as follows in the scope of the appended claims.

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), and laboratory animals (e.g., rodents such as mice, rats, and guinea pigs). In preferred implementations, the subject may be a human.

As used herein, the term "sample" is used in its broadest sense and can refer to a bodily sample obtained from a subject (e.g., a human). A "sample" may be any cell source from which DNA, including genomic, somatic, and germline DNA, RNA (i.e., any form of RNA), and/or protein may be obtained. A sample can include a "clinical sample", i.e., a sample derived from a subject. Samples may include, but are not limited to, peripheral bodily fluids, which may or may not contain cells, e.g., blood, urine, plasma, and serum. Samples may include, but are not limited to, archival samples with known diagnosis, treatment and/or outcome history. Samples may include, but are not limited to, tissue or fine needle biopsy samples, and/or sections of tissues, such as frozen sections taken for histological purposes. For example, in some forms of cancer, a sample may be obtained from the local site of the tumor and may include tissue adjacent to the tumor. Thus, a sample may contain both tumor and non-tumor cells. The term "sample" may also encompass any material derived by processing the sample. Derived materials can include, but are not limited to, cells (or their progeny) isolated from the biological sample and proteins extracted from the sample. Processing of the biological sample may involve one or more of, filtration, distillation, extraction, concentration, fixation, inactivation of interfering components, addition of reagents, and the like.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to a nucleic acid or portion of a nucleic acid comprising a sequence that encodes a protein. It is understood in the art that a gene also comprises non-coding sequences, such as 5' and 3' flanking sequences (such as promoters, enhancers, repressors, and other regulatory sequences) as well as introns.

As used herein, "coding" sequence or region refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, the "non-coding" sequences or regions refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

As used herein, an "allele" refers to an alternative sequence at a particular locus. In this invention, "allele" includes all variants and differences in a gene, including deletions, amplifications, or a difference as small as one nucleotide base.

As used herein, the term "variant" when used in reference to a nucleotide sequence refers to a nucleic acid sequence that differs by one or more nucleotides from another, including deletions and amplifications.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism includes a single nucleotide polymorphism (SNP), single-nucleotide variant (SNV), a simple sequence repeat (SSR) and/or "INDELS", which are insertions and deletions. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the later may be associated with rare but important phenotypic variation. In some embodiments, a "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, the term "mutation" is meant to include all kinds of nuclear and/or mitochondrial gene mutations, including point mutations and small insertion/deletion mutations (e.g., 1-50-bp insertion or deletion mutation). Mutations can lead to changes in the structure of an encoded protein or to a decrease or complete loss in its expression. Because a change in the DNA sequence affects all copies of the encoded protein, mutations can be particularly damaging to a cell or organism. In contrast, any alterations in the sequences of RNA or protein molecules that occur during their synthesis are less serious because many copies of each RNA and protein are synthesized.

The term "deletion mutation," as used herein, refers to the removal or loss of one or more nucleotides from a nucleic acid sequence, and is also referred to in the art as a "gene deletion," a "deficiency," or a "deletion." The term "insertion mutation" (or "insertion"), as used herein, refers to the addition of one or more nucleotides into a nucleic acid sequence. The term "chromosome amplification" or "gene amplification" or "amplification" as used herein, refers to an increase in the number of copies of a gene or a number of genes in an organism's genome.

As used herein, the term "isolated" when used in relation to a nucleic acid, as in "an isolated nucleic acid" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes, RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form.

As used herein, the term "sequencing" and its variants comprise obtaining sequence information from a nucleic acid strand, typically by determining the identity of at least some nucleotides (including their nucleobase components) within the nucleic acid molecule. The term sequencing may also refer to determining the order of nucleotides (base sequences) in a nucleic acid sample, e.g. DNA or RNA. Many techniques are available such as Sanger sequencing and high-throughput sequencing technologies (also known as next-generation sequencing technologies) such as the GS FLX platform offered by Roche Applied Science, based on pyro sequencing.

As used herein, the phrase "next generation sequencing" refers to sequencing technologies having increased throughput as compared to traditional Sanger- and capillary electrophoresis-based approaches, for example with the ability to generate hundreds of thousands or millions of relatively small sequence reads at a time. Some examples of next generation sequencing techniques include, but are not limited to, sequencing by synthesis, sequencing by ligation, and sequencing by hybridization. Examples of next generations sequencing processes include pyrosequencing as used by 454 Corporation, Illumina's Solexa system, the SOLiD™ (Sequencing by Oligonucleotide Ligation and Detection) system (Life Technologies Inc.), and Ion Torrent Sequencing systems such as the Personal Genome Machine or the Proton Sequencer (Life Technologies Inc.)

As used herein, "genotype" refers to the entire set of genes carried by an individual, whereas "phenotype" refers to the function and physical appearance of an individual. Phenotype also refers more broadly to characteristics, properties, attributes, functions, etc., that may result from a combination of two or more phenotypic characteristics.

As used herein, the term "genome(s)" means the hereditary information of an individual typically encoded in nucleic acids, either DNA, or RNA, and including both genes and non-coding sequences. The genome may refer to the nucleic acids making up one set of chromosomes of an organism (haploid genome) or both sets of chromosomes of an organism (diploid genome) depending on the context in which it is used.

As used herein, the term "chromosome" refers to the support for the genes carrying heredity in a living cell, including DNA, protein, RNA and other associated factors.

The term "heterozygous" refers to a condition in which different alleles exist at corresponding loci on homologous chromosomes, while the term "homozygous" refers to a condition in which identical alleles exist at corresponding loci on homologous chromosomes.

As used herein, the term "exome" refers to the collection of genomic segments that include protein coding regions, exons, promoters, known ncRNAs (non-coding RNAs) and UTRs, altogether comprising about 2% of the human genome.

As used here in the term "library" is used in its artrecognized sense, that is a collection of nucleic acid molecules (RNA, cDNA or genomic DNA) obtained from a particular source being studied, such as a certain differentiated cell, or a cell representing a certain species (e.g., human).

As used herein, the term "allelic fractions" refers to the fraction of DNA molecules harboring an alteration.

As used herein, the term "tumor-cell fraction" refers to the fraction of cancer cells in a tumor sample.

As used herein, the term "copy number alteration" refers to a gain or loss of copies of some chromosomes or segments of chromosomes caused by rearrangements of the genome in tumor cells. The result is a variation from two copies per gene.

Next-generation sequencing of tumors is widely used both for the discovery of biologically important somatic variants as well as for personalized treatment based on clinically relevant somatic variants. In both cases, accurate identification of somatic variants is crucial. Ideally, a constitutional DNA sample from the same individual is sequenced in parallel, so that somatic variants can be identified by comparing the tumor to the constitutional sequence. In some cases, the constitutional sample may not be available, such as with many archival samples. Tumor-only sequencing is also frequently used in clinical practice[16]. Without a matched germline sequence it is difficult to differentiate between private germline variants and somatic variants[17]. In addition to using variant databases to filter out germline variants, it is also possible to use variant allele frequencies to differentiate between somatic and germline variants[18,19].

Misidentifying germline variants as somatic can be problematic in several ways, depending on the mutation. First, the interpretation of a previously uncharacterized variant would be very different depending on whether it was thought to be somatic or germline. Healthy individuals typically have 130-400 rare non-synonymous germline variants[20]. Therefore, it is not surprising that a study sequencing a panel of 42 cancer genes in 175 participants uncovered 269 germline missense mutations of unknown significance[21]. According to ACMG guidelines, missense germline mutations that are rare and have not been functionally characterized should be reported as uncertain or likely benign[22]. Since tumor suppressors tend to have loss of function mutations through their length, it is unlikely that any specific mutation in a tumor suppressor is well characterized[23]. Clinical tumor sequencing tests, such as MSK-IMPACT, typically include uncharacterized non-synonymous mutations in known cancer genes in the main body of their report[24].

There are some variants, such as those in BRCA1 and BRCA2 that are known to occur in the germline and affect cancer risk but may also occur as somatic mutations in tumors. A study of tumors with matched normal sequencing in over 1000 individuals identified known pathogenic germline variants in over 2% of the participants[25]. Jones et al. examined the presence of germline false positives when tumor samples were analyzed without a matched normal sample[17]. The study used standard somatic variant calling tools designed for matched tumor-normal pairs with unmatched tumor-normal pairs. After filtering out putative germline variants by removing those found in public databases, it was found that an average of 65% of the variants called somatic in the unmatched samples were private germline variants. Additionally, strict filtering removed a small number of mutations that were truly somatic. Most strikingly, they found that ~50% of patients in their cohort would have germline false positives in clinically actionable genes.

Although many methods have been developed to distinguish germline and somatic variants from tumor-only sequencing data, none of these methods fully address the following issues. A typical individual has an average of 249 private germline variants not found in the population databases[8]. The number of private germline variants varies based on the individuals' ancestry. The number of private germline variants depends both on how well represented the population is in large-scale sequencing projects and the extent to which the database has undergone a recent expansion adding to the diversity of variants. Further, approaches requiring a large patient cohort from the same cancer type do not work well when the cancer type is rare, and a large patient cohort is unavailable. Finally, copy number alterations in the tumor can shift both the somatic and germline variant allele fractions, causing considerable overlap in the expected somatic and germline variant allele fractions and reduced power to detect somatic variants.

The present subject matter addresses these issues by providing a new bioinformatics approach. The present subject matter implements a Bayesian tumor-only somatic variant caller that leverages both prior knowledge of population frequencies of germline and cancer mutations, as well as the observed variant allele frequencies. The present subject matter further leverages adjacent normal tissue from tumor biopsies and allows for the determination of the presence of somatic mutations. In some aspects (e.g., LumosVar[15]), the present subject matter models allelic copy number to determine the expected allelic fractions for somatic and germline variants as well as incorporates population database frequencies to call variants as somatic or germline. In other aspects (e.g., LumosVarMulti), the present subject matter additionally finds the joint probability of somatic and germline mutations across multiple samples (with different tumor content) from the same patient.

Figure 1B:
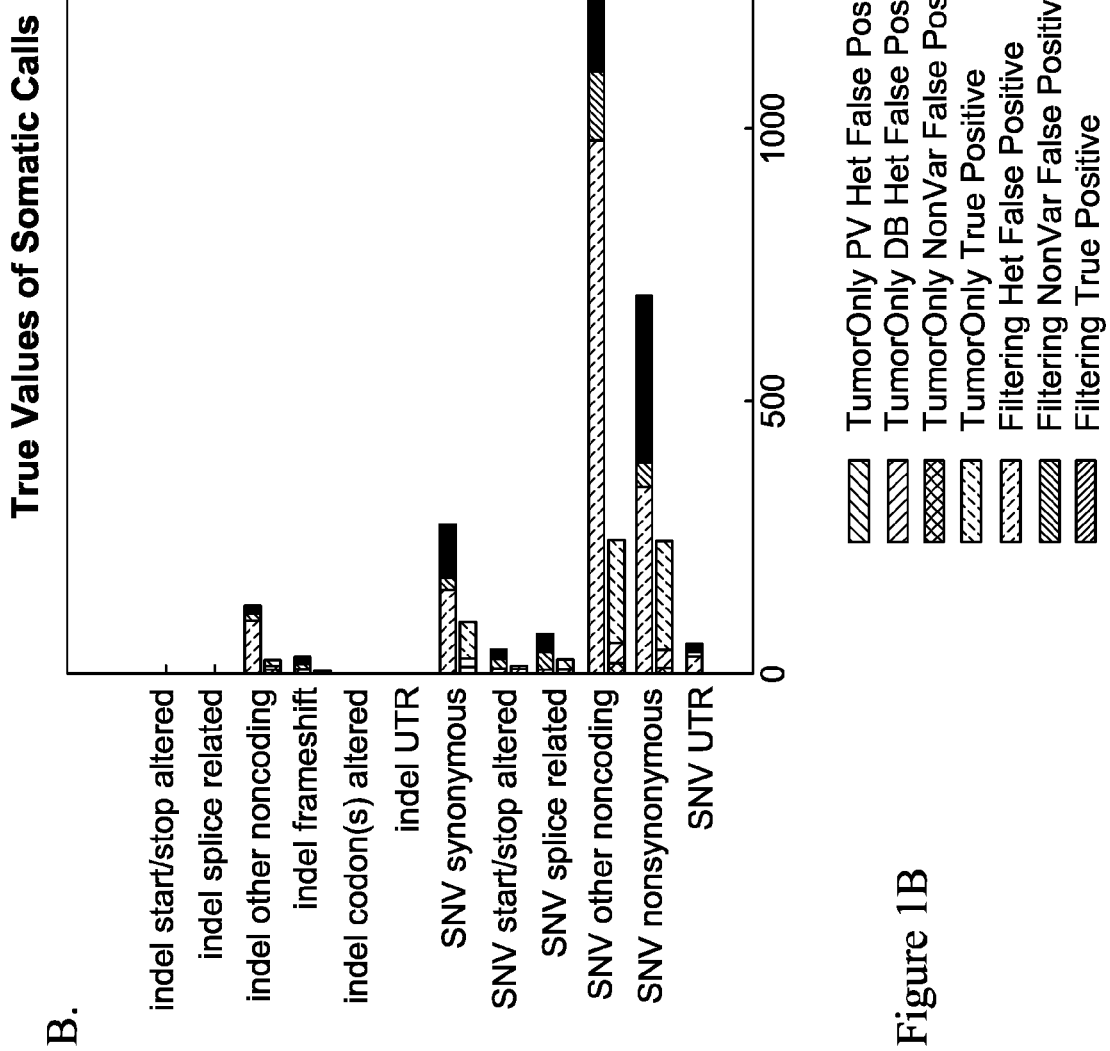

The advent of next-generation sequencing has accelerated the discovery of cancer driver mutations. However, we have now reached a point where most of the common coding driver mutations have already been discovered[23]. Efforts are now turning to uncover rare and noncoding driver mutations[26-28]. One prominent example of a noncoding driver mutation is the TERT promoter mutation[29]. Statistical methods may be used to prioritize somatic noncoding mutations for functional characterization[30,31]. Germline variants may also contribute to cancer risk and progression[32]. Different statistical models are required to analyze germline and somatic alterations[33]. When a filtering approach is used, the false positive rate is much higher for noncoding variants, as most large-scale sequencing projects have focused on coding regions (FIG. 1). The present methods are extremely valuable for discovering novel noncoding variants in unmatched tumor cohorts. As private germline variants are potential false positives in tumor-only somatic variant calling, the number of private germline variants that an individual has would have a direct impact on the calling precision.

The present subject matter takes into account how the number of private germline variants varies with ancestry and uses a strategy to reduce false positives due to private germline variants in tumor-only somatic mutation calling. The present subject matter uses a model of variant allele frequencies to improve classification of somatic versus germline variants. The present subject matter estimates allelic copy number and clonal sample fractions to model the expected allele frequency distributions of somatic and germline variants. The present subject matter uses a Bayesian framework that integrates the allele frequency model with prior probabilities of somatic or germline calculated from 1000 genomes population and cancer mutations counts from COSMIC. The power to detect somatic variants by the present subject matter has been evaluated. In one approach, the effects of tumor content, copy number, and read depth were systematically examined on simulations. In a second approach, in silico dilutions and downsampling were used to examine effects of tumor content, copy number, and read depth on real patient data. In a third approach, tumor samples of different ancestry were used to evaluate the tumor-only calling approach.

In one embodiment of the present invention (e.g., LumosVar), allelic fractions of variants in a single sample are used to infer whether the variants are somatic or germline. In another embodiment of the present invention (e.g., LumosVarMulti), allelic fractions of variants in multiple samples are used to infer whether the variants are somatic or germline.

LumosVarMulti is a software package designed to jointly analyze multiple samples from the same patient. The approach is based on the concept that the allelic fraction of somatic variants, but not germline variants, would be diluted by the presence of normal tissue. Given the allele-specific copy number state and expected tumor fraction of each sample, LumosVarMulti can model the expected allelic fractions of somatic and germline variants. LumosVarMulti estimates allele-specific copy number and tumor sample fractions from the data and uses the model to call somatic and germline variants. LumosVarMulti also detects subclonal events and spatial heterogeneity between samples. The multi-sample approach has the following advantages:

Improved detection of somatic variants in samples without a matched germline sample available. Allelic fractions from more than one sample can be used. Ideally one would want a high tumor and a low tumor content sample to analyze jointly. In a high tumor content sample alone, it is difficult to tell somatic from germline variants, while in low tumor samples it can be difficult to detect somatic variants at all. By analyzing high and low tumor samples jointly, the high tumor sample allows the detection somatic variants, and the low tumor sample allows the detection and identification of variants that are not germline variants.

Ability to determine whether there is evidence of variants called in multiple samples from the same patient. In a typical workflow, one would find somatic variants in each sample independently and then go back to the raw data to look for whether there is evidence of any variants that were called in one sample in the other samples. LumosVarMulti looks at all of the samples jointly and determines which ones have evidence of the variant.

Greater sensitivity in detecting low allelic fraction variants that are present in more than one sample. Finding a small number of reads supporting a variant in more than one sample from the same patient would give more confidence that the variant is a true variant than finding the same number of reads in a single sample.

Estimation of the fraction of each sample containing the variant. The multi-sample approach provides a tool that integrates the allelic fractions estimation with the variant calling step.

Group somatic point mutation and copy number variants that show similar patterns across samples into clones. The multi-sample approach provides a tool that integrates analysis of both point mutations and copy number variants.

When a normal sample is available, the multi-sample approach can also take the normal sample as input and provide additional output.

Identify germline copy number variants. The multi-sample approach provides a tool that finds germline and somatic copy number variants in the same analysis.

Identify variants whose allelic fraction does not fit well into a heterozygous or homozygous model. These could be somatic variants that are not specific to the tumor or germline copy number variants that were missed by the copy number model.

Identify rare (for example, $\leq 1E-6$, $\leq 1E-5$, $\leq 1E-4$, or $\leq 1E-3$, etc.) and/or non-coding variants.

EXAMPLES

Example 1. Methods a. Nucleic Acid Isolation

Ethics approval and consent to participate: All patients consented to an institutional review board-approved protocol that allows comprehensive genetic analysis of tumor and germline samples. Information regarding patients and samples are provided (FIG. 2).

Formalin-fixed tissue, clinical and pathology data, and pre-operative MRI scans were acquired for twenty breast cancer patients and twenty prostate cancer patients from HonorHealth Scottsdale, in accordance with local institutional review boards and in compliance with the Health Insurance Portability and Accountability Act (HIPAA). IRB approval included a waiver of informed consent for the prostate cancer patients. Patients in the breast cancer cohort provided signed consent to participate in the study. A retrospective analysis was performed using archival samples from treatment-naïve, invasive breast carcinomas or treatment-naïve prostate adenocarcinomas.

Breast tumors were collected following routine clinical lumpectomy or mastectomy, from women diagnosed with ER-positive, invasive mammary carcinoma between 2010 and 2016 at HonorHealth Scottsdale. The median age of diagnosis was 65 years and ranged from 39 to 86 years. All tumors were classified by pathology as estrogen receptor-positive. Nineteen of the twenty tumors were classified as HER2-negative. The breast tumor cohort spanned AJCC stages (IA-IV). Prostate tumors were collected following radical prostatectomy for men diagnosed with pancreatic adenocarcinoma between 2012 and 2016 at HonorHealth Scottsdale. The median age of diagnosis was 67 years, ranging from 57 to 74 years. Eighteen of the twenty tumors had a Gleason score of seven or greater. ER/PR/HER2 status (breast tumors), Gleason score (prostate tumors), histological type, tumor stage, treatment history, and clinical outcome, including progression-free survival and overall survival, were collected from medical records and the de-identified data was provided for this study. Pathology review identified a tissue block with high tumor content and a tissue block with a region considered to have low tumor content for each patient. Five 10-micron sections were provided for each sample (5 high tumor content; 5 low tumor content).

For freshly collected biospecimens, macrodissections and the Qiagen GeneRead formalin fixed paraffin embedded (FFPE) DNA Kit (cat#180134) was used to isolate constitutional and tumor DNA from FFPE breast and prostate cancer tumor specimens (N=80) following the manufacturer's protocol.

For fresh frozen tissue, tissue from the needle biopsy was disrupted and homogenized in Buffer RLT plus, Qiagen AllPrep DNA/RNA Mini Kit (Qiagen, Germantown, MD), using the Bullet Blender™, Next Advance. Specifically, tissue was transferred to a microcentrifuge tube containing 600 μl of Buffer RLT plus, and stainless steel beads. The tissue was homogenized in the Bullet Blender at room temperature. The sample was centrifuged at full speed, and the lysate was transferred to the Qiagen AllPrep DNA spin column. Genomic DNA purification was conducted as directed by the AllPrep DNA/RNA Mini Handbook, Qiagen. DNA was quantified using the Thermo Scientific Nanodrop spectrophotometer, and quality was accessed from 260/280 and 260/230 absorbance ratios.

For blood germline tissue, the QIAamp DNA Blood Maxi Kit, Qiagen, was used to isolate DNA from 8 to 10 ml of whole blood. The protocol was conducted as written. Specifically, the buffy coat layer was isolated from whole blood by centrifugation. The volume of buffy coat was brought up to 5-10 ml with PBS and treated with Qiagen protease at 70° C. 100% ethanol was added, and the sample was applied to a QIAamp Maxi column and centrifuged. Samples were then washed with buffers AW1 and AW2 and eluted in 1000 μl of Buffer AE. The Qubit 2.0 Fluorometer, Invitrogen, and the Nanodrop spectrophotometer, Thermo Scientific, were used to assess DNA quality and concentration.

Slides mounted with 10 um FFPE tissue sections were incubated in a thermal oven overnight at 60° C. Deparaffinization was conducted on slides by three exchanges of xylene followed by washes in descending concentrations of ethanol (100, 95, 70, 50 and 20%) and a final wash in deionized water. Tumor tissue was scraped using a double-edge dissecting needle and transferred into a 1.5 ml microcentrifuge tube containing 150 μl of Buffer PKD and 10 μl of proteinase K. Samples were vortexed to mix, incubated at 56° C. for 15 min and chilled on ice for 3 min. After centrifugation at 20,000×g for 15 min, the supernatant was transferred to a new 1.5 ml centrifuge tube for RNA purification. The pellet was resuspended in 180 μl of Buffer ATL containing 40 μl of proteinase K, mixed by vortexing and incubated at 56° C. for 1 h followed by incubation at 90° C. for 2 h. After brief centrifugation, samples were treated with 4 μl of RNase A (100 mg/ml) at room temperature. Genomic DNA purification was conducted with automation on the QIAcube using the AllPrep DNA/RNA FFPE Kit and the QIAcube standard protocol. Purification of DNA and total RNA including small RNAs from FFPE tissue sections, Version 2 (DNA purification). Samples were eluted in 100 μl of BufferATE. Extracted DNAs were quantified using the Invitrogen 2.0 fluorometer, and DNA quality was assessed on the Nanodrop by evaluating 260/280 and 260/230 absorbance ratios.

Samples may contain varying percentages of tumor cells. In some embodiments, at least 2%, at least 5%, at least 10%, at least 15%, at least 20%, at least 25%, at least 30%, at least 35%, at least 40%, at least 45%, or at least 50% of the cells in the tumor sample are normal, non-tumor cells. In other embodiments, normal, non-tumor cells are between 2-5%, 2-10%, 2-15%, 5-10%, 5-15%, 5-20%, 5-30%, 5-40%, 10-20%, 10-30%, 10-40%, 20-30%, 20-40%, 20-50%, 30-40%, or 30-50% of the tumor sample.

In some embodiments, tumor samples have a matched normal sample where the matched normal sample is derived from tissue adjacent to the tumor. Sample regions with different tumor contents (e.g., one sample region has relatively higher tumor content than another sample region) are identified (for example, using Pathology review). The sample regions with different tumor contents are separated (e.g., using macro-dissection).

b. Library Preparation and Sequencing

Exome libraries were constructed from 200 ng of DNA (DIN=3-5) using KAPA Biosystems' Hyper Prep Kit (cat#KK8504) and Agilent's SureSelectXT V5 baits, containing custom content, following the manufacturer's protocols. Custom bait content included copy number probes distributed across the entire genome, along with additional probes targeting tumor suppressor genes and genes involved in common cancer translocations to enable structural analysis.

Libraries were equimolarly pooled, quantitated, and sequenced by synthesis on the Illumina HiSeq2500 using paired-end 83×83 bp reads or the Illumina HiSeq 4000 for paired 82 bp reads. Paired tumor/normal exomes were constructed using KAPA Biosystems' Library Preparation Kit using the manufacturer's "with bead" protocol and Agilent's XT2 adaptors and Agilent's SureSelect Human All Exon V5+UTR baits. Unmatched tumor SBS Kit V3 on the Illumina HiSeq.

Tumor and normal genome libraries were sequenced with paired 125 bp reads using Illumina HiSeq2500 V4 chemistry running HCS2.2 controller software and RTA 1.18.61. The five lanes of each library generated 2.819 billion reads for the tumor and 2.968 billion reads for the normal sample.

Availability of data and material: Data is being shared based on participants' informed consent and in accordance with NIH Genomic Data Sharing Policy. Genotype data is available through dbGaP phs000748.v1.p1, and sequencing data for dilution series is being shared as part of a separate dbGAP submission.

c. Software Availability and Requirements

LumosVar requires Perl, Samtools, htslib, and MATLAB runtime. The main inputs are bam files, which may be generated by BWA. LumosVar is available for download at https://github.com/tgen/LumosVar.

d. Alignment and Assembly

Pipeline analysis is triggered when data is written from the sequencer to the analysis server in the form of BCL files. Using a queuing system and write FAIL/COMPLETED system BCL files are converted to FASTQ files (raw sequence) and aligned to the genome using BWA-MEM (version 0.7.8)[34]. BWA-MEM aligns long query sequences against a large reference genome utilizing a backward-search with a Burrows-Wheeler Transform tool. The reference genome from 1000 Genomes project build hs37d5 with decoy contigs [b37d5] and Ensembl v74 for annotations was used[35]. For the samples containing the molecular barcodes, the barcodes were appended to the RG tags using a custom script. BAM files were sorted with SAMTools (version 0.1.2) and merged and duplicate marked using Picard MarkDuplicates.jar (version 1.111). Chastity failed reads were marked in the BAM files through a custom script using the Picard Tools API (version 1.31). Targeted reassembly was performed using ABRA (version 0.94)[36]. These final BAM files were then used to identify genetic variants.

e. In Silico Dilutions and Downsampling

For the in silico dilutions, BAMs of the tumor and normal samples were subsampled and then merged using samtools. For the downsampling experiment, samtools was used to subsample the tumor bam.

f. Benchmark Variant Calling

We use benchmark variant calling as an independent approach for evaluating the single- and multiple-sample approaches. Germline SNV and INDELS were identified using HAPLOTYPE CALLER (version 3.1-1)[37], samtools (version 1.2)[38] and freebayes (v0.9.21)[39] in the constitutional sample. Somatic SNV and INDEL were identified using three different somatic variant callers SEURAT[40], STRELKA[41], and MUTECT[42]. After normalizing INDELs with VT[43], a custom script was used to merge the VCFs from the three callers. A set of ten constitutional samples was pooled as an unmatched reference sample for the somatic SNV and INDEL callers. Agreement of all callers was required to define a true variant (FIG. 3). Positions with discordant calls were considered unknown and excluded from sensitivity and precision calculations.

g. Germline Variant Filtering

We also use germline variant filtering as an independent approach to compare to the lumosVar approach. Known germline variants were identified by their presence in dbSNP (build 146)[44]. Since dbSNP does contain somatic variants, the "allele origin" field was used to exclude those variants from germline filtering. Variants with an allele origin listed as germline or unspecified were considered known germline variants, while those listed as somatic, both, or not present in dbSNP were considered potential somatic or private germline variants. For the filtering approach, variants called by all somatic callers in the pooled reference comparison, and not filtered out as known germline variants were considered somatic calls.

h. Simulations

Simulated data was used to systematically determine how the purity of the two tumor samples, the copy number, and the read depth affect our ability to detect somatic variants.

Read depth of each mutation was drawn from a log normal distribution where $\overline{R_T}$ is the mean target coverage. The standard deviation was derived from fitting a lognormal distribution to the read depth distribution from several tumor samples.

$$R_T \sim \text{lognormal}(\overline{R_T}, 1, 1).$$

The expected allele frequency of a somatic variant ($\phi^S$) is a function of the fraction of cells in the sample containing the variant (f), the total copy number (N), and the minor allele copy number (M).

$$\phi^S = \frac{f*(N-M)}{f*N + 2*(1-f)} \quad (1)$$

The read depth of the B alleles were drawn from a binomial distribution as $R_B$.

$$R_B \sim \text{binomial}(R_T, \phi^S)$$

To evaluate how the joint calling approach (e.g., lumosVarMulti) compares to the single sample approach (e.g., lumosVar), the read depths of each pair of simulated tumor samples was added and used jointly.

i. Variant Caller Overview

Once aligned sequence data from tumor samples is received, candidate variant within the aligned sequence data will be identified. Either a single-sample strategy or a multi-sample strategy can be used to determine whether a candidate variant is somatic, germline heterozygous, or homozygous, or a sequencing/alignment artifact.

Figure 4:
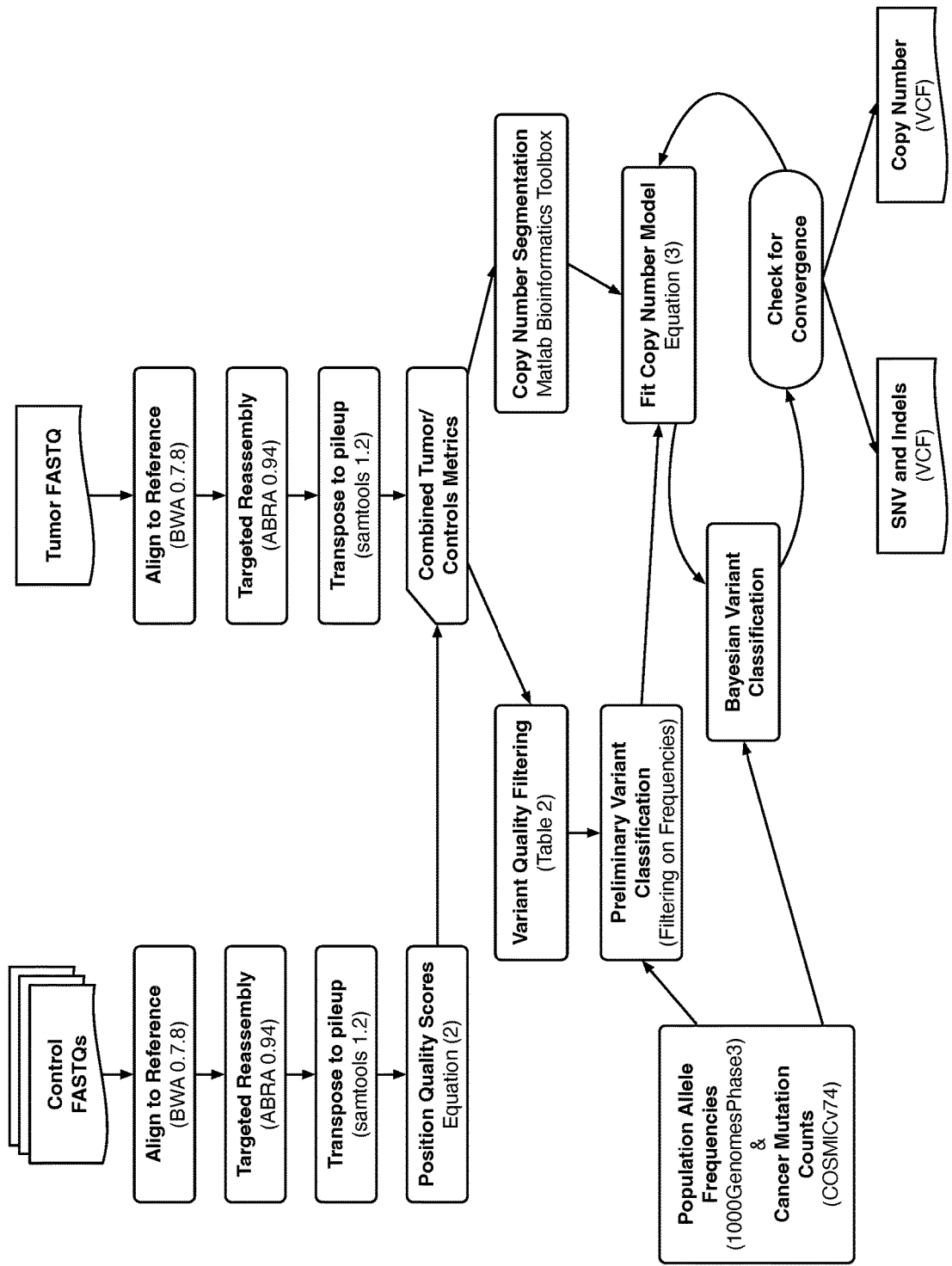
FIG. 4 A detailed workflow of the single-sample somatic variant calling process. The lumosVar software performs the steps from "Transpose to pileup" and below.
Figure 5:
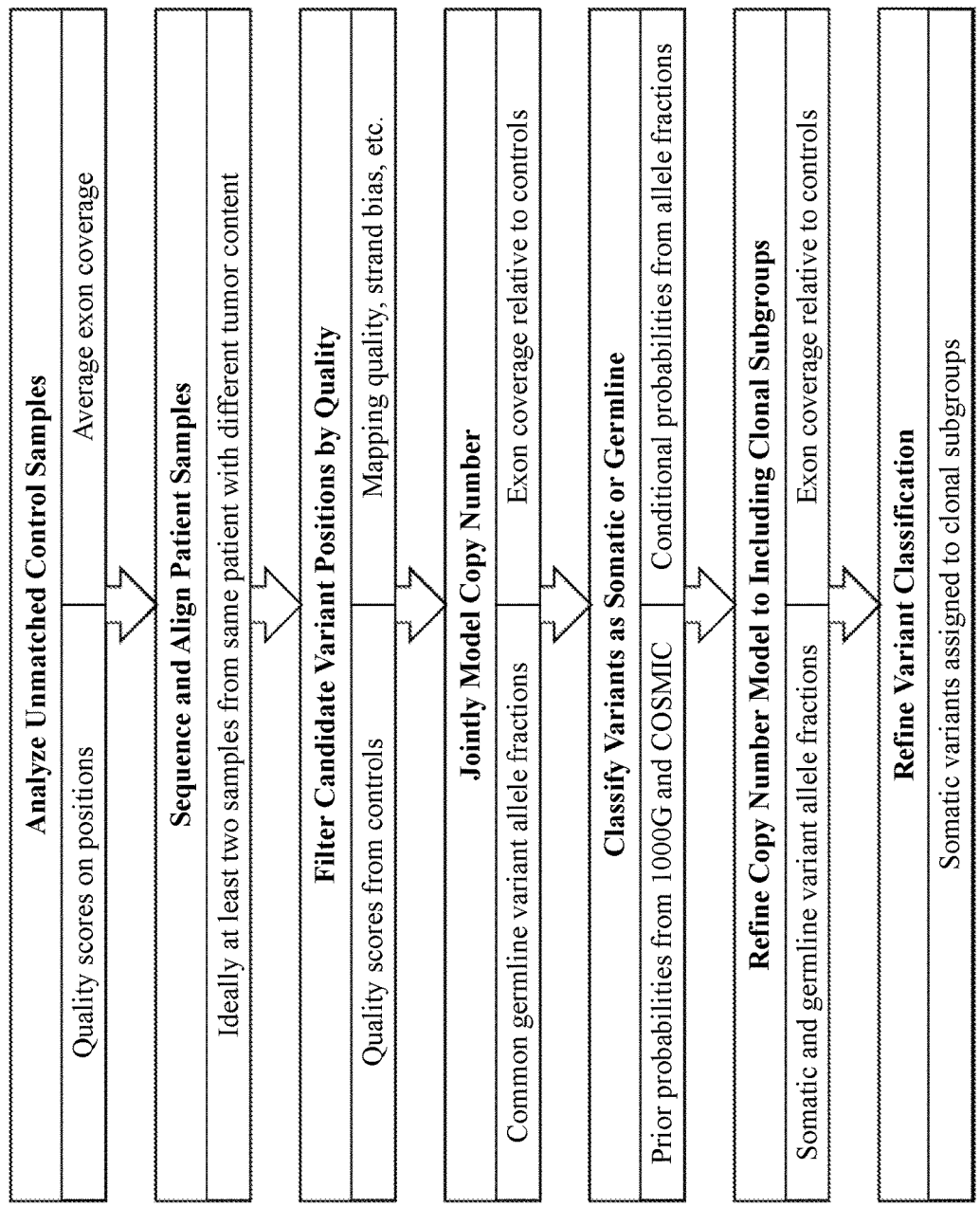
FIG. 5 A detailed workflow of the multiple-sample somatic variant calling process.

A single-sample strategy (e.g., lumosVar) can be used to call somatic variants in tumor samples (e.g., impure tumor samples) based on the differences in allelic frequency between the somatic and germline variants[15] (FIG. 4). A multiple-sample strategy (e.g., lumosVarMulti) is to extend the single-sample strategy and jointly analyze multiple samples from the same patient (FIG. 5).

The single-sample strategy (e.g., the lumosVar approach) consists of four main steps. The first step analyzes a set of unmatched controls to obtain position quality scores and average exon read depths for the copy number analysis. The second step calculates position quality scores of a candidate variant position in the tumor sample, which takes into account both the quality scores from the unmatched controls as well as quality metrics from the tumor sample such as mapping quality scores and strand bias. The third step estimates the allelic copy number and clonal sample fractions. For purposes of the single-sample strategy, it is assumed that (1) each sample contains different proportions of each clonal variant group; (2) subsets of variants occur in the same fraction of the cells in the sample due to clonal expansions; and (3) at most one variant group has a copy number alteration in a given segment. Subsets in this single-sample strategy indicate groups of variants that follow a similar pattern across the samples from that patient. There are a fixed number of these subsets that have the same sample fraction, and each variant (mutation or copy number) is assumed to belong to one of these subsets. The user may select any positive integer number of subsets. In the results presented here, three subsets were used. In an unrelated training dataset, a selected quantity of three subsets was found to work well for most samples. An expectation maximization approach is used to find the clonal sample fractions that best explain the data and assign the most likely copy number state to each segment and sample fraction to each variant. The fourth step finds the posterior probability that each candidate variant is somatic, germline heterozygous, or homozygous based on the expected allelic fractions for somatic and germline variants which takes into account the allelic copy number and clonal sample fractions. The somatic and heterozygous germline variants are then used as input to the third step. The caller iterates between the third and the fourth step until the result converges (FIG. 4).

The multiple-sample strategy (e.g., the lumosVarMulti analysis) has four main steps. The first two steps are identical to the single-sample strategy. The third step uses an expectation maximization approach to optimize a centering parameter (C), a parameter (W) that controls the spread of the allelic fraction distributions, and the variant group clonal sample fractions (f). The multiple-sample strategy aimed to maximize the following sum of likelihoods: 1) the likelihood of the exon read depth, given the sample fraction and centering parameters; 2) the likelihood of the heterozygous variant B allele read depth, given the sample fractions and W parameter; 3) the likelihood of the somatic variant B allele read depth, given the sample fractions and W parameter; 4) the likelihood of observing at most the number of heterozygous positions detected in each segment; and 5) the likelihood of observing the number of somatic calls in known germline variant positions. The fourth step finds the posterior probability that each candidate variant is somatic, germline heterozygous, or homozygous based on the expected allelic fractions for somatic and germline variants which takes into account the allelic copy number and clonal sample fractions. The product of the conditional probabilities across the set of samples gives the joint probability of each variant type, given all the samples' data. The caller iterates between steps three and four (including the steps of (a) modeling to find a copy number state estimate of the segments and a tumor-cell fraction of the main and subclonal variant group(s); (b) determining an expected allelic fraction of the candidate variant given both a somatic and a germline model; (c) determining a posterior probability that a candidate variant is somatic, germline heterozygous, or homozygous by calculating the likelihood of the observed allelic counts given the somatic and the germline models; d) repeating steps a through c until the solution converges) (FIG. 5).

j. Position Quality Scores from Unmatched Controls

A quality score for each position in the exome is determined based on the assumption that positions that do not appear diploid in control samples are unreliable. The conditional probability of the data (D) given that the position is homozygous (P(D/$G_{AA}$)), heterozygous (P(D/$G_{AB}$)), or poorly mapped (P(D/U)) are calculated based on the number of reads supporting the B allele ($R_B$), the total number of reads ($R_T$), the mean base quality of the B allele ($Q_B^b$) and the mean mapping quality of the A or B alleles ($Q_A^m$ or $Q_B^m$). The read depths of the B allele are assumed to follow a binomial distribution with $R_B$ successes, $R_T$ trials, and the probability of success depends on the genotype. For homozygous positions, the probability of observing reads supporting the B-allele depends on the mean B allele base quality and is 0.5 for heterozygous positions.

$$P(D/G_{AA}) = \text{binomial}_{pmf}\left(R_B, R_T, 10^{-\frac{Q_B^b}{10}}\right);$$

$$P(D/G_{AB}) = \text{binomial}_{pmf}(R_B, R_T, 0.5);$$

$$P(D/U) = 10^{-\frac{\min(Q_A^m, Q_B^m)}{10}}.$$

The prior probabilities of homozygous ($\pi_{AA}$) or heterozygous ($\pi_{AB}$) are based on the population allele frequencies ($F_A$ and $F_B$), assuming Hardy-Weinberg equilibrium and the prior probability that the position is unreliable is a constant ($\pi_u$) reflecting the percentage of the exome expected to be mappable[45]. The posterior probability that the position is unreliable is given the data:

$$P(U/D) = \frac{P(D/U) * \pi_U}{P(D/G_{AA}) * \pi_{AA} + P(D/G_{AB}) * \pi_{AB} + P(D/U) * \pi_U}.$$

The mean posterior probability that the position is unreliable is calculated across the unmatched controls for each position and then transformed to Phred-like score.

k. Tumor Quality Metrics and Filtering

In certain embodiments of the single-sample approach, sixteen quality metrics are calculated at each position (FIG. 6). There are two thresholds for each quality metric: a PASS and a REJECT threshold (FIG. 7). For positions called homozygous in the variant classification below, all the metrics are calculated based on the major allele (A allele) only, and difference metrics are set to zero. Each position that meets all the PASS criteria is assigned to the trusted training group, and each position that meets at least one of the REJECT criteria is assigned to the non-trusted training group. A quadratic discriminant model, fit separately to the homozygous positions, INDEL positions, and all other positions (including somatic and germline heterozygous variants), is trained on the positions that are assigned to the trusted and non-trusted training groups. The quadratic discriminant model is then used to determine the posterior probability that a variant belongs to the trusted training group (PT). In other embodiments of the single-sample approach, the number of clones is not required as input. Instead the model determines the most likely number of clones which maximizes the likelihood of the data. There is an input parameter for a penalty term for adding an additional clone. Typically, increasing the number of subsets (or decreasing the penalty parameter) increases the number of true positive, as well as false positive, variants identified.

Model input parameters are similar for the multi-sample approach. However, one value of f$\pi$ (see FIG. 6) is required for each sample.

A second classification step is performed to determine the probability of a position belonging to an artifact group (PA) where positions meeting at least three REJECT criteria are considered artifact positions, and positions meeting at least 12 PASS criteria and zero REJECT criteria are considered non-artifact positions. A position is called PASS if at least one of the samples showing evidence of the variant has a PT greater than the classification threshold and none of the samples have a PA greater than the classification threshold. A position is called REJECT if all the samples have a PA greater than the classification threshold. All other positions are called LowQC.

Overall, changes in any individual input parameter does not typically cause a large change in the results. Typically, there are tradeoffs between sensitivity and precision for most of the parameters (e.g., increasing a parameter may decrease false negatives but increase false positives, while decreasing the same parameter would decrease false positives but increase false negatives).

The number of variants included in a training group may be 20-50, 50-100, 100-1,000, 1,000-10,000, or greater than 10,000.

1. Copy Number and Clonal Sample Fraction Estimation (Single-Sample Approach)

The mean exon read depths and a set of unmatched normal samples, and the somatic and germline variant allelic read counts (allelic fractions) of the tumor sample will be observed.

To properly determine the expected allelic fractions of germline and somatic variants we need to estimate (model) allele-specific copy number of clonal and subclonal copy number events, as well as the sample fractions (a tumor-cell fraction harboring a specific candidate variant per tumor sample) of the main clonal and sub-clonal populations. The model starts with segmented read count data and finds the most likely allelic copy number state for each segment given the observed mean exon read depths, the B-allele frequencies of the germline heterozygous variants in each segment, and the clonal and subclonal sample fractions. Using an expectation maximization approach, the clonal and subclonal sample fractions are found that maximize the probability of the observed mean exon read depths, germline heterozygous B-allele frequencies, as well as somatic variant B-allele frequencies. Also included are prior probabilities of copy number states and sample fractions to favor solutions more diploid copy number segments and intermediate sample fractions. The model assumes that at most one clone can have a copy number alteration in a given segment, and the rest of the tumor cells, as well as the normal cells, are diploid in that segment (see FIG. 8 for key notation used in the model). The fraction of the total cells in the sample (including both tumor and non-tumor cells) contains a set of somatic variants. The clonal sample fraction corresponds to the percentage of tumor cells in the sample, as clonal variants are in all of the tumor cells.

The copy number segmentation (partitioning the genome into segments) is performed on the ratio of the tumor to the normal mean exon read depth using the circular binary segmentation implementation in the Matlab bioinformatics toolbox. Somatic and germline variant allelic read counts are required as input to the expectation-maximization step. In the initial iteration, likely germline and somatic variants are selected based on database frequencies. In subsequent iterations, the posterior probability described in the "Somatic Variant Calling" section below (Eq. 4) is determined and used to select the positions considered somatic and a similar germline posterior probability is used to select germline variants. In the expectation-maximization step, in addition to optimizing the clonal and subclonal sample fractions (f), the following are optimized: a centering parameter (C) and a parameter that controls the spread of the allelic fraction distributions (W). The expectation-maximization step also aims to maximize the following sum of likelihoods: 1) the likelihood of the exon read depth given the sample fraction and centering parameters, 2) the likelihood of the heterozygous variant B allele read depth given the sample fractions and W parameter, 3) the likelihood of the somatic variant B allele read depth given the sample fractions and W parameter. Terms reflecting the prior probabilities of observing the copy number states and sample fractions are also included in the sum to maximize, as shown below. Here X is the number of exons, X* is the number of copy number altered exons, V is the number of heterozygous germline variants, and Y is the number of somatic variants.

$$\{f, W, C\} = \frac{\operatorname{argmax}\left(\sum_{n=1}^{X} \log(L(C, f \mid R_{Tn})) + \sum_{h=1}^{V} \log(L(f, W \mid R_{Bh}, R_{Th})) + \sum_{s=1}^{Y} \log(L(f, W \mid R_{Bs}, R_{Ts})) + \sum_{n=1}^{X} \log(\pi(N_n)) + \sum_{n=1}^{X} \log(\pi(M_n)) + \sum_{s=1}^{Y} \log(\pi(f_s)) + \sum_{s=1}^{X^*} \log(\pi(f_n))\right)}{3*X + X^* + V + 2*Y}$$

The likelihood of the exon read depth is modeled as a Poisson distribution with a mean of $R_{ni}$, which is calculated, based on the observed exon read depths in the unmatched control samples (Eq. 2, below).

$$L(C, f_i \mid R_{Tn}) = \operatorname{poisson}_{pdf}(\operatorname{round}(R_{Tn}), \operatorname{round}(\hat{R}_{ni})).$$

The likelihood of the heterozygous position minor allele read counts ($R_{Bh}$) is modeled as a beta-binomial distribution with an expected allelic fraction $\phi^G$ (Eq. 3).

$$L(f, i, W_i \mid R_{Bh}, R_{Th}) = \operatorname{betabinomial}_{pmf}(R_{Bh}, R_{Th}, W^*_i \Phi_i, W_i(1-\Phi_i)).$$

The likelihood of somatic position minor allele read counts ($R_{Bs}$) is modeled as a beta-binomial distribution with an expected allelic fraction $\phi^S$ (Eq. 1).

$$L(f, W_i \mid R_{Ts}) = \operatorname{betabinomial}_{pmf}(R_{Bs}, R_{Ts}, \min(W_{Is}\Phi_{Is}^S, W_i(1-\Phi_{Is}^S)), \max(W_{Is}\Phi_{Is}^S, W_{Is}(1-\Phi_{Is}^S))).$$

The prior distribution of f is described as a beta distribution parameterized such that $f_\pi$ is the mode of the distribution.

$$\pi(f) = \operatorname{beta}_{pdf}\left(f, \alpha_\pi, \frac{\alpha_\pi - 1}{f_\pi} - \alpha_\pi + 2\right)$$

In the expectation step, the following are estimated: the copy number and minor allele (B allele) copy number of each segment.

For each clone (i) and segment (j), the copy number ($N_{ij}$) and minor allele copy number ($M_{ij}$) are calculated based on the mean segment read depth in the tumor ($\overline{R_{Tj}}$) and controls ($\overline{R_{C_J}}$), and the mean segment B allele read depth in likely germline heterozygous positions in the tumor ($\overline{R_{HB_J}}$).

$$N_{ij} = \max\left[\text{round}\left(\frac{C * \frac{\overline{R_{T_J}}}{\overline{R_{C_J}}} - 2 * (1 - f_i)}{f_i}\right), 0\right];$$

$$M_{ij} = \text{round}\left(\frac{N_{ij} * \overline{R_{HB_J}}}{f_i * \overline{R_{T_J}}} - \frac{1 - f_i}{2}\right).$$

The expected read depth is calculated for each exon (n) and clone.

$$\hat{R}_{ni} = \frac{f_i * R_{Cn} * N_j + 2 * (1 - f_i) * R_{Cn}}{C}. \quad (2)$$

The expected allele frequencies for germline heterozygous positions are also determined for each clone.

$$\phi_{ij}^G = \frac{f_i * M_{ij}}{N_{ij}} * \frac{1 - f_i}{2} \quad (3)$$

The clone I is found that is most likely to have the copy number alteration in each segment, and then the values of N and M corresponding to the most likely clone are used for that segment are used.

$$I_j = \text{argmax}_i\left(\frac{1}{Q_j}\sum_{n=1}^{Q_j} L(C, f_i \mid R_{Tn})\right) + \frac{1}{V_j}\sum_{h=1}^{V_j} L(f_i, W_i \mid R_{Bh}, R_{Th}))$$

We are then able to find expected allele frequencies for each somatic variant, for each sample fraction. If the variant occurs in a copy-altered segment, then the model takes into account whether the variant occurs on the major or minor copy of the chromosomal segment. It is assumed that a variant that occurs in the same sample fraction as the copy number alteration will be on the major allele, while variants in other sample fractions would occur on exactly one chromosomal copy.

$$\phi_{ij}^S = \begin{cases} i = I_j, & \frac{f_j * (N_j - M_j)}{f_j * N_j + 2 * (1 - f_j)} \\ i \neq I_j \wedge N_j > 0, & \frac{f_i}{f_{I_j} * N_j} + 2 * (1 - f_{I_j}) \\ i \neq I_j \wedge N_j = 0, & \frac{\min(1 - f_{I_j}, f_i)}{2} \end{cases}$$

We can then find the most likely clone for each somatic variant.

$$I_s = \text{argmax}_i(\text{betabinomial}_{pmf}(R_{Bs}, R_{Ts}, \min(W_i \Phi_{ij}^s), W_i(1 - \Phi_{ij}^s)), \max(W_i \Phi_{ij}^s, W_i(1 - \Phi_{ij}^s)))$$

m. Copy Number and Clonal Sample Fraction Estimation (Multiple-Sample Approach)

The single-sample approach has been extended to jointly model multiple samples and automatically determine the number of clonal variant groups (K). We assume that each sample contains different proportions of each clonal variant group. As the single-sample approach, it is also assumed that at most one variant group has a copy number alteration in a given segment. An expectation maximization approach is used to optimize a centering parameter (C), a parameter that controls the spread of the allelic fraction distributions (W), and the variant group clonal sample fractions (f). C and W are vectors with lengths equal to the number of samples (J) and f is a J by K matrix. The single-sample approach aims to maximize the following sum of likelihoods: 1) the likelihood of the exon read depth, given the sample fraction and centering parameters; 2) the likelihood of the heterozygous variant B allele read depth, given the sample fractions and W parameter; 3) the likelihood of the somatic variant B allele read depth, given the sample fractions and W parameter; 4) the likelihood of observing at most the number of heterozygous positions detected in each segment; and 5) the likelihood of observing the number of somatic calls in known germline variant positions. The first three likelihood functions are calculated for each sample, as described previously, and the log likelihoods are summed over the samples.

The probability of detecting a heterozygous variant in each segment is calculated based on the cumulative probability of observing at least the minimum number of reads required to be considered a candidate variant position ($R_{B-min}$), given the mean read depth in the segment ($R_T$) and the expected allele fraction of a heterozygous variant in that segment ($\phi^G$).

$$P_{het} = \text{binomial}_{cmf}(R_{B-min}, R_T, \phi^G).$$

The likelihood of detecting fewer than $Y_j$ heterozygous variants in a segment is modeled as the cumulative probability from a binomial distribution with $Y_j$ successes, the number of bases examined in the segment trials ($\eta_j$), and $P_{het}$ probability of success.

$$L(W, f \mid R_{B-min}, R_T, \eta_j) = \text{binomial}_{cmf}(\eta_j, R_T, P_{het})$$

A one-sided Fisher's exact test is used to calculate the likelihood of the association between the observed number of somatic variants called at positions of known germline variants. This serves as a penalty for the model misclassifying somatic variants as germline.

To determine the optimal number of clonal variant groups, a penalty term is added to the sum of the log likelihoods to compare models with different numbers of parameters.

n. Somatic Variant Calling of the Single-Sample Approach

The single-sample somatic variant calling model assumes that reads at a given position were generated based on one of four mutually exclusive models: somatic mutation (S), germline heterozygous ($G_{AB}$), germline homozygous ($G_{AA}$), or other (O). The probability of the data given each of the models is calculated using the expected allelic fractions for each type of variant.

$$P(D/S) = \max_{i=1...k}(\text{betabinomial}_{pmf}(R_B, R_T, \min(W_i \Phi_{ij}^S, W_i(1 - \Phi_{ij}^S)), \max(W_i \Phi_{ij}^S, W_i(1 - \Phi_{ij}^S)));$$

$$P(D/G_{AB}) = \text{betabinomial}_{pmf}(R_B, R_T, W_i^* \Phi_{ij}^G, W_i(1 - \Phi_{ij}^G));$$

$$P(D/G_{AA}) = \text{betabinomial}_{pmf}\left(R_A, R_T, W_i^*\left(1 - 10^{\frac{-Q_B^b}{10}}\right), W_i * 10^{\frac{-Q_B^b}{10}}\right);$$

$$P(D/O) =$$

$$\text{betabinomial}_{pmf}\left(R_T - R_A - R_B, R_T, W_i^*\left(1 - 10^{\frac{-Q_B^b}{10}}\right), W_i * 10^{\frac{-Q_B^b}{10}}\right).$$

The prior probability of a somatic mutation is based on the count of mutations in that position in cosmic (ω), and the prior probabilities of the germline genotypes are based on population allele frequencies ($F_A$, $F_B$).

$$\pi_S = \rho*(\omega+1);$$

$$\pi_{AB} = (2*F^*_A*F_B)*(1-\pi_S);$$

$$\pi_{AA} = F_A^{2}*(1-\pi_S);$$

$$\pi_O = 1-\pi_S-\pi_{AB}-\pi_{AA}.$$

We can then calculate the posterior probability that the mutation is somatic.

$$P(S/D) = \frac{P(D/S)*\pi_s}{P(D/G_{AA})*\pi_{AA} + P(D/G_{AB})*\pi_{AB} + P(D/S)*\pi_s + P(D/O)*\pi_O}. \quad (4)$$

If the posterior probability is <0.5 for somatic, germline, and homozygous, no call will be made.

o. Somatic Variant Calling of the Multi-Sample Joint Approach

The probability of observing the read counts in each sample (k) given that the variant is somatic ($P(D_k|S)$), germline heterozygous ($P(D_k|G_{AB})$), germline homozygous ($P(D_k|G_{AA})$), or another genotype ($P(D_k|O)$) are calculated as previously described. The prior probabilities are also calculated as previously described. The product of the conditional probabilities across the set of samples gives the joint probability of each variant type, given all the samples' data. The posterior probability that a position has a somatic variant given all the samples' data is calculated as shown below.

$$P(S|D) = \frac{\prod_{k=1}^{J} P(D_k|S)*\pi_S}{\prod_{k=1}^{J} P(D_k|G_{AA})*\pi_{AA} + \prod_{k=1}^{J} P(D_k|G_{AB})*\pi_{AB} + \prod_{k=1}^{J} P(D_k|S)\pi_S + \prod_{k=1}^{J} P(D_k|O)*\pi_O}$$

For each variant called somatic, it is determined whether there is evidence of the variant in each sample. For a variant to be called "somatic detected" in a sample, there must be at least one read supporting the variant in that sample, and the conditional probability of that sample's data, given that the variant is somatic, must be greater than the conditional probability of the sample's data given that the variant is homozygous.

If the posterior probability is <0.5 for somatic, germline, and homozygous, no call will be made.

Example 2. The Dependence of Private Germline Variation on Ancestry

Current approaches for filtering out germline variants from potential somatic variants typically include a comparison to databases containing large numbers of germline variants. Private germline variants are difficult to distinguish from somatic variants when a constitutional sample from the same individual is not available. Private variants are not present in polymorphism databases, so they may not be easily filtered out.

Figure 10A:
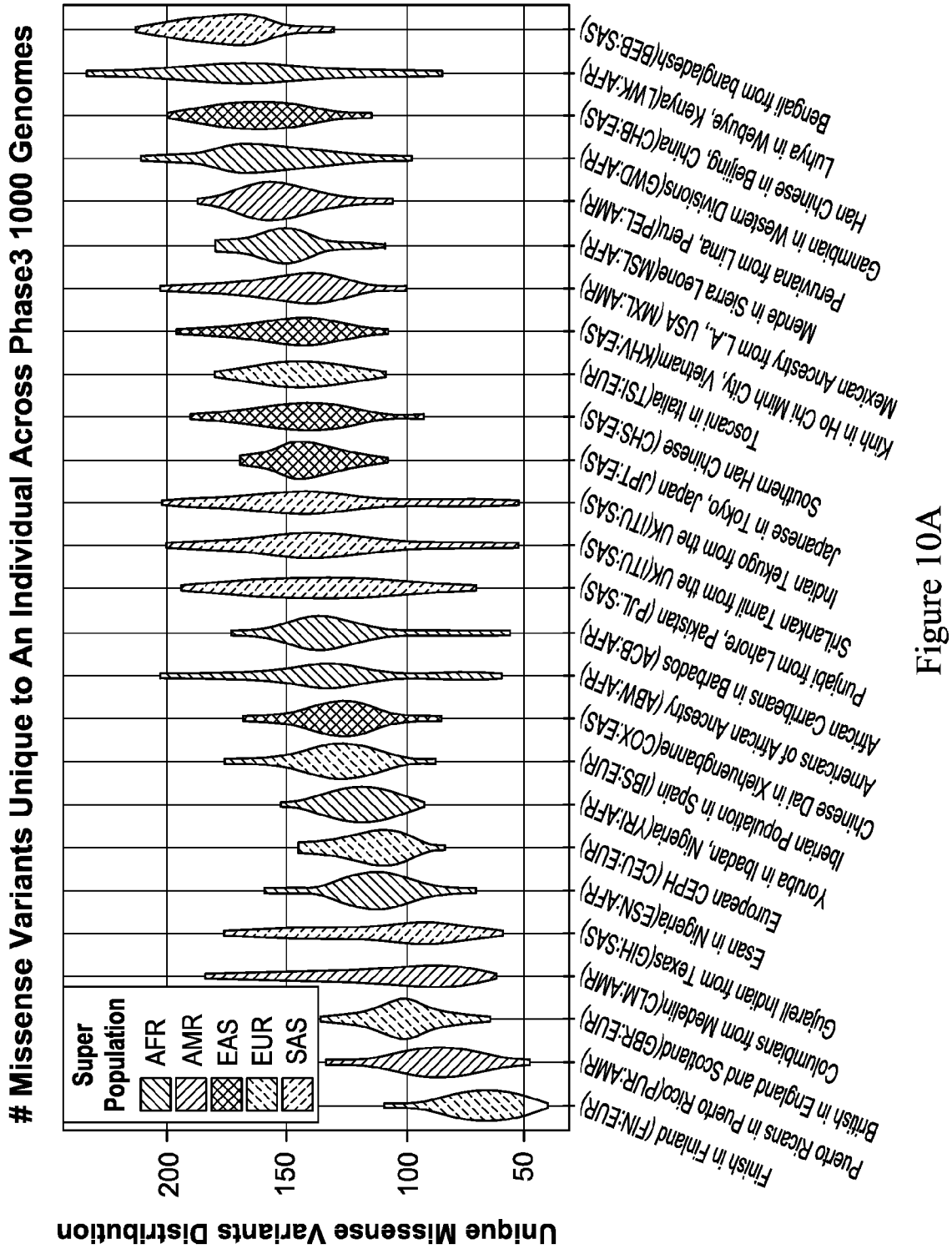
Figure 11:
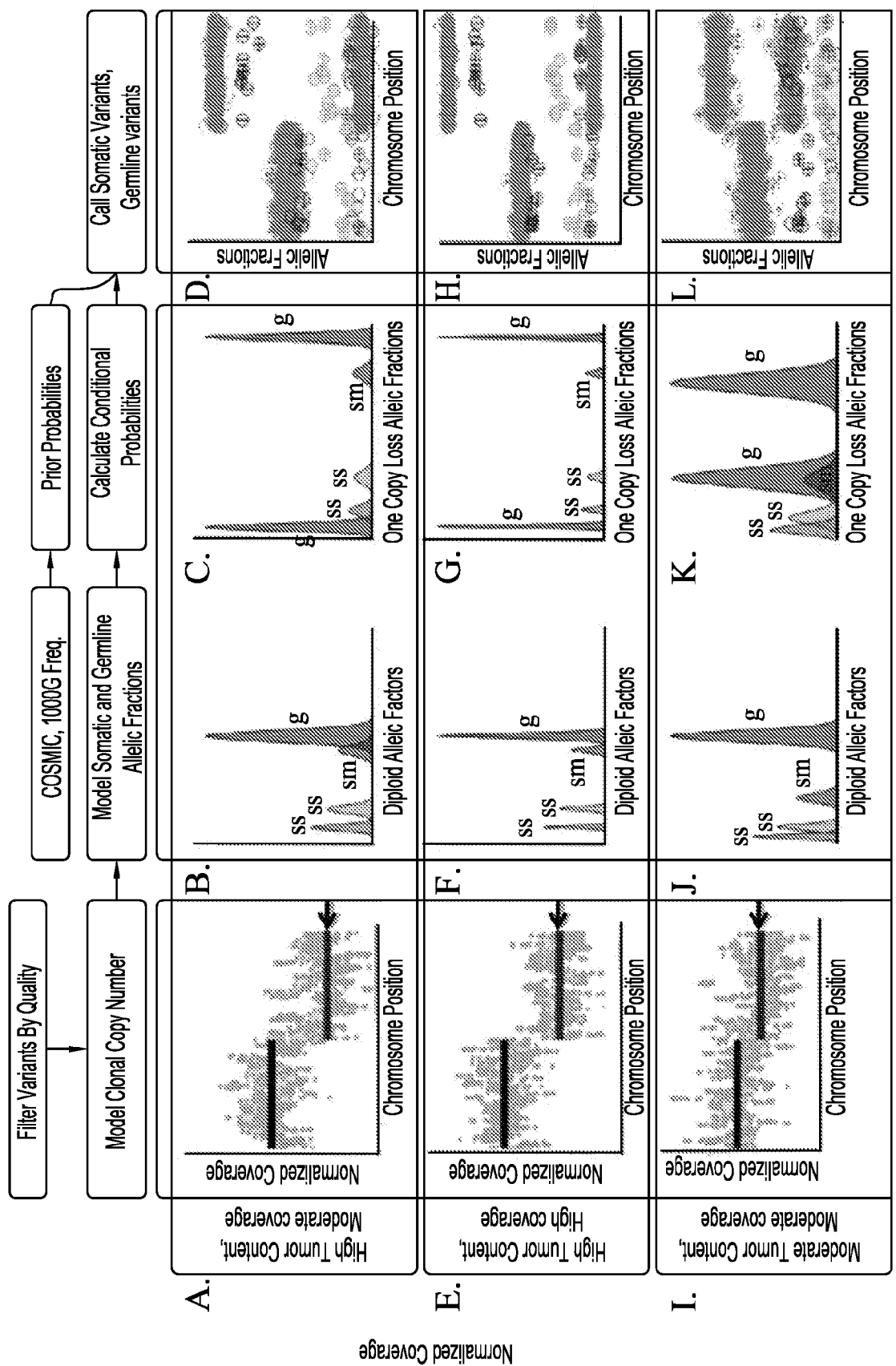
FIGS. 11A-11L Overview of variant calling strategy of the single-sample approach. After filtering candidate variant positions by quality, an EM approach is used to fit a model of clonal allelic copy number.

A recent study has shown increased false positive germline variants in non-Caucasians[18]. The 1000 genomes project found more novel variants in populations of African ancestry compared to those of European ancestry[20]. We would also expect there to be differences in the number of private germline variants between populations of different ancestry. We first sought to examine the dependence of private germline variation on ancestry independent of prior databases by utilizing 1000 Genomes Phase 3 data on 26 different populations (FIG. 9A). In this analysis, for each of the 2503 individuals, germline variants were counted as private if the variant was found in no other individual within phase 3 of 1000 Genomes. FIG. 10A shows the distribution of missense variants unique to each individual across the 26 different cohorts. Populations such as Bengali from Bangladesh (BEB) show a significant number of private and rare variants due to both the uniqueness of this population within 1000 Genomes and rapid recent population expansion. In particular, for the BEB population, there is considerable evidence the ability to precisely distinguish germline and somatic variation would require significantly greater numbers of sequenced individuals than the Finnish population. Evident from the violin plots, admixed populations show a bimodal distribution such as in Americans of African Ancestry in the southwest United States (ASW) indicating a high degree of variability. As expected, some populations show a smaller number of unique variants consistent with their geographic isolation such the Puerto Rico participants (PUR).

The analysis is extended by utilizing an additional set of 578 exome sequenced tumor/normal sets not previously included in existing databases. To obtain high quality variant calls, strict thresholds were used (increasing marginally false negatives), by excluding genes in highly homologous and paralogous regions, requiring greater than 20× coverage and that they were called by two different germline variant callers (GATK Haplotype Caller and FreeBayes). In this analysis, we limited to single nucleotide variants that have a defined impact on protein transcription or translation, and not found in Phase 3 of 1000 Genomes Phase 3, ExAc 3.0, ESP6500, or ARIC 5600 cohorts. Overall, we find approximately 100 to 200 private variants per individual. We then overlaid ancestry by PCA on common coding variants ascertained from exome sequencing of germline. These are summarized in FIGS. 10B and 10C which show there are significantly greater challenges in removing germline false-positives for many populations of non-European ancestry. First, shown in FIG. 10B, the number of private putatively functional variants for each individual are plotted in a bubble graph (FIG. 10B) for the 2nd and 3rd principal components to distinguish non-African samples. The number of private variants for each individual is shown both by color and by size In FIG. 10B, and the locations of individuals from 1000 Genomes are shown for orientation. Importantly, this resolution of ancestry shows that even within a European ancestry cohort, there are many individuals who still will have a high number of private variants that would result in a higher number of false positives when detecting somatic variants in tumor only samples by filtering. This effect is shown in the 3 areas of FIG. 10B by grouping individuals heuristically, sectioning off those that cluster near European 1000 Genomes (EUR) for one cluster, those near African 1000 Genomes (AFR) individuals for a second cluster, and those near Eastern and Southern Asian individuals in 1000 Genomes (SAS/EAS). Examining the mean number of missense variants separating into three approximate groups, FIG. 10B shows individuals clustering with those of European ancestry with a mean of 101 private missense variants, individuals clustering or admixed with individuals of African ancestry with a mean of 108 missense variants, and those clustering with individuals of South or East Asian ancestry show a mean of 117 missense variants. A 1-way ANOVA analysis between these groups shows significant differences in the number of private variants (p<0.003). These results are overall consistent both within 1000 Genomes populations and within individuals not included with existing databases, showing that individuals of non-European ancestry have greater number of private variants per individual. Still, the wide distribution of individuals of Caucasian ancestry indicates that ancestry alone, as driven by common variation, does not explain all of the variation. Likely admixture with individuals from populations that have recently undergone rapid expansions indicates there is considerably heterogeneity within populations. Taken together, these results are consistent with a lack of diversity being a major but not the exclusive factor in the higher number of private variants for individuals of non-European descent. Additional population factors may also affect the number of private variants identified. For example, in populations have undergone recent expansions, a larger number of variants may be present only within the most recent generations.

The observation that most non-hypermutated cancers have approximately the same number of somatic mutations (~100) as private germline variants has significant implications towards using tumor only sequencing in precision medicine. In FIG. 10C, the European group 1 would have an approximate 50% false discovery rate with filtering alone, whereas the African group would have over a 70% false discovery rate. The results shown in FIGS. 10A-10C suggest filtering-based approaches are substantially more effective for European American individuals. Notably, the results show that the number of private variants is dependent on ancestry. Underlying these differences are undersampling of some populations within databases along with population-specific characteristics, such as admixture or populations that have recently undergone rapid expansions. Since using databases does not appear sufficient to filter germline variants from tumor-only somatic variant calls, we examine integrating variant allele frequency information.

Example 3. Framework for Considering Allele Fraction Shifts as a Function of Copy Number and Clonal Heterogeneity Since somatic variants will only occur in tumor cells, but germline variants will occur in all cells, we can leverage differences in allele frequencies to differentiate between somatic and normal variants in impure tumor samples. In solid tumors, stromal cells and infiltrating lymphocytes are typically interspersed among the tumor cells[46,47]. The normal cell contamination in tumors can be leveraged to differentiate somatic from germline variants. For example, in a normal diploid region, a heterozygous germline variant should have an allele frequency around 50% while a heterozygous somatic mutation in an impure tumor should have a lower allele frequency. Still, tumors often have many copy number alterations that will affect the expected allele frequencies of both germline and somatic variants. One approach, implemented by Smith et al., is to fit the distribution of allele frequencies of common germline variants in each segment and detect outliers as likely somatic variants[19]. In the present subject matter, the allelic copy number and clonal sample fractions are modeled in order to examine how these factors impact the power to detect somatic variants. A conceptual overview of the present approach is shown in FIGS. 11A-11L and a more detailed illustration is provided in FIG. 4.

A key aspect of the present method is modeling the clonal and subclonal allele-specific copy number alterations, which can also affect the allele frequencies of both somatic and germline variants. The expected allele frequencies can be calculated (see methods Eqs. 1 and 3). FIG. 3 illustrates how the expected allele frequencies for somatic and germline differ with tumor content for different copy number alterations. As predicted, the biggest differences in allele frequencies between the somatic and germline variants occur at the lowest tumor content regardless of copy number state. In a normal diploid region, the difference in allele frequencies monotonically decreases as tumor content increases. However, other copy number states result in points of intermediate tumor content where the allele frequencies for somatic and germline variants are similar. Therefore, we would expect copy number alterations to make it more difficult to detect somatic variants based on allele frequencies.

Example 4. Simulations of the Single-Sample Approach

Figure 12:
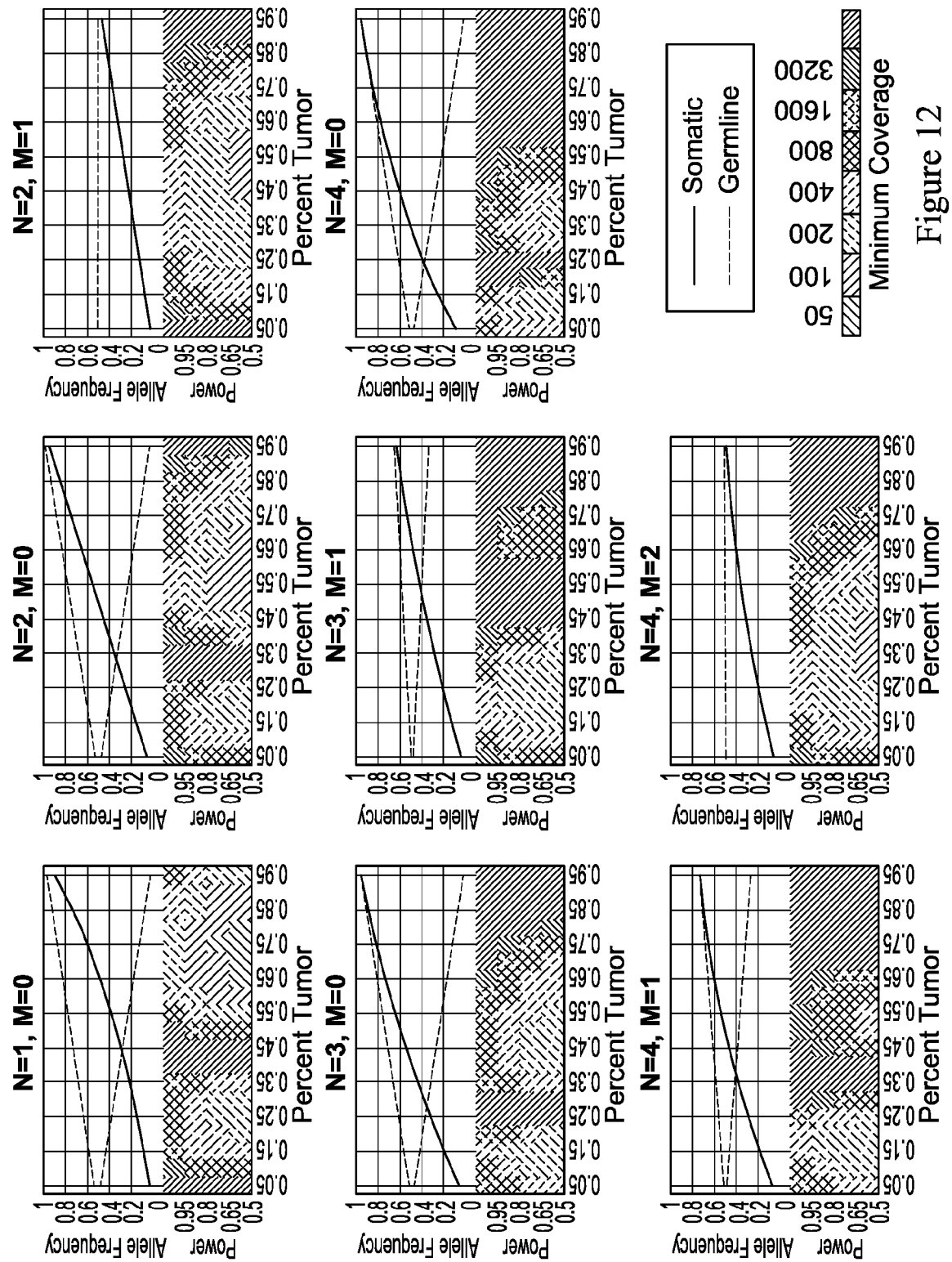
FIG. 12 Allele frequencies of somatic and germline variants and required coverage for somatic variant detection by simulation. (Top Halves of Each Panel) The expected allele frequency of somatic (blue) and germline variants (red) by tumor content (x-axis) and copy number states (plot titles). (Bottom Halves of Each Panel) The coverage required (indicated by the color) to get the detection power (y-axis). Black squares indicate that the detection power was not achieved even at the highest coverage evaluated. The closer the somatic and germline allele frequencies, the more difficult it is to detect somatic variants.

It was expected that at higher read depth, allele frequency could be measured more precisely, therefore would be better able to detect somatic variants. The read depth required should depend on the tumor content and the copy number state. Simulations were used to examine how the power to detect somatic variants depends on tumor content, mean target coverage, and copy number state. Somatic variants were simulated in eight different copy number states, with sample fraction from 5-95% and mean target coverage from 50 to 3200 with 1000 variants for each condition. Then we found the percentage that would be called somatic using the default thresholds. FIG. 12 shows that the read depth required depends greatly on the sample fraction and copy number state. In a diploid region (N=2, M=1), we would only need 200× mean target coverage to detect almost 80% of the somatic variants with a sample fraction of 50%. However, we would need 800× mean target coverage to detect a similar proportion of variants with a sample fraction of 75%, and 3200× coverage to detect a similar proportion of variants with a sample fraction of 85%. Copy number alterations reduce the power to detect somatic variants in specific ranges of sample fractions. For example copy neutral loss of heterozygosity (LOH) (N=2, M=0) makes it very hard to detect variants with a sample fraction around 35-40%, while a one copy gain (N=3, M=1) makes it very hard to detect variants with a sample fraction around 50-55%.

Thus, the sensitivity of the allele frequency strategy is highly dependent on the tumor content, the copy number alteration profile of the sample, as well as the sequencing depth. A minimum sequencing depth of 200-400× is needed with even higher depth required for samples with high tumor content.

Example 5. Evaluation Dataset

A set of nine samples consisting of two glioblastoma samples and seven triple negative breast cancer samples were used to evaluate the tumor only caller. These included four African Americans, three European Americans, one Ghanaian, and one Hispanic. One of the glioblastoma samples was sequenced to 2101× mean target coverage for downsampling and in silico dilution experiments. The other samples were sequenced to 454x-1012x mean target coverage. A consensus calling approach was used to define true somatic and true germline variants, as consensus calling typically outperforms any individual caller[48]. Using strict criteria of detection by three out of three somatic variants callers (or two out of two for indels) it was found that each sample had an average of 129 somatic (range 75-196) mutations. Three out of three consensuses calling was used to define germline variants, and considered variants private those that did not appear in dbSNP. By these strict criteria, an average of 224 (range 126-319) private germline variants per sample were found.

Example 6. Variant Quality Filtering

Figure 13:
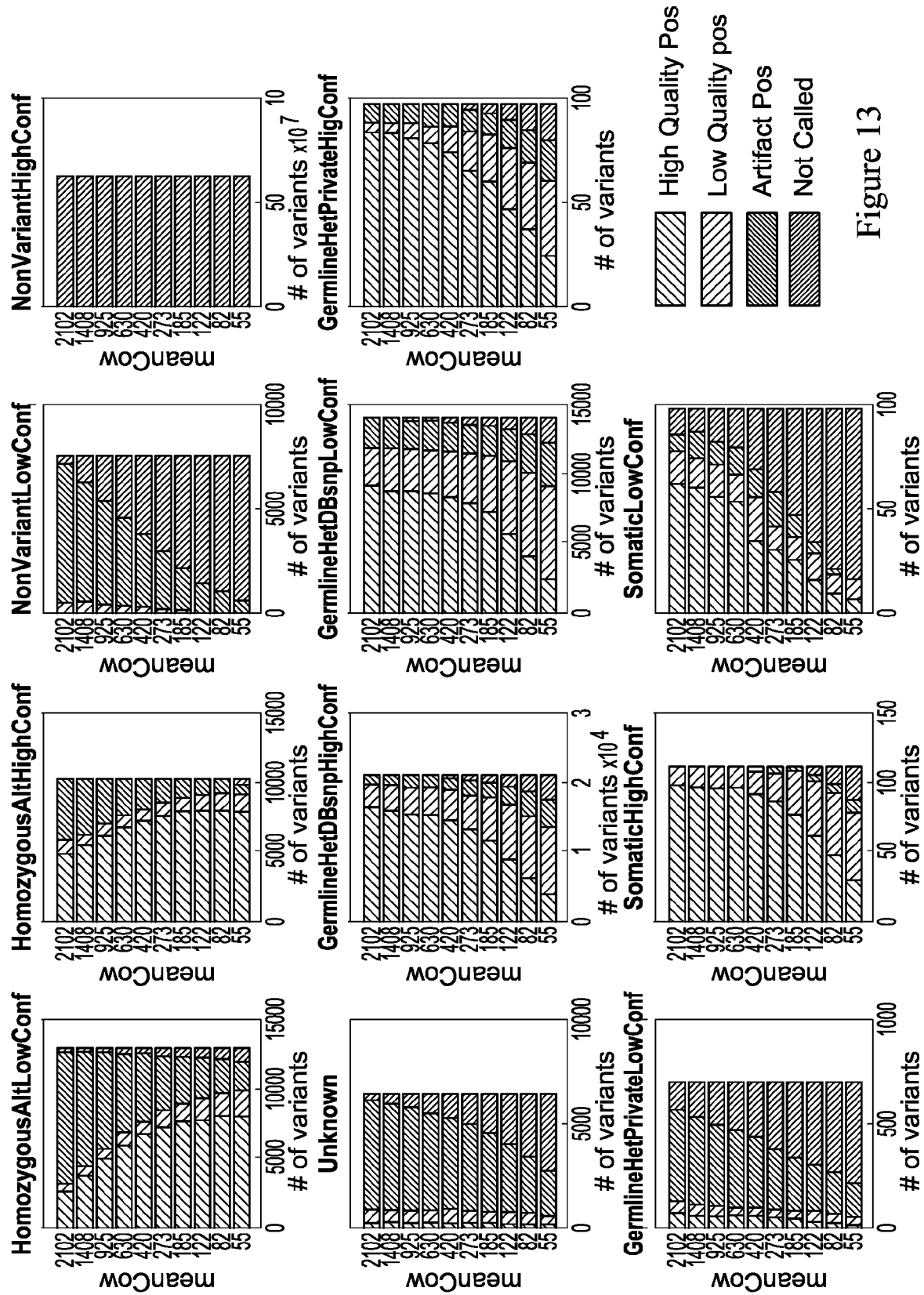
FIG. 13 Variant Quality Filtering By Sample. The number of variants of each type in each quality filtering category. Each graph represents a variant type, each bar represents a sample, and the color of the bar represents the number of variants in each quality category. High-quality positions have a PT>0.99. Low-quality positions have a PT<0.99 but PV>0.99. Artifacts have a PV<0.99. Nonvariants are not considered by the tumor only caller (NaN).
Figure 14:
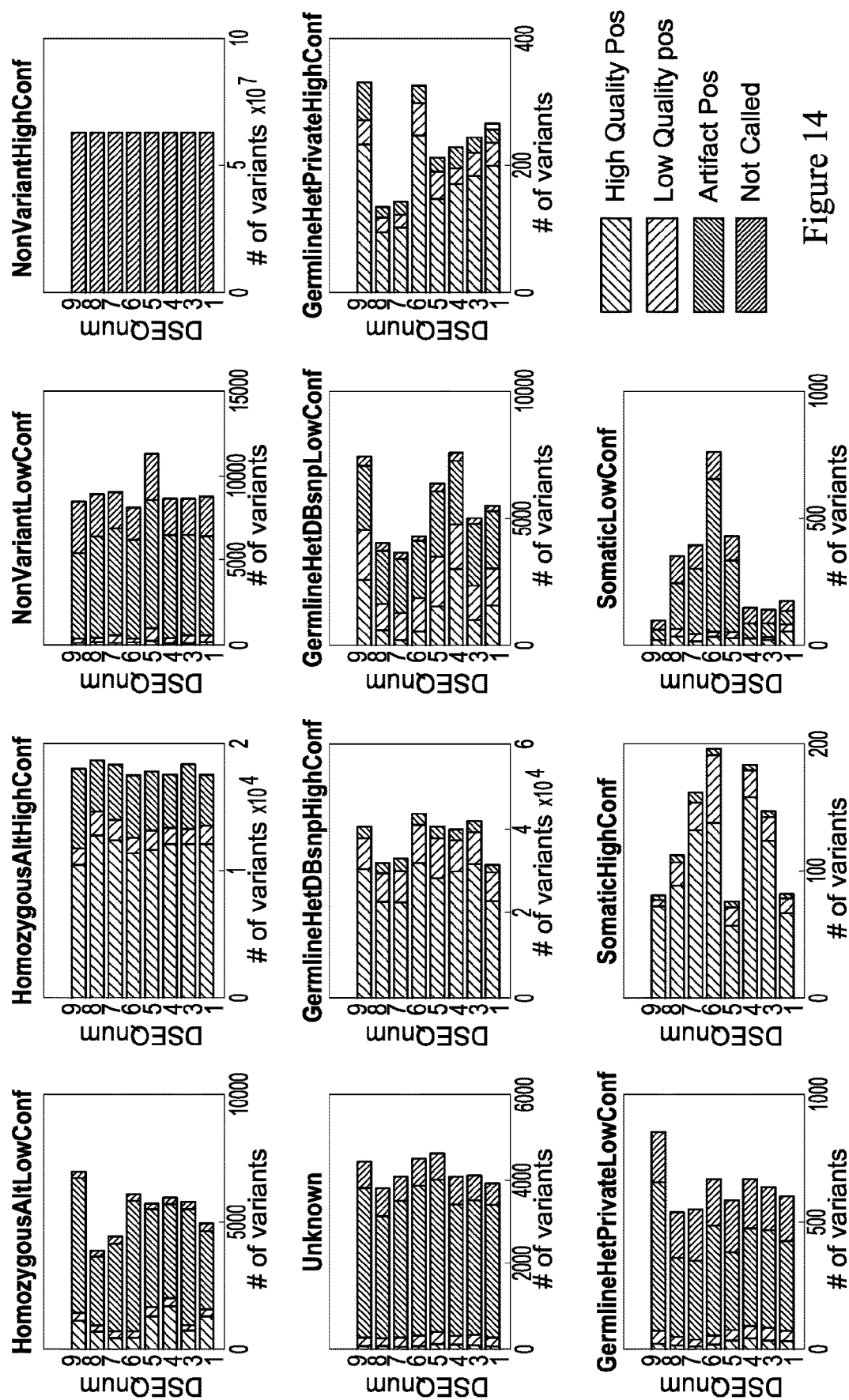
FIG. 14 Mapping coverage as a function of variant calls.
Figure 15:
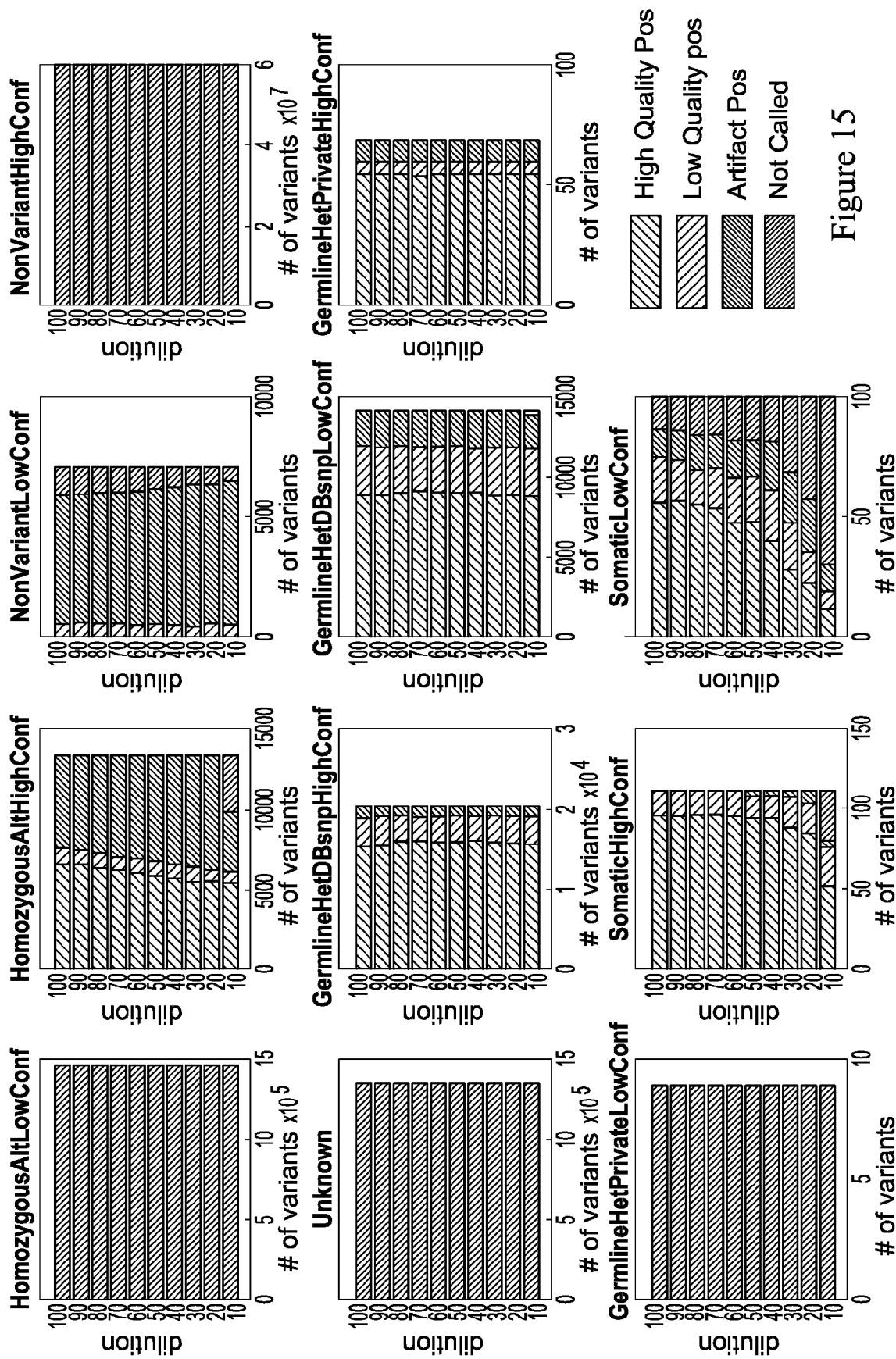
FIG. 15 Variant Quality Filtering Across Dilutions. Shows the number of variants of each type, in each quality filtering category. Each graph represents a variant type, each bar represents a dilution, and the color of the bar represents the number of variants in each quality category. High-quality positions have a PT>0.99. Low-quality positions have a PT<0.99 but PV>0.99. Artifacts have a PV<0.99. Nonvariants are not considered by the tumor only caller (NaN).

Strict quality filtering is used to exclude variants that are not mapped cleanly because any mapping artifacts may shift the measured allele frequency and result in an incorrect classification. Therefore, the present method adopted a two-tiered approach to variant quality filtering. About 80% of somatic variants and 78% of private germline variants have sufficient quality to call (FIG. 13). A much lower percentage of indels meet the strict quality criteria as they are much more difficult to map. It was found that increasing coverage increased the number of somatic and private germline variants that pass the strict quality criteria (FIG. 14) while changing the tumor content has little effect (FIG. 15).

Figure 16:
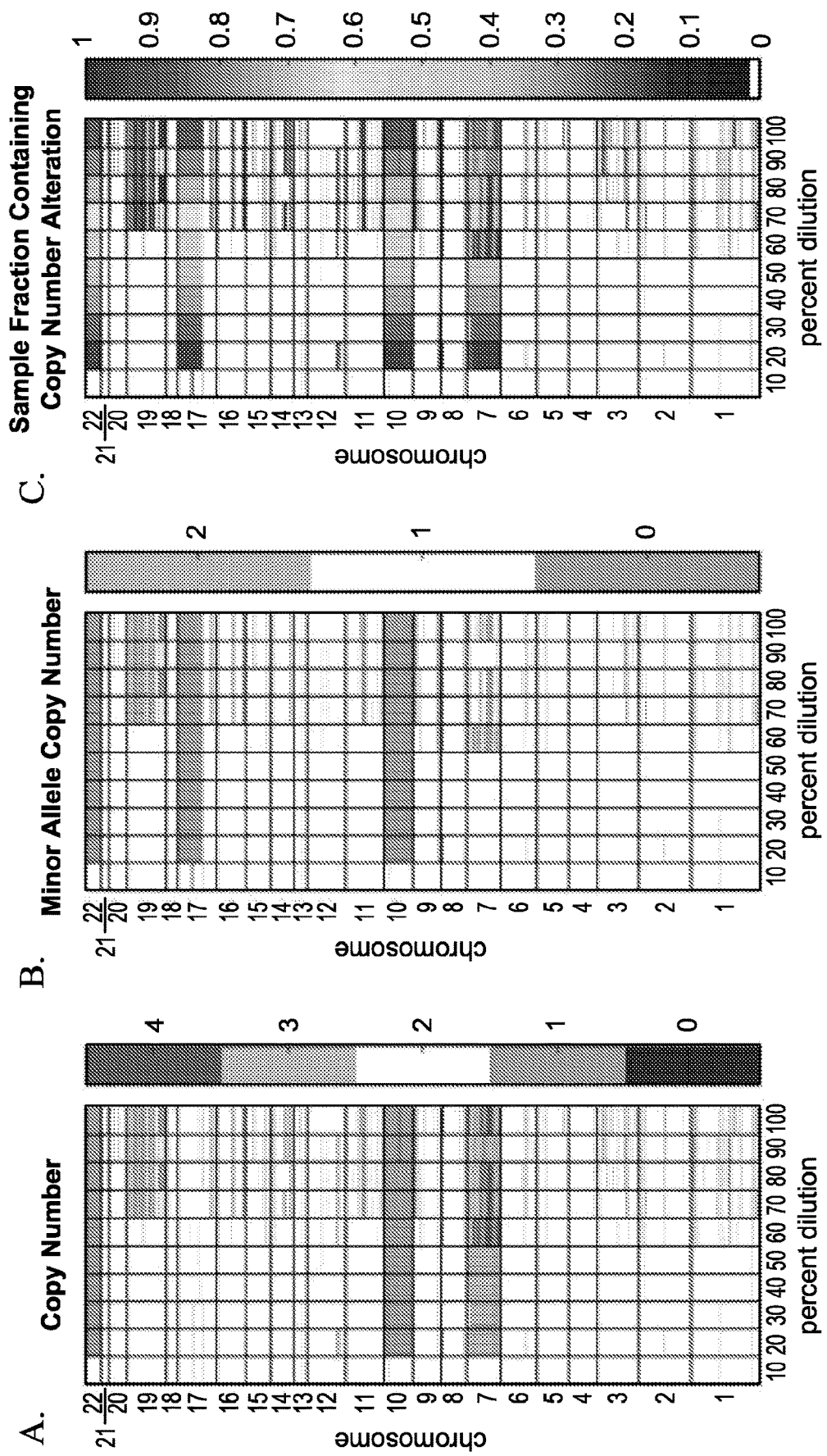
FIGS. 16A-16C Copy Number and Sample Fraction Across Dilutions. The copy number (FIG. 16A), minor allele copy number (FIG. 16B), and sample fraction of the copy number events (FIG. 16C) are plotted as heatmaps.
Figure 17:
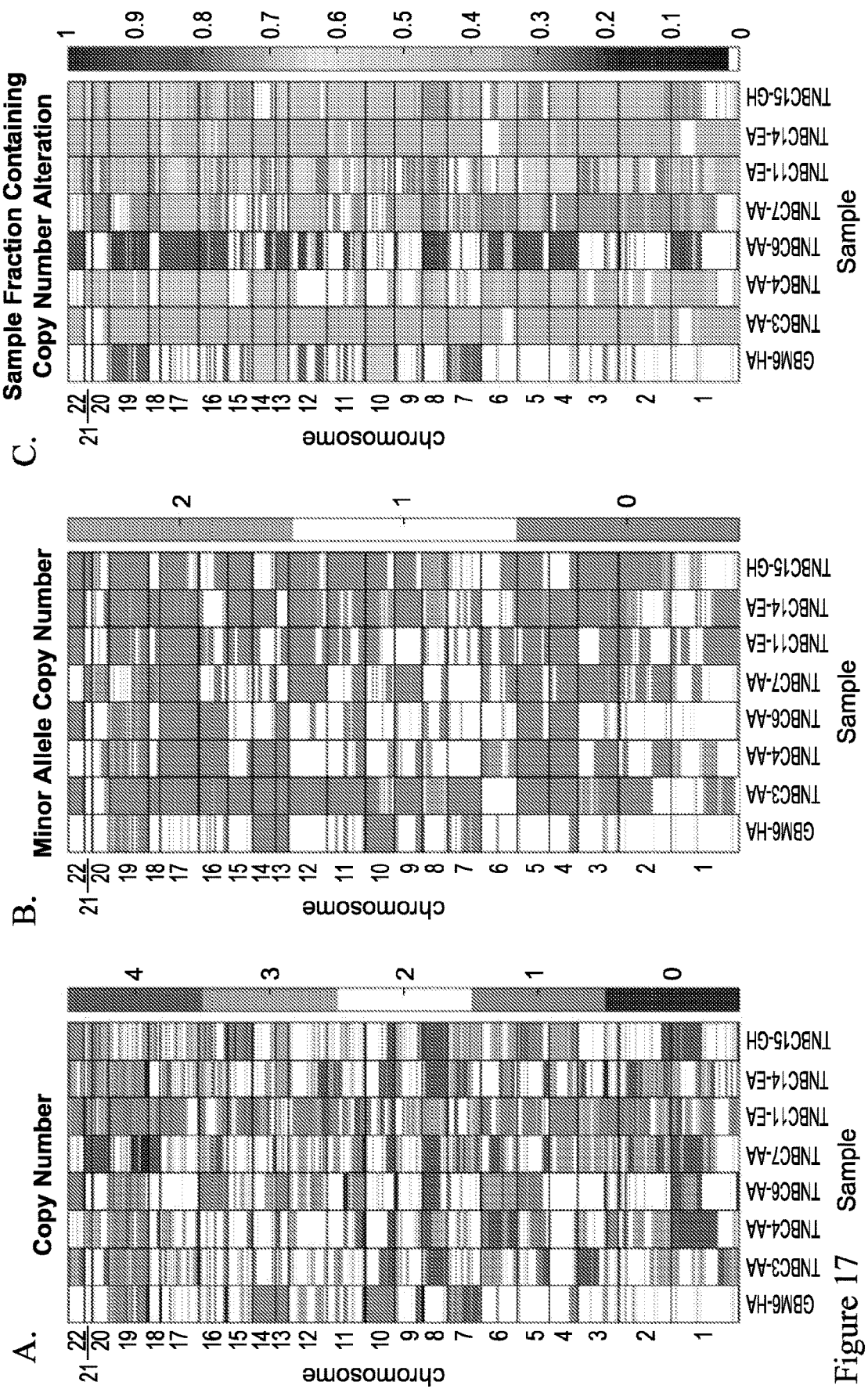
FIGS. 17A-17C Copy Number of and Sample Fractions Across Sample Set. The copy number (FIG. 17A), minor allele copy number (FIG. 17B) and sample fraction of the copy number events (FIG. 17C) are plotted as heatmaps.
Figure 20:
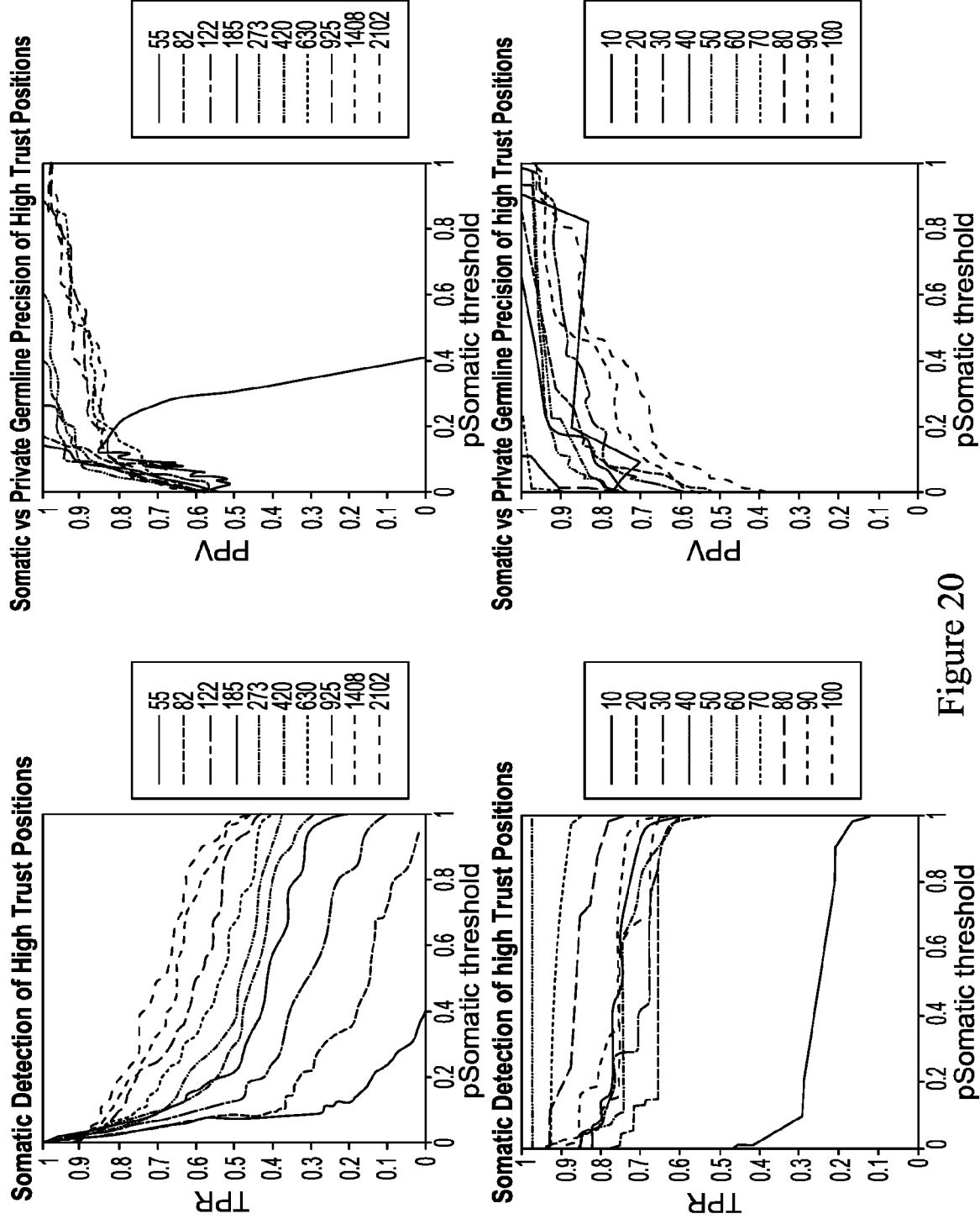
FIGS. 20A-20D Effect of Threshold on Sensitivity and Precision. The true positive rate (FIGS. 20A and 20B) or positive predictive value (FIGS. 20C and 20D) is plotted against the pSomatic threshold. Each line represents different mean target coverage (FIGS. 20A and 20C) or dilution (FIGS. 20B and 20D). Only high trust true somatic or private germline variants are included in the graphs shown in FIGS. 20A-20D. As expected, the sensitivity decreases with the threshold, but the positive predictive value increases. It was found that higher coverage results in better sensitivity, but lower positive predictive value. At higher coverage, the threshold may be increased to improve the positive predictive value with less loss sensitivity.

Example 7. Sample Fraction and Copy Number Calling of the Single-Sample Approach In the downsampling and in silico dilution experiments, the main copy number events were found to be are consistently called, except for at the lowest dilution (FIGS. 16A-16C). For the one copy loss and LOH events, the sample fraction decreases linearly with the dilution as expected. In the present approach, some ambiguity was observed in calling segments as a one copy gain in the highest sample fraction or a higher level gain in a lower sample fraction. Though too small to see in the plot, there is also a ~0.2 megabase deletion on chromosome 9 that is detected as a two-copy loss in all but the lowest dilution encompassing CDKN2A. The triple negative breast cancer (TNBC) samples show a large number of gains and losses (FIGS. 17A-17C). A large number of copy number alterations are evidence of genome instability which is typical of triple negative breast cancer[49].

Example 8. Somatic Variant Detection Sensitivity of the Single-Sample Approach Only polymorphic variants appearing in dbSNP are considered false negatives in the filtering approach since the same callers were used to define the truth set, so the sensitivity of the filtering approach does not represent the sensitivity of the callers. There were an average of 16 somatic variants found in dbSNP per sample (range 6-28). LumosVar's sensitivity varies greatly between samples (FIGS. 18A-18B). The power to detect somatic variants was expected to depend on the sample fraction, copy number states, and read depth. Using the sample fraction and copy number state assigned to each variant, we simulated somatic variants and determined the proportion of simulated somatic variants that would be called somatic by our model (FIGS. 19A-19B). These simulations can predict accurately the proportion of somatic variants that can be detected, which indicates that the samples with poor sensitivity have copy number states and sample fractions that are not conducive to detecting somatic variants by allele frequency. As expected, the sensitivity to detect somatic variants increased with coverage (FIGS. 18A-18B). Also consistent with expectations, the detection sensitivity was best at intermediate tumor content, where the somatic variants would generally have the biggest difference in expected allele frequency from the germline variants (FIGS. 18A-18B). The caller threshold can be adjusted to tune the tradeoff between sensitivity and precision (FIGS. 20A-20D).

Example 9. Somatic Variant Detection Precision of the Single-Sample Approach All of the private germline variants are called as false positives in the filtering approach. Because the number of private germline variants varies by ancestry, the positive predictive value of the filtering approach also depends on ancestry. For the samples of European American ancestry, the positive predictive value of the filtering approach ranges from 35 to 62%, while the samples of Hispanic, African American, or African ancestry the positive predictive value of the filtering approach ranges from 20 to 40%. The single-sample approach, LumosVar, can correctly classify most of the private germline variants and has much better positive predictive value (range 67-91%). While there still are some false positive germline variants, many are found in dbSNP (FIG. 12). Combining the filtering approach with the tumor only caller could further improve the positive predictive value.

LumosVar uses information in addition to databases to help infer what is somatic and what is germline. Specifically, the fraction of reads that show variant can be used to determine whether the variant is somatic or germline. The tumor samples may vary in tumor-cell contents, but the LumosVar approach works best when the sample contains normal tissue and tumor tissue (e.g., the sample is not 100% tumor tissue). If the sample has very little normal tissue (e.g., ~95% tumor and ~5% normal tissue), then the small amount of normal tissue may not justify the cost and effort of performing the LumosVar analysis in some situations.

There are often logistical reasons why only a tissue sample may be available, but the tumor tissue is often a mixture of tumor and surrounding stromal tissue. The present disclosure demonstrates that a model leveraging deep sequencing to measure differences in allele frequencies between somatic and germline variants could be utilized to call somatic mutations with greater specificity than using population variant frequencies alone. The disclosed allele frequency-based strategy can reduce by ⅔rds the number of false positives. The Bayesian calling strategy described here, along with appropriate sample collection and sequencing depth will enable the more accurate detection of somatic variants when the germline samples are not available.

The intuitive question moves to what is the accuracy of tumor only sequencing. It turns out accuracy is not the most informative statistical tool since one is assured 99%+ accuracy due to the millions of true negatives—even if one reports zero variants in a hypermutated sample. Positive predictive value is a natural tool, but it brings forth a different problem. In the case of tumor only sequencing, the positive predictive value for variants called somatic will depend on the number of true mutations. The number of mutations or mutational burden varies by cancer type. Hypermutated phenotypes often seen in melanomas, bladder, and lung cancer can be 100-times higher than the mutational burden scene in lymphomas. Recent data shows the importance of mutational burden as it correlates to the response to immune checkpoint blockade therapies[57]. Given the dependence of mutational burden on cancer type and the relationship between tumor-only false positives and ancestry, a more complex picture appears. In some cases, for some ancestries and some cancers can stack in favor of a low false discovery rate. For example, cutaneous melanomas have a higher a mutational burden and are more frequently found in individuals of European ancestry. However, acral melanomas have a low mutational burden and are much more frequently found in individuals of non-European descent (as compared to cutaneous). In this example, a melanoma of a person with non-European decent would show a very low positive predictive value and a European-American would have a higher positive predictive value.

We have demonstrated that LumosVar has improved positive predictive value in calling somatic variants compared to database filtering, which is the most commonly used approach with unmatched tumor samples. When analyzing archival samples in a research setting, LumosVar would be of great utility. In addition to calling somatic and germline variants, LumosVar also calls allele-specific copy number and assigns both mutations and copy number alterations to clonal sample fractions.

Overall, the results shown herein provide insight into how experimental design and sample characteristics can have a large impact on the sensitivity of the allele frequency based tumor only somatic variant detection. Moderate tumor content is optimal and could be achieved through strategic sectioning of FFPE blocks. High sequencing depth is also critical to sensitivity, and as the cost of sequencing continues to decline, high depth sequencing is becoming more common practice. The researcher cannot control the copy number alterations of a tumor but can be aware that cancer types that stray farther from diploid will be less amenable to this approach. Since different copy number alterations have tumor content where the somatic and germline variants are most difficult to distinguish, it could be valuable to sequence different sections of the same tumor that may have different tumor content.

The number of germline false positives detected in tumor only sequencing is dependent on the individual's ancestry. Our Bayesian framework, which integrates modeling copy number and clonality, can greatly reduce the number of germline false positives. The sensitivity of our approach depends on tumor purity, coverage, and copy number alterations. With appropriate experimental design, our approach has the potential to be useful for somatic variant calling when matched normal tissue is not available, particularly in individuals of non-European ancestry.

Example 10. Simulation of the Multi-Sample Joint Approach

Figure 21A:
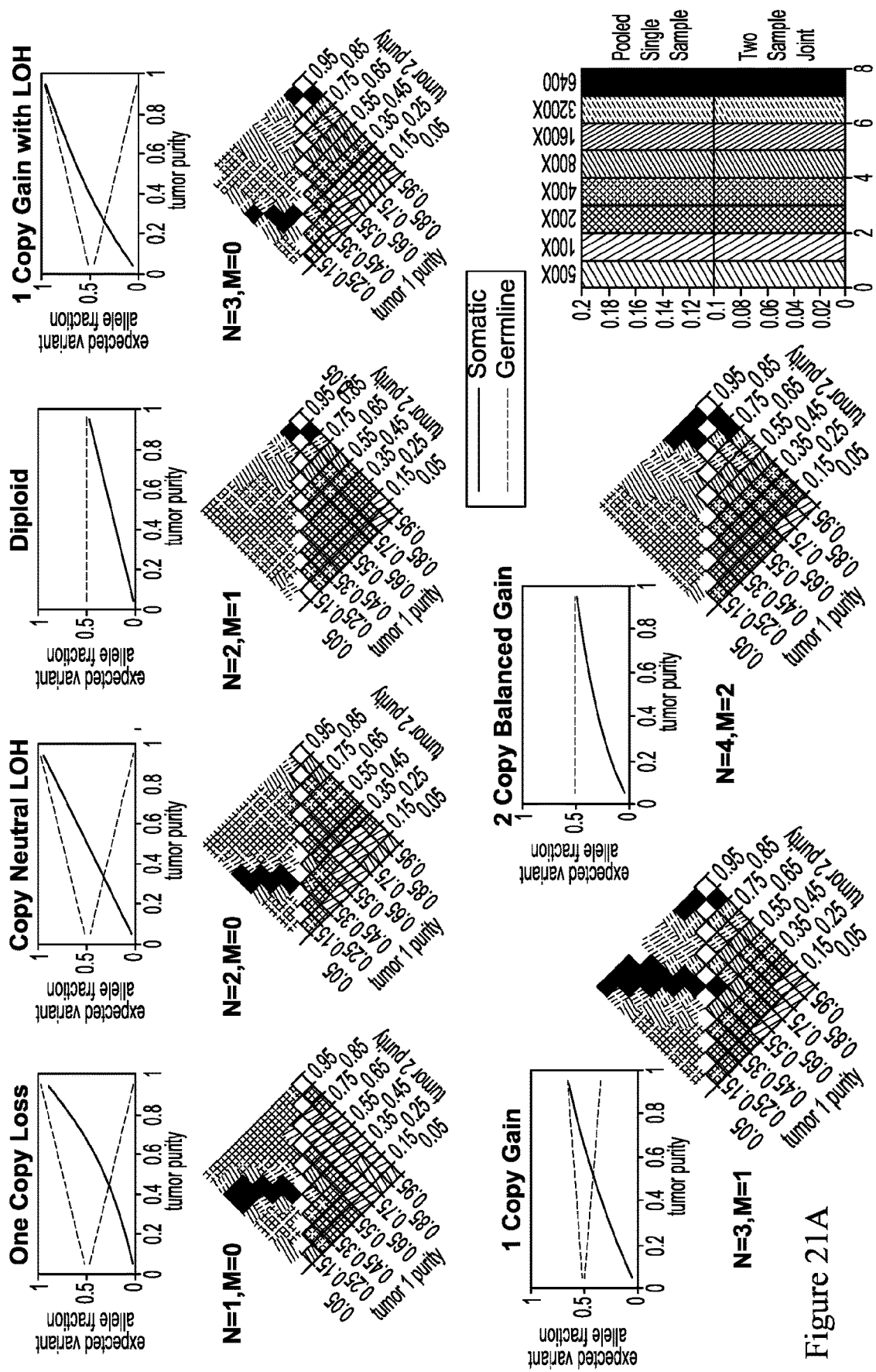

Simulations were performed to determine how the tumor purity and copy number states affect the power to detect somatic variants in the joint approach, and how the power compares to the single-sample lumosVar (FIGS. 21A-21B). As previously shown, the single sample approach performs best with a sample of intermediate tumor purity for variants in diploid regions, but copy number variation leads to situations where the expected somatic and germline allele fractions are similar, making it difficult to classify somatic variants using a single sample[15]. The joint approach mitigates this limitation, and only provides poor detection when both samples fall into a range where the expected somatic and germline allele fractions are very similar. The joint approach generally only requires low-to-moderate coverage when one sample has low tumor content and the other sample has moderate-to-high tumor content. Simulation studies suggest that a multi-sample approach should be more powerful than a single-sample approach, even if there is a small difference in tumor content between the two samples. For example, in a region of copy neutral LOH (N=2, M=0), our simulations show that analyzing a 25% tumor and 45% tumor sample jointly would require each to have 400× coverage to detect at least 80% of the variants. However, a single sample with 35% tumor in a region of copy neutral LOH would not enable the detection of 80% of the somatic variants even at 3200× coverage.

Evaluation of a set of GBM samples with low tumor content (from NE biopsies) and high tumor content (from CE resections) further demonstrates the sensitivity and precision of the joint approach. Practical application of this approach to a set of FFPE breast and prostate samples shows the feasibility of this approach with typical archival samples.

Compared to the single sample lumosVar analysis, the joint approach requires lower total sequencing coverage to obtain the same sensitivity. Based on the simulation studies, if the adjacent normal tissue has less than 25% tumor cell contamination, and the tumor sample has at least 55% percent tumor cells, then 200× total coverage (100× for each sample) is only required to detect 80% of the somatic variants that are in all of the tumor cells. However, higher coverage would be desirable to detect low abundance subclonal variants. Due to the large difference in prior probabilities of homozygous reference versus somatic variants in this model, lumosVar tends to be less sensitive to low abundance variants compared to other somatic variant callers. LumosVarMulti also has more stringent quality filtering than most paired somatic variant callers because the same artifacts often appear in the tumor and germline sample, so paired callers can eliminate those artifacts.

Example 11. Evaluation Dataset of the Multi-Sample Joint Approach

To evaluate LumosVarMulti, a glioblastoma dataset was used, where enhancing (high tumor content) and non-enhancing (low tumor content) samples were available for each patient, as well as the matched normal sample to define the true somatic variants. Results showed that both sensitivity and positive predictive value were improved by analyzing the high tumor and low tumor jointly compared to analyzing the samples individually or in silico pooling of the two samples. Finally, this multi-sample joint approach was applied to a set of breast and prostate archival FFPE tumor samples where normal samples were not available for germline sequencing.

It was hypothesized that the patterns of allelic fractions across samples of different purities would be more informative than any individual sample in distinguishing somatic from germline variants. To test this hypothesis we evaluate sequencing two samples of different purities from the same patient and calling the variants using the joint approach, compared to sequencing one sample at twice the sequencing depth and with a tumor purity that is the average of the two samples. First, simulations were used to systematically evaluate the effects of tumor purity and copy number states for the two approaches. Next, a set of glioblastoma (GBM) patient samples for which sequencing data was available for the contrast-enhancing region (CE, the high fraction of tumor cells) and non-enhancing region (NE, the low fraction of tumor cells) biopsies, as well as peripheral blood sample sequencing data, were evaluated to establish the truth. Finally, the method was applied to an archival cohort of breast and prostate samples where formalin-fixed paraffin-embedded (FFPE) sections from the tumor biopsies or resections were the only tissues available.

Figure 23A:
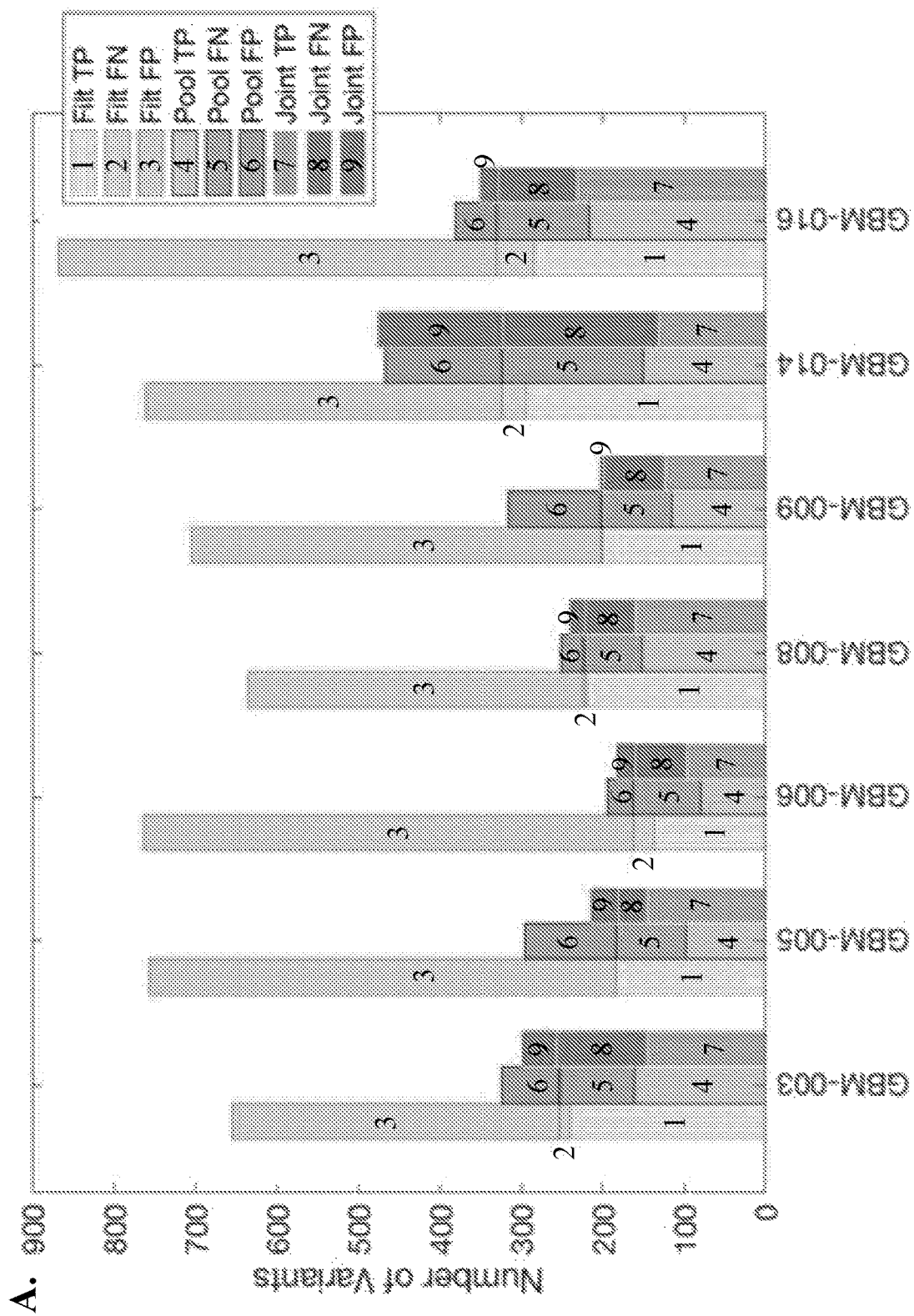
(FIG. 23A) To evaluate the lumosVarMulti approach on real data, patients that had sequencing available for two samples of different tumor content were identified. A filtering approach, where heterozygous germline variants not found in dbSNP were considered false positives, and somatic variants found in dbSNP were considered false negatives, was compared to lumosVar calls on pooled and joint analyses of enhancing and non-enhancing region biopsies. For each patient, the left bar represents the filtering approach, the middle bar represents the pooled approach, and the right bar represents the joint approach. Green (represented by number 1, 4, and 7) corresponds to the number of true positive variants detected (TP), blue (represented by number 2, 5, and 8) corresponds to the number of true somatic variants that were not detected (false negatives (FN)), and red (represented by number 3, 6, and 9) corresponds to the number of false positive variants detected using each approach (FP).

The potential benefit of sequencing two samples of different purities from the same patient and calling the variants using the joint approach was evaluated. A set of previously collected and de-identified exome data from seven recurrent lioblastoma (GBM) patients was used (FIG. 22, FIG. 23). Each patient dataset contained exome sequencing data for contrast-enhancing (CE, high fraction of tumor cells) region biopsies, non-enhancing (NE, low fraction of tumor cells) region biopsies, and peripheral blood sample (germline) sequencing data to establish truth. The acquisition and sequencing of these samples was previously described[58]. The consensus of three comparative somatic variant callers (SEURAT[40], STRELKA[41], and MUTECT[42]) was used to define the true somatic variants. The number of likely germline false positives were determined based on the number of heterozygous variants called by Haplotype-Caller[37] that were not found in dbSNP[44]. The percent tumor cells of total cells in the sample was determined by the log2 fold change of a large chromosome segment appearing to have loss of one copy (typically chromosome 10). Thus, the results further demonstrated the sensitivity and precision of the joint approach.

Figure 24:
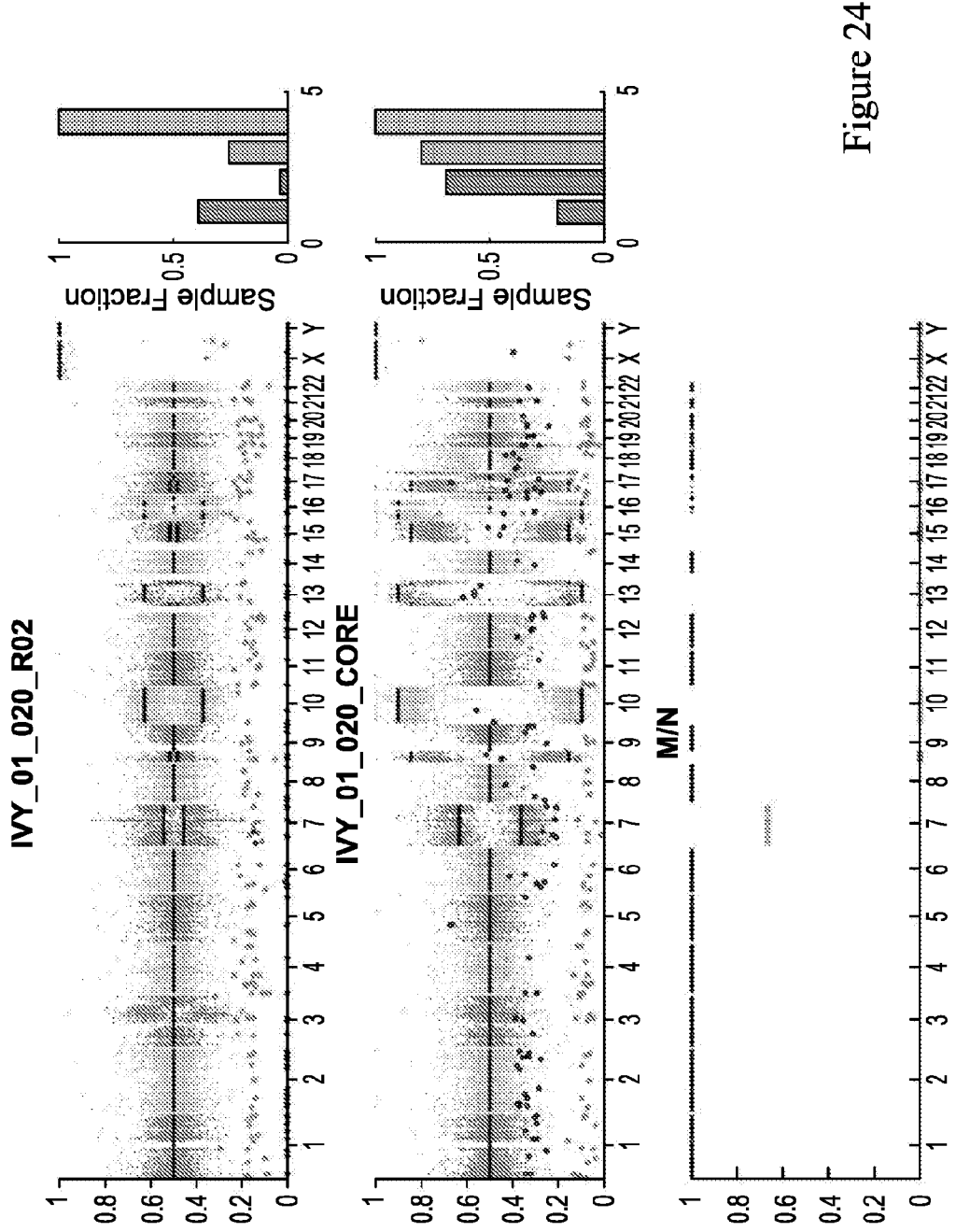
FIG. 24 Variant allele fractions are plotted for a non-enhancing region (low tumor content—top plot) and enhancing region (high tumor content—middle plot) samples for a gbm patient. The gray and brown dots represent germline variants. The blue, red, and green dots represent clonal groups of somatic variants. The blue variant group is found at a moderate sample fraction in the non-enhancing sample and a low sample fraction in the enhancing, the red variant group is at a very low in the non-enhancing sample and high in the enhancing sample, and the green variant group is low in the non-enhancing sample and high in the enhancing sample. The black lines show the expected allelic fraction of germline variants for each segment. The bottom plot shows the minor allele to total copy number ratio for each segment, and the color indicates the clonal variant group of the copy number alteration. Orange indicates germline copy number state is not diploid for X and Y as the patient is male.

The joint approach methods were applied to archival breast cancer and prostate samples, where only FFPE tissue sections from biopsies or surgical tumor resections were available (FIG. 24). For eight of the breast cancer patients, whole slides with adjacent normal tissue were not available, so adjacent normal areas were macro-dissected from tumor-containing slides. For the remaining patients, DNA was isolated from whole slides of adjacent normal tissue. Where dissection was used to obtain the normal tissue samples, most of the somatic variants called were detected in both the adjacent normal and the tumor samples. For the patients where adjacent normal tissue was obtained from separate slides, most patients still had a few somatic variants detected in the normal tissue. Thus, practical application of this approach to a set of FFPE breast and prostate samples shows the feasibility of this approach with typical archival samples. It is worth noting that one somatic variant detected in the adjacent normal tissue was a known PI3-kinase activating mutation.

Figure 25:
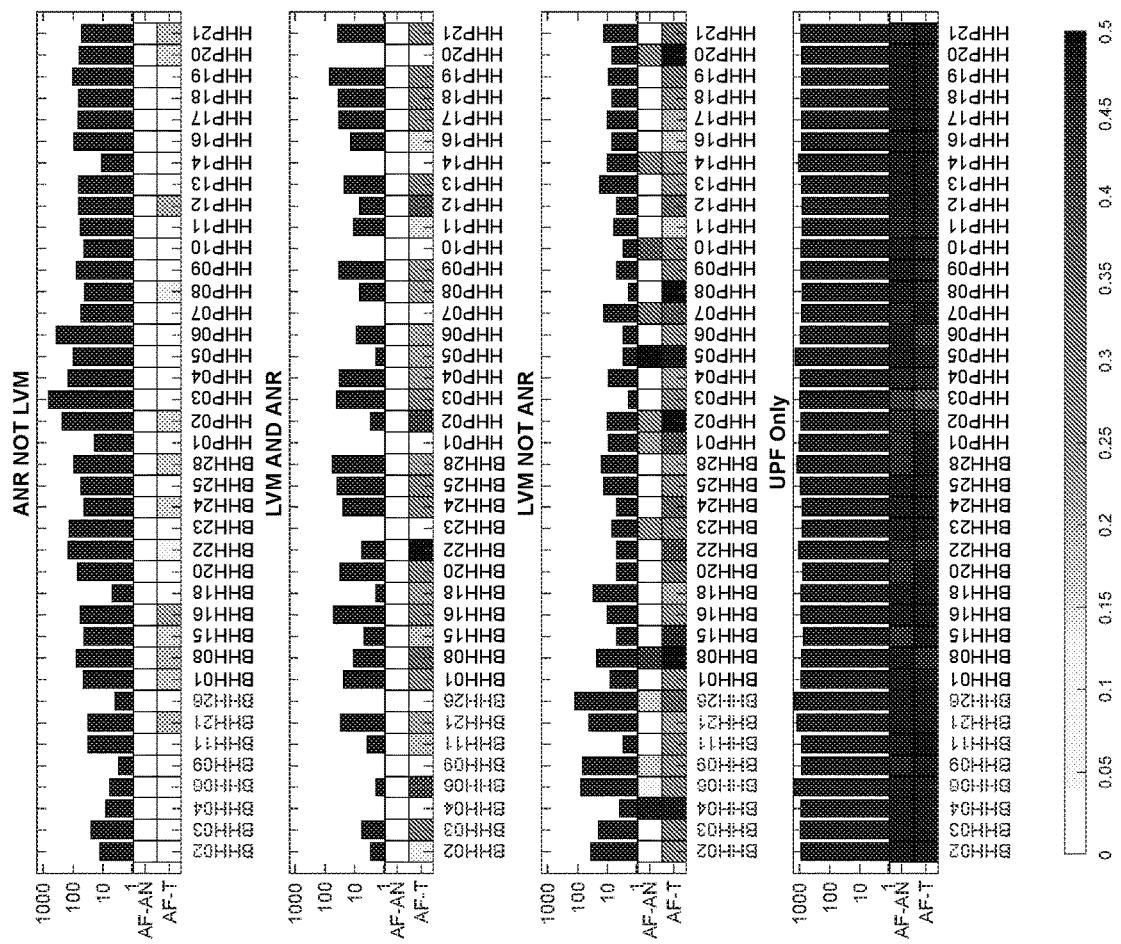
FIG. 25 Comparison of allelic fractions distributions in variant calling approaches of archival breast and prostate tumor samples. Histograms (left) or line plots (right) of the allelic fraction distributions for variants called by lumosVar (top), the UPF approach (center), and the ANR approach (bottom). The top plot shows the number of variants detected in each patient, with the color indicating how many variants were detected in only the low-tumor-content samples (orange), both samples (blue), or high-tumor-content samples only (green). The bottom plot shows the number of variants called germline heterozygous that were not found in dbSNP.

We also analyzed the archival tissue (FIG. 25). Two approaches were used: (1) a filtering strategy (unmatched plus filtering—UPF) where standard somatic variant calling tool(s) were used against an unmatched reference, and variants found in dbSNP were excluded as likely germline; and (2) a strategy (adjacent normal as reference—ANR) that used the tumor-adjacent normal sample as the normal reference in standard somatic variant calling tools. Using the UPF strategy, we found that most of the variants called using the filtering strategy have variant allele fractions around 50% in both the low- and high-tumor-content samples, suggesting that most are private germline variants. Using the ANR approach, we are only identifying variants with allele fractions in the adjacent normal sample that are at or very close to zero. The variants called by lumosVar generally have higher allele fractions in the tumor samples and low allele fractions in the adjacent normal samples, as expected.

Mutations called by any of the three approaches were compared against the Cancer Hotspots database, which reports recurrent mutations in 11,119 tumor samples[51]. A total of 28 hotspot mutations were called including eight mutations with in vitro or in vivo validation (level-3), two mutations detected in the Cancer Hotspots dataset that were previously reported (level-2), and eighteen mutations that were novel in the Cancer Hotspots dataset (level-1). Of the ten level-3 and level-2 mutations, all were called in the UNF approach, eight were called by LumosVarMulti, and only six were called in the ANR approach (FIG. 26). The two level-2 and level-3 mutations missed by lumosVarMulti had low allele fractions in the tumor sample (5-6%), while the four level-3 hotspots variants missed by the ANR approach had moderate allele fraction in the tumor (17-35%) and low allele fractions in the adjacent tissue (2-16%). The level-1 hotspots were called only in the UNF approach. These include the same APOBR mutation called in 13 patients and the same DHRS4 mutation called in four patients (FIG. 25). Putative mutations that are common within a dataset, but not know to be common in cancer, are suggestive of alignment artifacts[52].

Compared to using adjacent normal tissue sequencing in a standard paired somatic variant caller, the claimed methods avoid false negative due to tumor contamination in the adjacent tissue. The claimed methods also integrates somatic variant, germline variant, copy number variant, and clonal variant grouping into one statistical framework/software program.

REFERENCES

1. Hanahan, D. & Weinberg, R. A. The Hallmarks of Cancer. *Cell* 100, 57-70 (2000).
2. Frampton, G. M. et al. Development and validation of a clinical cancer genomic profiling test based on massively parallel DNA sequencing. *Nat. Biotechnol.* 31, 1023-1031 (2013).
3. Allen, E. M. V. et al. Whole-exome sequencing and clinical interpretation of FFPE tumor samples to guide precision cancer medicine. *Nat. Med.* 20, 682-688 (2014).
4. Cheng, D. T. et al. Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. *J. Mol. Diagn.* 17, 251-264 (2015).
5. Khurana, E. et al. Role of non-coding sequence variants in cancer. *Nat. Rev. Genet.* 17, 93-108 (2016).
6. Waldron, L. et al. Expression Profiling of Archival Tumors for Long-term Health Studies. *Clin. Cancer Res.* 18, 6136-6146 (2012).
7. Marrone, M., Schilsky, R. L., Liu, G., Khoury, M. J. & Freedman, A. N. Opportunities for Translational Epidemiology: The Important Role of Observational Studies to Advance Precision Oncology. *Cancer Epidemiol. Prev. Biomark.* 24, 484-489 (2015).
8. Jones, S. et al. Personalized genomic analyses for cancer mutation discovery and interpretation. *Sci. Transl. Med.* 7, 283ra53 (2015).
9. Wei, L. et al. Pitfalls of improperly procured adjacent non-neoplastic tissue for somatic mutation analysis using next-generation sequencing. *BMC Med. Genomics* 9, 64 (2016).
10. Dotto, G. P. Multifocal epithelial tumors and field cancerization: stroma as a primary determinant. *J. Clin. Invest.* 124, 1446-1453 (2014).
11. Heaphy, C. M., Griffith, J. K. & Bisoffi, M. Mammary field cancerization: molecular evidence and clinical importance. *Breast Cancer Res. Treat.* 118, 229-239 (2009).

12. Nonn, L., Ananthanarayanan, V. & Gann, P. H. Evidence for Field Cancerization of the Prostate. *The Prostate* 69, 1470-1479 (2009).
13. Hoang, M. L. et al. Genome-wide quantification of rare somatic mutations in normal human tissues using massively parallel sequencing. *Proc. Natl. Acad. Sci. U.S.A.* 113, 9846-9851 (2016).
14. Martincorena, I. et al. High burden and pervasive positive selection of somatic mutations in normal human skin. *Science* 348, 880-886 (2015).
15. Halperin, R. F. et al. A method to reduce ancestry related germline false positives in tumor only somatic variant calling. *BMC Med. Genomics* 10, 61 (2017).
16. Raymond V M, Gray S W, Roychowdhury S, Joffe S, Chinnaiyan A M, Parsons D W, et al. Germline Findings in Tumor-Only Sequencing: Points to Consider for Clinicians and Laboratories. J. Natl. Cancer Inst. 2016; 108:djv351.
17. Jones S, Anagnostou V, Lytle K, Parpart-Li S, Nesselbush M, Riley D R, et al. Personalized genomic analyses for cancer mutation discovery and interpretation. Sci. Transl. Med. 2015; 7:283ra53.
18. Garofalo A, Sholl L, Reardon B, Taylor-Weiner A, Amin-Mansour A, Miao D, et al. The impact of tumor profiling approaches and genomic data strategies for cancer precision medicine. Genome Med. 2016; 8:79.
19. Smith K S, Yadav V K, Pei S, Pollyea D A, Jordan C T, De S. SomVarIUS: somatic variant identification from unpaired tissue samples. Bioinformatics. 2015; btv685.
20. Consortium T 1000 GP. An integrated map of genetic variation from 1,092 human genomes. Nature. 2012; 491:56-65.
21. Kurian A W, Hare E E, Mills M A, Kingham K E, McPherson L, Whittemore A S, et al. Clinical Evaluation of a Multiple-Gene Sequencing Panel for Hereditary Cancer Risk Assessment. J. Clin. Oncol. 2014; 32:2001-9.
22. Richards C S, Bale S, Bellissimo D B, Das S, Grody W W, Hegde M R, et al. ACMG recommendations for standards for interpretation and reporting of sequence variations: Revisions 2007. Genet. Med. 2008; 10:294-300.
23. Vogelstein B, Papadopoulos N, Velculescu V E, Zhou S, Diaz L A, Kinzler K W. Cancer Genome Landscapes. Science. 2013; 339:1546-58.
24. Cheng D T, Mitchell T N, Zehir A, Shah R H, Benayed R, Syed A, et al. Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. J. Mol. Diagn. 2015; 17:251-64.
25. Meric-Bernstam F, Brusco L, Daniels M, Wathoo C, Bailey A M, Strong L, et al. Incidental germline variants in 1000 advanced cancers on a prospective somatic genomic profiling protocol. Ann. Oncol. 2016; 27:795-800.
26. Leiserson M D M, Vandin F, Wu H-T, Dobson J R, Eldridge J V, Thomas J L, et al. Pan-cancer network analysis identifies combinations of rare somatic mutations across pathways and protein complexes. Nat. Genet. 2014; 47:106-14.
27. Khurana E, Fu Y, Chakravarty D, Demichelis F, Rubin M A, Gerstein M. Role of non-coding sequence variants in cancer. Nat. Rev. Genet. 2016; 17:93-108.
28. Piraino S W, Furney S J. Beyond the exome: the role of non-coding somatic mutations in cancer. Ann. Oncol. 2016; 27:240-8.
29. Vinagre J, Almeida A, Pópulo H, Batista R, Lyra J, Pinto V, et al. Frequency of TERT promoter mutations in human cancers. Nat. Commun. 2013; 4:2185.
30. Lawrence M S, Stojanov P, Polak P, Kryukov G V, Cibulskis K, Sivachenko A, et al. Mutational heterogeneity in cancer and the search for new cancer genes. Nature. 2013; 499:214-8.
31. Fu Y, Liu Z, Lou S, Bedford J, Mu X J, Yip K Y, et al. FunSeq2: a framework for prioritizing noncoding regulatory variants in cancer. Genome Biol. [Internet]. 2014 [cited 2015 Jan. 5]; 15. Available from: http://www.ncbi.nlm.nih.gov/pmc/articles/PMC4203974/
32. Kilpivaara O, Aaltonen L A. Diagnostic Cancer Genome Sequencing and the Contribution of Germline Variants. Science. 2013; 339:1559-62.
33. Li J, Poursat M-A, Drubay D, Motz A, Saci Z, Morillon A, et al. A Dual Model for Prioritizing Cancer Mutations in the Non-coding Genome Based on Germline and Somatic Events. PLOS Comput Biol. 2015; 11:e1004583.
34. Li H, Durbin R. Fast and accurate short read alignment with Burrows-Wheeler transform. Bioinformatics. 2009; 25:1754-60.
35. Flicek P, Ahmed I, Amode M R, Barrell D, Beal K, Brent S, et al. Ensembl 2013. Nucleic Acids Res. 2013; 41:D48-55.
36. Mose L E, Wilkerson M D, Hayes D N, Perou C M, Parker J S. ABRA: improved coding indel detection via assembly-based realignment. Bioinformatics. 2014; 30:2813-5.
37. DePristo M A, Banks E, Poplin R, Garimella K V, Maguire J R, Hartl C, et al. A framework for variation discovery and genotyping using next-generation DNA sequencing data. Nat. Genet. 2011; 43:491-98.
38. Li H. A statistical framework for SNP calling, mutation discovery, association mapping and population genetical parameter estimation from sequencing data. Bioinforma. Oxf. Engl. 2011; 27:2987-93.
39. Garrison E, Marth G. Haplotype-based variant detection from short-read sequencing. ArXiv Prepr. ArXiv12073907 [Internet]. 2012 [cited 2015 Dec. 16]; Available from: http://arxiv.org/abs/1207.3907
40. Christoforides A, Carpten J D, Weiss G J, Demeure M J, Hoff D D V, Craig D W. Identification of somatic mutations in cancer through Bayesian-based analysis of sequenced genome pairs. BMC Genomics. 2013; 14:302.
41. Saunders C T, Wong W S W, Swamy S, Becq J, Murray L J, Cheetham R K. Strelka: accurate somatic small-variant calling from sequenced tumor-normal sample pairs. Bioinformatics. 2012; 28:1811-7.
42. Cibulskis K, Lawrence M S, Carter S L, Sivachenko A, Jaffe D, Sougnez C, et al. Sensitive detection of somatic point mutations in impure and heterogeneous cancer samples. Nat. Biotechnol. 35 2013; 31:213-9.
43. Tan A, Abecasis G R, Kang H M. Unified representation of genetic variants. Bioinformatics. 2015; 31:2202-4.
44. Sherry S T, Ward M H, Kholodov M, Baker J, Phan L, Smigielski E M, et al. dbSNP: the NCBI database of genetic variation. Nucleic Acids Res. 2001; 29:308-11.
45. Lee H, Schatz M C. Genomic dark matter: the reliability of short read mapping illustrated by the genome mappability score. Bioinformatics. 2012; 28:2097-105.
46. Pietras K, Östman A. Hallmarks of cancer: Interactions with the tumor stroma. Exp. Cell Res. 2010; 316:1324-31.
47. Aran D, Sirota M, Butte A J. Systematic pan-cancer analysis of tumor purity. Nat. Commun. 2015; 6:8971.
48. Ewing A D, Houlahan K E, Hu Y, Ellrott K, Caloian C, Yamaguchi T N, et al. Combining tumor genome simulation with crowdsourcing to benchmark somatic single-nucleotide-variant detection. Nat. Methods. 2015; 12:623-30.
49. Kwei K A, Kung Y, Salari K, Holcomb I N, Pollack J R. Genomic instability in breast cancer: pathogenesis and clinical implications. Mol. Oncol. 2010; 4:255.
50. Kalatskaya, I. et al. ISOWN: accurate somatic mutation identification in the absence of normal tissue controls. Genome Med. 9, 59 (2017).
51. Cancer Hotspots. Available at: http://cancerhotspots.org/#/home. (Accessed: 15 Dec. 2017)
52. Teer, J. K. et al. Evaluating somatic tumor mutation detection without matched normal samples. *Hum. Genomics* 11, 22 (2017).
53. Andor, N. et al. Pan-cancer analysis of the extent and consequences of intratumor heterogeneity. *Nat. Med.* 22, 105-113 (2015).
54. Andor, N., Maley, C. C. & Ji, H. P. Genomic Instability in Cancer: Teetering on the Limit of Tolerance. *Cancer Res.* 77, 2179-2185 (2017).
55. Saunders, N. A. et al. Role of intratumoural heterogeneity in cancer drug resistance: molecular and clinical perspectives. *EMBO Mol. Med.* 4, 675-684 (2012).
56. Troester, M. A. et al. DNA defects, epigenetics, and gene expression in cancer-adjacent breast: a study from The Cancer Genome Atlas. *NPJ Breast Cancer* 2, 16007 (2016).
57. Allen E M V, Miao D, Schilling B, Shukla S A, Blank C, Zimmer L, et al. Genomic correlates of response to CTLA-4 blockade in metastatic melanoma. Science. 2015; 350:207-11.
58. Byron, Sarah A. et al. Prospective Feasibility Trial for Genomics-Informed Treatment in Recurrent and Progressive Glioblastoma. Clinical Cancer Research. 24(2) Jan. 15, 2018.

What is claimed is:

1. A method of detecting one or more somatic tumor variants and/or germline variants from one or more tumor samples having a matched normal sample from a subject, comprising:
   a) receiving aligned sequence data from the one or more tumor samples having a matched normal sample;
   b) identifying a candidate variant within the aligned sequence data;
   c) observing an allelic fraction of the identified candidate variant in the one or more tumor samples having a matched normal sample;
   d) computer modeling to find a copy number state estimate of the identified candidate variant and a tumor-cell fraction of each of the one or more tumor samples having a matched normal sample; wherein the copy number state estimates of the identified candidate variants with the aligned sequence data and the tumor-cell fractions of the variants in the samples are modeled jointly;
   e) predicting an expected allelic fraction of the identified candidate variant by assuming a somatic or a germline status; and
   f) determining whether each candidate variant is a somatic variant or a germline variant by comparing the observed allelic fraction to the expected allelic fraction.

2. The method of claim 1, wherein the one or more tumor samples having a matched normal sample are archival samples, formalin fixed paraffin embedded (FFPE) samples, or both.

3. The method of claim 1, further comprising:
   a. identifying two or more sample regions having different tumor contents; and
   b. macro-dissecting to separate the two or more sample regions.

4. The method of claim 1, wherein the candidate variant is a single-nucleotide variant (SNV), an insertion or a deletion (INDEL), or a noncoding mutation.

5. The method of claim 1, further comprising verifying the somatic or germline status using one or more germline variant callers or one or more somatic variant callers,
   wherein the one or more germline variant callers are HAPLOTYPE CALLER, samtools, and/or freebayes and the one or more somatic variant callers are SEURAT, STRELKA, MUTECT, or a combination thereof.

* * * * *